US011141463B2

(12) United States Patent
Porgador et al.

(10) Patent No.: US 11,141,463 B2
(45) Date of Patent: Oct. 12, 2021

(54) FUSION PROTEINS WITH EXTENDED SERUM HALF LIFE

(71) Applicants: THE NATIONAL INSTITUTE FOR BIOTECHNOLOGY IN THE NEGEV LTD., Beer Sheva (IL); B. G. NEGEV TECHNOLOGIES AND APPLICATIONS LTD., AT BEN-GURION UNIVERSITY, Beer Sheva (IL)

(72) Inventors: Ari-Angel Porgador, Lehavim (IL); David Ben-Menahem, Omer (IL); Roee Atlas, Givataim (IL)

(73) Assignees: THE NATIONAL INSTITUTE FOR BIOTECHNOLOGY IN THE NEGEV LTD., Beer Sheva (IL); B. G. NEGEV TECHNOLOGIES AND APPLICATIONS LTD., AT BEN-GURION UNIVERSITY, Beer Sheva (IL)

( * ) Notice: Subject to any disclaimer, the term of this patent is extended or adjusted under 35 U.S.C. 154(b) by 0 days.

(21) Appl. No.: 16/316,410

(22) PCT Filed: Jul. 11, 2017

(86) PCT No.: PCT/IL2017/050788
§ 371 (c)(1),
(2) Date: Jan. 9, 2019

(87) PCT Pub. No.: WO2018/011803
PCT Pub. Date: Jan. 18, 2018

(65) Prior Publication Data
US 2019/0255150 A1 Aug. 22, 2019

Related U.S. Application Data

(60) Provisional application No. 62/360,524, filed on Jul. 11, 2016, provisional application No. 62/421,400, filed on Nov. 14, 2016.

(51) Int. Cl.
| | | |
|---|---|---|
| *A61K 38/19* | (2006.01) | |
| *A61K 38/18* | (2006.01) | |
| *A61K 38/00* | (2006.01) | |
| *A61K 47/64* | (2017.01) | |
| *C07K 14/55* | (2006.01) | |
| *C07K 14/59* | (2006.01) | |
| *C07K 14/61* | (2006.01) | |
| *C07K 19/00* | (2006.01) | |

(52) U.S. Cl.
CPC .............. *A61K 38/19* (2013.01); *A61K 38/18* (2013.01); *A61K 47/642* (2017.08); *C07K 14/55* (2013.01); *C07K 14/59* (2013.01); *C07K 14/61* (2013.01); *C07K 19/00* (2013.01); *A61K 38/00* (2013.01); *C07K 2319/31* (2013.01); *C07K 2319/33* (2013.01)

(58) Field of Classification Search
None
See application file for complete search history.

(56) References Cited

U.S. PATENT DOCUMENTS

| | | | |
|---|---|---|---|
| 5,118,666 A | 6/1992 | Habener | |
| 9,061,059 B2* | 6/2015 | Chakraborty | .......... C07K 16/40 |
| 2004/0072256 A1 | 4/2004 | Mandelboim et al. | |
| 2007/0203054 A1 | 8/2007 | Mandelboim | |
| 2010/0047169 A1 | 2/2010 | Mandelboim et al. | |
| 2015/0105334 A1* | 4/2015 | Porgador | ................. C07K 7/06 |
| | | | 514/21.3 |

FOREIGN PATENT DOCUMENTS

| | | |
|---|---|---|
| EP | 2857417 A1 | 4/2015 |
| WO | 0208287 A3 | 12/2002 |
| WO | 2004053054 A2 | 6/2004 |
| WO | 2005000086 A2 | 1/2005 |
| WO | 2005051973 A2 | 6/2005 |
| WO | 2010106542 A2 | 9/2010 |
| WO | 2013140393 A1 | 9/2013 |
| WO | 2013184938 A2 | 12/2013 |
| WO | 2015015489 A1 | 2/2015 |
| WO | 2018109770 A1 | 6/2018 |
| WO | 2018109771 A1 | 6/2018 |

OTHER PUBLICATIONS

NCBI Accession No. NP_01186438, for Natural Cytotoxicity Triggering Receptor 2 (NCR2) isoform 2, Jan. 2, 2020.*
Solomon et al., "Large-scale preparation and in vitro characterization of biologically active human placental (20 and 22K) and pituitary (20K) growth hormones: Placental growth hormones have no lactogenic activity in humans", Elsevier, Growth Hormone & IGF Research 16, 297-307, 2006.
Roland E Kontermann, "Strategies for extended serum half-life of protein therapeutics", Current Opinion in Biotechnology 2011, 22:868-876.
Flintegaard et al., "N-Glycosylation Increases the Circulatory Half-Life of Human Growth Hormone", Endocrinology, Nov. 2010, 151(11):5326-5336.
Berhani et al., "Human anti-NKp46 antibody for studies of NKp46-dependent NK cell function and its applications for type 1 diabetes and cancer research", European Journal of Immunology, Feb. 2019, 49(2):228-241.
Edri et al., "The Ebola-Glycoprotein Modulates the Function of Natural Killer Cells", Frontiers in Immunology, Jul. 2, 2018; 9:1428.
Shemesh et al., "NKp44-Derived Peptide Binds Proliferating Cell Nuclear Antigen and Mediates Tumor Cell Death." Frontier of Immunology, May 23, 2018; 9:1114.

(Continued)

*Primary Examiner* — Marianne P Allen
(74) *Attorney, Agent, or Firm* — The Roy Gross Law Firm, LLC; Roy Gross

(57) ABSTRACT

Peptides derived from NKp44 protein, chimeric peptides, nucleotides encoding same and pharmaceutical compositions comprising same, are provided. Further, methods of extending the biological half-life of a protein of interest are provided.

16 Claims, 14 Drawing Sheets

Specification includes a Sequence Listing.

(56) References Cited

OTHER PUBLICATIONS

Shemesh et al., "Splice variants of human natural cytotoxicity receptors: novel innate immune checkpoints." Cancer Immunology, Immunotherapy Dec. 2018; 67(12): 1871-1883.

Pazina et al., "Regulation of the Functions of Natural Cytotoxicity Receptors by Interactions with Diverse Ligands and Alterations in Splice Variant Expression." Frontiers of Immunology, Mar. 30, 2017; 8:369.

Shemer-Avni et al., "Expression of NKp46 Splice Variants in Nasal Lavage Following Respiratory Viral Infection: Domain 1-Negative Isoforms Predominate and Manifest Higher Activity." Frontiers of Immunology, Feb. 15, 2017; 8:161.

Shemesh et al., "NKp44 and NKp30 splice variant profiles in decidua and tumor tissues: a comparative viewpoint" Oncotarget. Oct. 25, 2016; 7(43): 70912-70923.

Shemesh et al., "Survival in acute myeloid leukemia is associated with NKp44 splice variants." Oncotarget. May 31, 2016; 7(22): 32933-45.

Hadad et al., "NKp46 Clusters at the Immune Synapse and Regulates NK Cell Polarization." Frontiers of Immunology, Sep. 25, 2015; 6:495.

Shemesh et al., "First Trimester Pregnancy Loss and the Expression of Alternatively Spliced NKp30 Isoforms in Maternal Blood and Placental Tissue." Frontiers of Immunology, Jun. 1, 2015;6:189.

Frishman-Levy et al., "Central nervous system acute lymphoblastic leukemia: role of natural killer cells." Blood. May 28, 2015; 125(22):3420-31.

Yossef et al., "Targeting natural killer cell reactivity by employing antibody to NKp46: implications for type 1 diabetes." PLoS One. Feb. 26, 2015; 10(2):e0118936.

Brusilovsky et al., "Regulation of natural cytotoxicity receptors by heparan sulfate proteoglycans in -cis: A lesson from NKp44." European Journal of Immunology, Apr. 2015;45(4): 1180-91.

Tal et al., "An NCR1-based chimeric receptor endows T-cells with multiple anti-tumor specificities." Oncotarget. Nov. 15, 2014; 5(21): 10949-58.

Guttman et al., "α1-Antitrypsin modifies general NK cell interactions with dendritic cells and specific interactions with islet β-cells in favor of protection from autoimmune diabetes." Immunology. Oct. 13, 2014.

Brusilovsky et al., "Carbohydrate-mediated modulation of NK cell receptor function: structural and functional influences of heparan sulfate moieties expressed on NK cell surface." Frontiers in Oncology, Jul. 16, 2014; 4:185.

Glatzer et al., "RORyt+innate lymphoid cells acquire a proinflammatory program upon engagement of the activating receptor NKp44." Immunity. Jun. 27, 2013; 38(6):1223-35.

Rosental et al., "A novel mechanism for cancer cells to evade immune attack by NK cells: The interaction between NKp44 and proliferating cell nuclear antigen." Oncoimmunology. Jul. 1, 2012; 1(4):572-574.

Jaron-Mendelson et al., "Dimerization of NKp46 receptor is essential for NKp46-mediated lysis: characterization of the dimerization site by epitope mapping." Journal of Immunology, Jun. 15, 2012; 188(12):6165-74.

Brusilovsky et al., "Human NK cell recognition of target cells in the prism of natural cytotoxicity receptors and their ligands." Journal of Immunotoxicology, Jul.-Sep. 2012; 9(3):267-74.

Rosental et al., "Proliferating cell nuclear antigen is a novel inhibitory ligand for the natural cytotoxicity receptor NKp44." Journal of Immunology, Dec. 1, 2011; 187(11):5693-702.

Gur C. et al., "Recognition and killing of human and murine pancreatic beta cells by the NK receptor NKp46." Journal of Immunology, Sep. 15, 2011; 187(6):3096-103.

Mendelson et al., "NKp46 O-glycan sequences that are involved in the interaction with hemagglutinin type 1 of influenza virus." Journal of Virology, Apr. 2010; 84(8):3789-97.

Achdout et al., "Killing of avian and Swine influenza virus by natural killer cells." Journal of Virology, Apr. 2010; 84(8):3993-4001.

Gur et al., "The activating receptor NKp46 is essential for the development of type 1 diabetes." Nature Immunology, Feb. 2010; 11(2):121-8.

Hershkovitz et al., "NKp44 receptor mediates interaction of the envelope glycoproteins from the West Nile and dengue viruses with NK cells." Journal of Immunology, Aug. 15, 2009; 183(4):2610-21.

Hecht et al., "Natural cytotoxicity receptors NKp30, NKp44 and NKp46 bind to different heparan sulfate/heparin sequences." Journal of Proteome Research, Feb. 2009; 8(2):712-20.

Amon et al., "Harnessing soluble NK cell killer receptors for the generation of novel cancer immune therapy." PLoS One. May 14, 2008; 3(5):e2150.

Ho et al., "H5-type influenza virus hemagglutinin is functionally recognized by the natural killer-activating receptor NKp44." Journal of Virology, Feb. 2008; 82(4):2028-32.

Hershkovitz et al., "Altered glycosylation of recombinant NKp30 hampers binding to heparan sulfate: a lesson for the use of recombinant immunoreceptors as an immunological tool." Glycobiology. Jan. 2008; 18(1):28-41.

Cagnano et al., "Expression of ligands to NKp46 in benign and malignant melanocytes." Journal of Investigative Dermatology, Apr. 2008; 128(4):972-9.

Hershkovitz et al., "Characterization of the recognition of tumor cells by the natural cytotoxicity receptor, NKp44." Biochemistry. Jun. 26, 2007; 46(25):7426-36.

Garg et al., "Vimentin expressed on *Mycobacterium tuberculosis*-infected human monocytes is involved in binding to the NKp46 receptor" Journal of Immunology, Nov. 1, 2006; 177(9):6192-8.

Gazit et al., "Lethal influenza infection in the absence of the natural killer cell receptor gene Ncr1." Nature Immunology, May 2006; 7(5):517-23.

Zilka et al., "Characterization of the heparin/heparan sulfate binding site of the natural cytotoxicity receptor NKp46." Biochemistry. Nov. 8, 2005; 44(44)14477-85.

Vankayalapati et al., "Role of NK cell-activating receptors and their ligands in the lysis of mononuclear phagocytes Infected with an intracellular bacterium." Journal of Immunology, Oct. 1, 2005; 175(7):4611-7.

Arnon et al., "Inhibition of the NKp30 activating receptor by pp65 of human cytomegalovirus." Nature Immunology, May 2005; 6(5):515-23.

Porgador et al., "Natural cytotoxicity receptors: pattern recognition and involvement of carbohydrates." ScientificWorldJournal. Feb. 23, 2005;5:151-4.

Bloushtain et al., "Membrane-associated heparan sulfate proteoglycans are involved in the recognition of cellular targets by NKp30 and NKp46." Journal of Immunology, Aug. 15, 2004; 173(4):2392-401.

Markel et al., "The mechanisms controlling NK cell autoreactivity in TAP2-deficient patients." Blood. Mar. 1, 2004;103(5):1770-8.

Arnon et al., "The mechanisms controlling the recognition of tumor- and virus-infected cells by NKp46." Blood. Jan. 15, 2004; 103(2):664-72.

Vankayalapati et al., "The NKp46 receptor contributes to NK cell lysis of mononuclear phagocytes infected with an intracellular bacterium." Journal of Immunology, Apr. 1, 2002; 168(7)3451-7.

* cited by examiner

FUSION PROTEINS WITH EXTENDED SERUM HALF LIFE

CROSS-REFERENCE TO RELATED APPLICATIONS

This application is a National Phase of PCT Patent Application No. PCT/IL2017/050788 having International filing date of Jul. 11, 2017, which claims the benefit of priority of U.S. Provisional Patent Application No. 62/360,524 filed Jul. 11, 2016 and U.S. Provisional Patent Application No. 62/421,400 filed Nov. 14, 2016, the contents of the above applications are all incorporated by reference as if fully set forth herein in their entirety.

FIELD OF INVENTION

The present invention is directed to, inter alia, fusion proteins with extended in vivo stability. More particularly, the invention concerns gaining extended stability of proteins by their fusion to a peptide derived from NKp44.

BACKGROUND OF THE INVENTION

Peptides are susceptible to denaturation or enzymatic degradation in the blood, liver or kidney. Accordingly, peptides typically have short circulatory half-lives of several hours. A low stability of peptide drugs dictates a sustained frequency delivery in order to maintain an effective plasma concentration of the active peptide.

Unfavorable pharmacokinetics, such as a short serum half-life, can prevent the pharmaceutical development of many otherwise promising drug candidates. Serum half-life is an empirical characteristic of a molecule, and must be determined experimentally for each new potential drug. Therefore, technologies prolonging the half-lives of therapeutic peptides while maintaining a high pharmacological efficacy thereof are desired.

NKp44 is a natural cytotoxicity receptor expressed on the plasmatic membrane of Natural Killer cells. Specific peptides derived from NKp44 were previously disclosed, such as in US patent application No. 2007/0203054 which relates to hyper-glycosylated peptides that are derived from the NKp44 receptor, capable of specific targeting of viral-infected cells. Further, US patent application No. 2004/0072256 discloses a targeting complex, capable of targeting an active substance to a target cell, NKp44 or a functional fragment thereof; and an active segment comprising an active substance such as cytotoxic moiety; an imaging moiety; or an Ig fragment. US patent application No. 2010/0047169 discloses conjugates and fusion proteins of Natural Killer cytotoxicity receptors NKp30, NKp46 and NKp44, or active fragments thereof and an active agent selected from a cytotoxic drug or an Ig fragment effective in targeting tumor cells in vivo.

SUMMARY OF THE INVENTION

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

According to one aspect, the present invention provides a chimera comprising a growth hormone attached to a peptide comprising an amino acid sequence as set forth in SEQ ID NO: 3. In some embodiments, the growth hormone comprises the amino acid sequence as set forth in SEQ ID NO: 16. In some embodiments, the peptide is attached to at least one position selected from the group consisting of: the amino terminus of said growth hormone, the carboxy terminus of said growth hormone, and between a first and a second subunit of said growth hormone. In some embodiments, the chimera comprises the amino acid sequence selected from the group consisting of: SEQ ID NO: 22, SEQ ID NO: 29, SEQ ID NO: 32, SEQ ID NO: 52, SEQ ID NO: 53, SEQ ID NO: 60, and SEQ ID NO: 71.

According to another aspect, the present invention provides a peptide comprising or consisting of 20 to 50 amino acid residues derived from amino acids 130 to 199 of SEQ ID NO: 1. In some embodiments, the peptide comprises the amino acid sequence as set forth in SEQ ID NOs: 3 or 4.

In some embodiments, the invention provides a chimera comprising a peptide of 20 to 50 amino acid residues derived from amino acids 130 to 199 of SEQ ID NO: 1, attached to a protein of interest.

In some embodiments, the protein of interest has a biological activity. In some embodiments, the protein of interest is a cytokine. In some embodiments, the protein of interest is a hormone. In some embodiments, the protein of interest is selected from the group consisting of: a chorionic gonadotropin (CG), and a growth hormone (GH).

In some embodiments, the peptide is attached to the amino terminus of the protein of interest. In some embodiments, the peptide is attached to the carboxy terminus of the protein of interest. In some embodiments, the peptide is attached to at least one position selected from the group consisting of: the amino terminus of the protein of interest, the carboxy terminus of the protein of interest, and between a first and a second portions of the protein of interest.

In some embodiments, the chimera comprises two or more peptides derived from amino acids 130 to 199 of SEQ ID NO: 1. In one embodiment, a first peptide derived from amino acids 130 to 199 of SEQ ID NO: 1 is attached to the amino terminus of said protein of interest, and a second peptide derived from amino acids 130 to 199 of SEQ ID NO: 1 is attached to the carboxy terminus of the protein of interest.

In some embodiments, the invention provides a pharmaceutical composition comprising the peptide, or the chimera of the invention, and a pharmaceutically acceptable carrier. In some embodiments, there is provided the pharmaceutical composition of the invention, for use in treating a condition, a disease or a disorder in a subject in need thereof. In some embodiments, there is provided the pharmaceutical composition of the invention, for use in treating or reducing a condition treatable by the protein of interest in a subject in need thereof.

In some embodiments, the invention provides a polynucleotide comprising a nucleic acid sequence encoding any of the peptides of the invention or any of the chimeras of the invention.

In some embodiments, the invention provides a vector comprising a polynucleotide, the polynucleotide comprises a nucleic acid sequence encoding any of the peptides of the invention or any of the chimeras of the invention.

According to another aspect, there is provided a method of extending the biological half-life of a protein of interest, the method comprising the step of attaching at least one peptide comprising 20 to 70 amino acid residues derived from amino acids 130 to 199 of SEQ ID NO: 1, to a protein of interest, thereby extending the biological half-life of a protein of interest.

In some embodiments, the peptide comprises an amino acid sequence selected from the group consisting of: SEQ ID NO: 2, SEQ ID NO: 3, SEQ ID NO: 4, and SEQ ID NO: 5.

In some embodiments, the protein of interest is selected from the group consisting of: CG, and GH. In some embodiments, the protein of interest is a cytokine, such as interleukin-2.

In some embodiments, extending the biological half-life of a protein of interest results in one of: reducing the dosing frequency, reducing the dosage of the protein of interest, and increasing compliance in the use of the protein of interest.

In some embodiments, there is provided a method of treating or reducing a condition in a subject in need thereof, the method comprising the step of administering to the subject a therapeutically effective amount of a chimera of the invention.

In some embodiments, there is provided a method of treating or reducing a condition treatable by a protein of interest, comprising the step of administering to the subject a therapeutically effective amount of a chimera of the invention.

In some embodiments, the protein of interest is selected from the group consisting of: CG, and GH. In some embodiments, the condition treatable by a protein is a condition treatable by: CG and/or GH.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
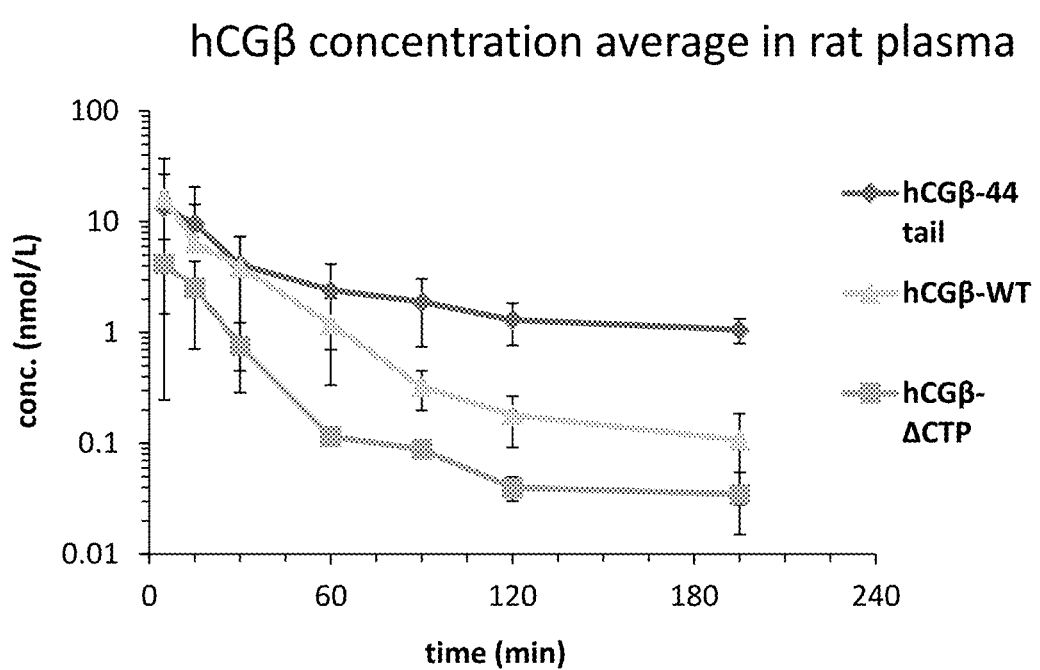
FIG. 1 is a graph illustrating the change in plasma concentration of human chorionic gonadotropin (hCG)-β-WT, hCG-β-ΔCTP, or hCG-β-44 tail variant following a single intravenous (IV) injection of hCG-β-WT, hCG-β-ΔCTP or hCG-β-44 tail to rats.

The present invention provides a peptide derived from or corresponding to amino acids 130 to 199 of NKp44 (SEQ ID NO: 1), or an analog, a derivative or a fragment thereof, methods of producing same, nucleotides encoding same, and methods of use thereof. The present invention further provides a long acting chimera, comprising: a protein of interest or a fragment thereof and at least one peptide derived from or corresponding to amino acids 130 to 199 of NKp44 (SEQ ID NO: 1), or analogs, derivatives or fragments thereof, nucleotides encoding same, and methods of producing and using the same.

The present invention is based, in part, on the surprising finding that a chimera comprising a protein-of-interest (e.g., human chorionic gonadotropin) fused to amino acids 130-199 of NKp44 showed prolonged biological and serum half-life as compared to an unmodified protein-of-interest.

The present invention is also based, in part, on the surprising finding that a chimera comprising human growth hormone (hGH) fused to a peptide derived from amino acids 130-199 of NKp44 (SEQ ID NO: 3 or 4) showed prolonged biological and serum half-life as compared to the unmodified hGH. Furthermore, the hGH chimera fused to a peptide of SEQ ID NO: 3 or 4, further exhibited enhanced potency compared to that of the unmodified hGH.

As used herein "unmodified protein" refers to the protein which is not fused to any of the NKp44-derived peptides of the instant invention.

Thus, in one aspect, the present invention introduces a new tool for extending and prolonging biological half-life. In some embodiments, the invention provides peptides and methods for enhancing the efficacy and/or potency of any protein of interest, by attaching at least one peptide derived from amino acids 130 to 199 of NKp44 (SEQ ID NO: 1) to the protein of interest.

As used herein, the terms "peptide", "polypeptide" and "protein" are used interchangeably to refer to a polymer of amino acid residues. The terms "peptide", "polypeptide" and "protein" as used herein encompass native peptides, peptidomimetics (typically including non-peptide bonds or other synthetic modifications) and the peptide analogs peptoids and semi-peptoids or any combination thereof. In another embodiment, the terms "peptide", "polypeptide" and "protein" apply to amino acid polymers in which one or more amino acid residue is an artificial chemical analog of a corresponding naturally occurring amino acid.

The term "chimera" refers to a polypeptide formed by the joining of two or more peptides through a peptide bond formed between the amino terminus of one peptide and the carboxyl terminus of another peptide. The chimera may be formed by a chemical coupling of the constituent peptides or it may be expressed as a single polypeptide fusion protein from a nucleic acid sequence encoding the single contiguous conjugate.

NKp44 Peptides

According to some embodiments, the invention provides a peptide of 20 to 50 amino acid residues, said peptide comprising a sequence derived from amino acids 130 to 199 of NKp44 (SEQ ID NO: 1). According to some embodiments, the invention provides a peptide of 20 to 50 amino acid residues derived from SEQ ID NO: 2.

In another embodiment, there is provided a peptide, derived from amino acids 130 to 199 of SEQ ID NO: 1, wherein said peptide is devoid of: (a) a fragment consisting of amino acids 1 to 129, and (b) a fragment consisting of amino acids 200 to 270.

In another embodiment, the peptide comprises at least 20, 21, 22, 23, 24, 25, 26, 27, 28, 29, 30, 31, 32, 33, 34, or 35 contiguous amino acids derived from amino acids 130 to 199 of SEQ ID NO: 1. Each possibility represents a separate embodiment of the present invention.

In one embodiment, there is provided a peptide comprising at least 20, 21, 22, 23, 24, 25, 26, 27, 28, 29, 30, 31, 32, 33, 34, or 35 contiguous amino acids derived from amino acids 130 to 199 of SEQ ID NO: 1, wherein the peptide is devoid of: (a) a fragment consisting of amino acids 1 to 129, and (b) a fragment consisting of amino acids 200 to 270. Each possibility represents a separate embodiment of the present invention.

In some embodiments, the NKp44 is a human NKp44 receptor (GenBank accession No: NP001186438.1) as set forth in SEQ ID NO: 1 MAWRALHPLLLLLLL-FPGSQAQSKAQVLQSVAGQTLTVRCQYPPTGSLY-EKKGWCKEA SALVCIRLVTSSKPRTMAW-TSRFTIWDDPDAGFFTVTMTDLREEDSGHYWCRI-YRPSDNS VSKSVRFYLVVSPASASTQTSWT-PRDLVSSQTQTQSCVPPTAGARQAPESPSTIPVPSHPS SPLPVPLPSRPQNSTLRPGPAAPIALVPVFCGLL-VAKSLVLSALLVWWVLRNRHMQHQG RSLLH-PAQPRPQAHRHFPLSHRAPGGTYGGKP.

As used herein, the term "derived from" or "corresponding to" refers to construction of an amino acid sequence based on the knowledge of a sequence using any one of the suitable means known to one skilled in the art, e.g. chemical synthesis in accordance with standard protocols in the art. In one embodiment, a peptide derived from or corresponding to amino acids 130 to 199 of the sequence of NKp44 is a peptide based on residues 130 to 199 of SEQ ID NO: 1, or an analog, a variant, a derivative or a fragment thereof. In one embodiment, the peptide derived from or corresponding to amino acids 130 to 199 of SEQ ID NO: 1, has the amino acid sequence as set forth in SEQ ID NO: 2, or an analog, a variant, a derivative or a fragment thereof.

In another embodiment, the peptides comprising the amino acid sequence as set forth in SEQ ID NO: 2 have a length of less than 80, 79, 78, 77, 76, 75, 74, 73, 72, 71, or 70 amino acids. Each possibility represents a separate embodiment of the present invention. In another embodiment, the peptide derived from NKp44 has a truncated form and/or is a fragment of SEQ ID NO: 2. In another embodiment, the peptide derived from NKp44 comprises at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 65, 66, 67, 68, 69 or 70 amino acids derived from SEQ ID NO: 2. Each possibility represents a separate embodiment of the invention. In another embodiment, the peptide derived from NKp44 comprises 20 to 70, 20 to 60, 20 to 55, 20 to 50, 20 to 40, 25 to 70, 25 to 60, 25 to 55, 25 to 50, 25 to 40, 30 to 70, 30 to 60, 30 to 50, or 30 to 40 amino acids derived from SEQ ID NO: 2. Each possibility represents a separate embodiment of the present invention. In another embodiment, the peptide derived from NKp44 is 20 to 70, 20 to 60, 20 to 55, 20 to 50, 20 to 40, 25 to 70, 25 to 60, 25 to 55, 25 to 50, 25 to 40, 30 to 70, 30 to 60, 30 to 50, or 30 to 40 amino acids long. Each possibility represents a separate embodiment of the present invention.

In one embodiment, the peptide derived from NKp44 comprises or consists of the amino acid sequence as set forth in SEQ ID NO: 3 and/or SEQ ID NO: 4. In one embodiment, the peptide derived from NKp4 comprises or consists of the amino acid sequence as set forth in SEQ ID NO: 3. In one embodiment, the truncated peptide derived from NKp44 comprises or consists of the amino acid sequence as set forth in SEQ ID NO: 4.

One of skill in the art will recognize that individual substitutions, deletions or additions to a peptide, or protein sequence which alters, adds, or deletes a single amino acid or a small percentage of amino acids in the encoded sequence is a conservatively modified variant where the alteration results in the substitution of an amino acid with a similar charge, size, and/or hydrophobicity characteristics, such as, for example, substitution of a glutamic acid (E) to aspartic acid (D).

In some embodiments, the peptide derived from NKp44 comprises a sequence derived from SEQ ID NO: 2, with one or more conservative substitution. According to another embodiment of the invention, the peptide derived from NKp44 comprises a sequence homologous to SEQ ID NO: 2. According to another embodiment of the invention, the peptide derived from NKp44 comprises a sequence having greater than 70%, 75%, 80%, 85%, 90% or 95% homology to SEQ ID NO: 2. Each possibility represents a separate embodiment of the present invention.

As used herein, the term "analog" includes any peptide having an amino acid sequence substantially identical to one of the sequences specifically shown herein in which one or more residues have been conservatively substituted with a functionally similar residue and which displays the abilities as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. Each possibility represents a separate embodiment of the present invention.

As used herein, the phrase "conservative substitution" also includes the use of a chemically derivatized residue in place of a non-derivatized residue provided that such peptide displays the requisite function such as iron precipitation as specified herein.

In another embodiment, the peptide derived from amino acids 130 to 199 of SEQ ID NO: 1 is a variant of native NKp44 or a fragment thereof, which differs by at least 1, 2, 3, 4, 5, 6, 7, 8, 9, 10, or 20 conservative amino acid substitutions from the amino acid 130-199 of native NKp44 (SEQ ID NO: 1) or a fragment thereof. Each possibility represents a separate embodiment of the present invention. In another embodiment, the peptide derived from NKp44 is a variant of the native NKp44 which differs by at least 1, 2, 3, 4, 5, 6, 7, 8, 9, or 10 modifications from SEQ ID NO: 2. Each possibility represents a separate embodiment of the present invention. In another embodiment, the peptide derived from NKp44 is a variant of the native NKp44 which differs by at most 1, 2, 3, 4, 5, 6, 7, 8, 9, or 10 modifications from SEQ ID NO: 2. Each possibility represents a separate embodiment of the invention.

In one embodiment, the peptide derived from NKp44 is a variant of SEQ ID NO: 2 comprising or consisting of the amino acid sequence as set forth in SEQ ID NO: 5.

In another embodiment, the term "variant" refers to a polypeptide or nucleotide sequence which comprises a modification of one or more amino acids or nucleotides as compared to another polypeptide or polynucleotide, respectively. In some embodiments, the modification are substitution, deletion, and/or insertion of one or more amino acids or nucleotides as compared to another polypeptide or polynucleotide, respectively. In some embodiments, the changes may be of minor nature, such as conservative amino acid substitutions or for nucleotide sequence resulting in conservative amino acid substitutions that do not significantly affect the activity of the polypeptide. In some embodiments, the changes may be substitution of an amino acid molecule, resulting in an addition of a glycosylation site (N- or O-linked), thereby increasing glycosylation of the polypeptide.

Typically, the present invention encompasses derivatives of the peptides. The term "derivative" or "chemical derivative" includes any chemical derivative of the peptide having one or more residues chemically derivatized by reaction of side chains or functional groups. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also, included as chemical derivatives are those peptides, which contain one or more naturally occurring amino acid derivatives of the twenty standard amino acid residues. For example: 4-hydroxyproline may be substituted for proline; 5-hydroxylysine may be substituted for lysine; 3-methylhistidine may be substituted for histidine; homoserine may be substituted or serine; and ornithine may be substituted for lysine.

In addition, a peptide derivative can differ from the natural sequence of the peptides of the invention by chemical modifications including, but are not limited to, terminal-NH2 acylation, acetylation, or thioglycolic acid amidation, and by terminal-carboxylamidation, e.g., with ammonia, methylamine, and the like. Peptides can be either linear, cyclic or branched and the like, which conformations can be achieved using methods well known in the art.

The peptide derivatives and analogs according to the principles of the present invention can also include side chain bond modifications, including but not limited to —CH2—NH—, —CH$_2$—S—, —CH$_2$—S=0, OC—NH—, —CH$_2$—O—, —CH$_2$—CH$_2$—, S=C—NH—, and —CH=CH—, and backbone modifications such as modified peptide bonds. Peptide bonds (—CO—NH—) within the peptide can be substituted, for example, by N-methylated bonds (—N(CH$_3$)—CO—); ester bonds (—C(R)H—C-0-0-C(R)H—N); ketomethylene bonds (—CO—CH$_2$—); a-aza bonds (—NH—N(R)—CO—), wherein R is any alkyl group, e.g., methyl; carba bonds (—CH$_2$—NH—); hydroxyethylene bonds (—CH(OH)—CH$_2$—); thioamide bonds (—CS—NH); olefmic double bonds (—CH=CH—); and peptide derivatives (—N(R)—CH$_2$—CO—), wherein R is the "normal" side chain, naturally presented on the carbon atom. These modifications can occur at one or more of the bonds along the peptide chain and even at several (e.g., 2-3) at the same time.

The present invention also encompasses peptide derivatives and analogs in which free amino groups have been derivatized to form amine hydrochlorides, p-toluene sulfonylamino groups, carbobenzoxyamino groups, t-butyloxycarbonylamino groups, chloroacetylamino groups or formylamino groups. Free carboxyl groups may be derivatized to form, for example, salts, methyl and ethyl esters or other types of esters or hydrazides. The imidazole nitrogen of histidine can be derivatized to form N-im-benzylhistidine.

As used herein the term "salts" refers to both salts of carboxyl groups and to acid addition salts of amino or guanido groups of the peptide molecule. Salts of carboxyl groups may be formed by means known in the art and include inorganic salts, for example sodium, calcium, ammonium, ferric or zinc salts, and the like, and salts with organic bases such as salts formed for example with amines such as triethanolamine, piperidine, procaine, and the like. Acid addition salts include, for example, salts with mineral acids such as, for example, acetic acid or oxalic acid. Salts describe here also ionic components added to the peptide solution to enhance hydrogel formation and/or mineralization of calcium minerals.

The peptide analogs can also contain non-natural amino acids. Examples of non-natural amino acids include, but are not limited to, sarcosine (Sar), norleucine, ornithine, citrulline, diaminobutyric acid, homoserine, isopropyl Lys, 3-(2'-naphtyl)-Ala, nicotinyl Lys, amino isobutyric acid, and 3-(3'-pyridyl-Ala).

Furthermore, the peptide analogs can contain other derivatized amino acid residues including, but not limited to, methylated amino acids, N-benzylated amino acids, O-benzylated amino acids, N-acetylated amino acids, O-acetylated amino acids, carbobenzoxy-substituted amino acids and the like. Specific examples include, but are not limited to, methyl- Ala (Me Ala), MeTyr, MeArg, MeGlu, MeVal, MeHis, N-acetyl-Lys, O-acetyl-Lys, carbobenzoxy-Lys, Tyr-O-Benzyl, Glu-O-Benzyl, Benzyl-His, Arg-Tosyl, t-butylglycine, t-butylalanine, phenylglycine, cyclohexyl-alanine, and the like.

The invention further includes peptide analogs, which can contain one or more D-isomer forms of the amino acids. Production of retro-inverso D-amino acid peptides where at least one amino acid and perhaps all amino acids are D-amino acids is well known in the art. When all of the amino acids in the peptide are D-amino acids, and the N- and C-terminals of the molecule are reversed, the result is a molecule having the same structural groups being at the same positions as in the L-amino acid form of the molecule. However, the molecule is more stable to proteolytic degradation and is therefore useful in many of the applications recited herein. Diastereomeric peptides may be highly advantageous over all L- or all D-amino acid peptides having the same amino acid sequence because of their higher water solubility, lower immunogenicity, and lower susceptibility to proteolytic degradation. The term "diastereomeric peptide" as used herein refers to a peptide comprising both L-amino acid residues and D-amino acid residues. The number and position of D-amino acid residues in a diastereomeric peptide of the preset invention may be variable so long as the peptide is capable of displaying the function of prolonging the half-life of the chimeric polypeptide.

In one embodiment, the peptide derived from NKp44, comprises an amino acid sequence selected from the group consisting of: SEQ ID NO: 2, SEQ ID NO: 3, SEQ ID NO: 4, and SEQ ID NO: 5. In one embodiment, the peptide derived from NKp44, comprises an amino acid sequence selected from the group consisting of: SEQ ID NO: 3, and SEQ ID NO: 4.

In one embodiment, the peptide derived from NKp44 is glycosylated. In one embodiment, the sequence of the peptide derived from NKp44 comprises at least one glycosylation site, 2 glycosylation sites, 3 glycosylation sites, 4 glycosylation sites, 5 glycosylation sites, 6 glycosylation sites, 7 glycosylation sites, 8 glycosylation sites, 10 glycosylation sites, 11 glycosylation sites, 12 glycosylation sites or 13 glycosylation sites. In one embodiment, the glycosylation site is an "N-linked" glycosylation site and/or "O-linked" glycosylation site.

As used herein, an "N-linked" glycosylation site includes, without limitation, asparagine (Asn) followed by any of X-Serine, X-Threonine and X-Cysteine, wherein X is any amino acid except proline, and glycosylation occurs on the Asn residue. In this invention, the amino acid sequence of any polypeptide situated N-terminal to, C-terminal to, or in between two N-linked sites, can be of any content and length needed to suit a particular design requirement. As used herein, an "O-linked" glycosylation may occur at any serine or threonine residue with no single common core structure or consensus protein sequence.

Proteins of Interest

The "protein of interest" of the invention encompasses proteins, polypeptides, and peptides of any size, structure, or function. In some instances, the polypeptide encoded is smaller than about 50 amino acids and the polypeptide is then termed a peptide. If the polypeptide is a peptide, it will be at least about 2, 3, 4, or at least 5 amino acid residues long. In some embodiments, the protein of interest of the present invention encompasses polypeptide, peptide or protein having a biological function in animals. In some embodiments, the protein of interest of the present invention encompasses peptide or protein having a biological function in mammals. In some embodiments, the protein of interest of the present invention encompasses peptide or protein having a biological function in humans. In some embodiments, the protein of interest of the present invention encompasses any polypeptide, peptide, or protein of biological significance. In some embodiments, the protein of interest encompasses human peptides, synthetic peptides, and/or peptides of non-human source such as an animal. In some embodiments, the protein of interest encompasses human polypeptides, synthetic polypeptides, and/or polypeptides of non-human source such as an animal. Each possibility represents a separate embodiment of the invention. In one embodiment, the protein of interest is a homologue. In one embodiment, a homologue also refers to a deletion, insertion, or substitution variant, including an amino acid substitution, thereof and biologically active polypeptide fragments thereof.

The terms "biological activity", "bioactivity" or "biological function", as used interchangeably herein, are understood as referring to a function that is directly or indirectly performed by the proteins of interest, or by any fragment thereof.

In another embodiment, the protein of interest is a cytokine. In another embodiment, the cytokine is a low molecular weight protein. In another embodiment, a cytokine is a protein secreted by a cell. In another embodiment, a cytokine induces and/or regulates an immune response. In another embodiment, a cytokine has a high affinity binding to a specific receptor or receptors. In another embodiment, cytokines as described herein include mimetics of cytokines that can be used to inhibit or potentiate their effects in vivo. In another embodiment, a cytokine comprises an autocrine activity. In another embodiment, a cytokine comprises a paracrine activity. In another embodiment, a cytokine comprises an endocrine activity. In another embodiment, the cytokine is a Hematopoietin cytokine. In another embodiment, the cytokine is an Interferon cytokine. In another embodiment, the cytokine is a chemokine. In another embodiment, the cytokine is a Tumor Necrosis Factor cytokine. In another embodiment, a cytokine as used herein comprises biological activity and clinical efficacy. In another embodiment, a cytokine as used herein is a therapeutic protein.

In another embodiment, the cytokine of the invention is a cytokine antagonist. In another embodiment, a cytokine antagonist is a cytokine homologue. In another embodiment, a cytokine antagonist is a soluble fragment of a cytokine receptor. In another embodiment, a cytokine antagonist is a chemokine receptor homologue.

In another embodiment, the cytokine as described herein is involved in cytokine signaling cascade comprising Ras-MAP kinase pathway. In another embodiment, a cytokine as described herein is involved in induction of JNK. In another embodiment, a cytokine as described herein is involved in induction of p38MAP. In another embodiment, a cytokine as described herein induces cell proliferation. In another embodiment, a cytokine as described herein is involved in cytokine signaling cascade comprising the JAK/STAT pathway. In another embodiment, a cytokine as described herein induces cell growth inhibition. In another embodiment, a cytokine as described herein induces differentiation.

In another embodiment, a cytokine as described herein is a four α-helix bundle cytokine. In another embodiment, a cytokine as described herein is a long-chain 4-helix bundle cytokine. In another embodiment, a cytokine as described herein is a short-chain 4-helix bundle cytokine.

In another embodiment, a cytokine as described herein is a beta-trefoil cytokine. In another embodiment, a cytokine as described herein is a beta-sandwich cytokine. In another embodiment, a cytokine as described herein is an EGF-like cytokine. In another embodiment, a cytokine as described herein comprises a Cystine knot dimerization domain. In another embodiment, a cytokine as described herein comprises both alpha and beta chains. In another embodiment, a cytokine as described herein is an alpha superfamily cytokine such as IL-2, IL-4, IL-5, GM-CSF, IL-3, IFN-alpha, or IL-13. In another embodiment, a cytokine as described herein is a dimeric 4-helix bundles cytokine. In another embodiment, a cytokine as described herein is a member of the IL family of cytokines.

In another embodiment, a cytokine as described herein is a long-chain 4-helix bundle superfamily cytokine such as GH, G-CSF, Myelomonocytic growth factor, IL-6, IL-3, IL-7, LIF, Oncostatin M, Ciliary neurotrophic factor (CNTF), or cholinergic differentiation factor (CDF). In another embodiment, a cytokine as described herein is a short-chain 4-helix bundle superfamily cytokine such as IL-2, IL-4, IL-13, IFN-alpha, IL-5, GM-CSF, IL-3, or Macrophage colony-stimulating factor (M-CSF). In another embodiment, a cytokine as described herein is a dimeric 4-helix bundles such as IFN-Gamma, IL-10, or IFN-Beta.

In another embodiment, a cytokine as described herein is a Beta-Trefoil cytokine such as IL1-A, IL1-B, or FGF. In another embodiment, a cytokine as described herein is a Beta-sandwich cytokine such as TNF-alpha or TNF-Beta. In another embodiment, a cytokine as described herein is an EGF-like cytokine such as TGF-Alpha. In another embodiment, a cytokine as described herein comprises cystine knot dimerization domains. In another embodiment, Gonadotropin, Nerve Growth Factor (NGF), Platelet-derived growth factor (PDGF), and TGF-Beta2 comprise cystine knot dimerization domains. In another embodiment, a cytokine as described herein comprises both alpha and beta chains. In another embodiment, IL-8, IP10, platelet factor 4 (PF-4), bTG, GRO, 9E3, HLA-A2, macrophage inflammatory protein 1 alpha (MIP-1 alpha), macrophage inflammatory protein 1 beta (MIP-1 beta), and Melanoma growth stimulating activity (MGSA) comprise both alpha and beta chains.

In another embodiment, a cytokine as described herein binds a hematopoietin-receptor family member (also called the class I cytokine receptor family). In another embodiment, a cytokine as described herein binds a class II cytokine receptor (interferons or interferon-like cytokines). In another embodiment, a cytokine as described herein binds a tumor necrosis factor-receptor (TNFR). In another embodiment, a cytokine as described herein binds a chemokine receptor. In another embodiment, a cytokine as described herein binds a G protein-coupled receptor.

In another embodiment, a cytokine as described herein is a growth hormone (GH). In another embodiment, a cytokine as described herein is a human growth hormone (hGH) (Genbank Accession No: P01241). In one embodiment, "human growth hormone" (hGH) refers to a polypeptide, such as that set forth in Genbank Accession No. P01241, exhibiting hGH activity (i.e. stimulation of growth). In one embodiment, an hGH of the present invention also refers to homologues.

In another embodiment, a cytokine as described herein is a member of the superfamily of growth hormone (GH)-like cytokines. In another embodiment, a cytokine as described herein is close to the cluster formed by ciliary neurotrophic factor and granulocyte colony-stimulating factor (CSF).

In another embodiment, a cytokine as described herein enhances cytokine responses, type 1 (IFN-γ, TGF-β etc.). In another embodiment, a cytokine as described herein enhances antibody responses, type 2 (IL-4, IL-10, IL-13, etc.).

In another embodiment, a cytokine as described herein is a Chorionic Gonadotropin (CG). In another embodiment, a cytokine as described herein is a human Chorionic Gonadotropin (hCG). In another embodiment, a cytokine as described herein is. In another embodiment, a cytokine as described herein is. In another embodiment, a cytokine as described herein is. In another embodiment, a cytokine as described herein is a protease. In another embodiment, a cytokine as described herein is a serine protease. In another embodiment, a cytokine as described herein is a factor VII. In another embodiment, a cytokine as described herein is a recombinant factor VIIa.

In another embodiment, a cytokine as described herein is a peptide. In another embodiment, the cytokine is glycosylated.

In some embodiments, the proteins of interest, are protein, polypeptides or peptide hormones. The term "protein, polypeptide or peptide hormones" refers to a class of peptides that are secreted into the blood stream and have endocrine functions in living animals (e.g., humans). In some embodiments, the peptide hormones are signaling molecules, carried by body fluid such as blood to organs and tissues of the body to exert their functions. Typically, there are many types of hormones that act on different aspects of bodily functions and processes.

In another embodiment, the protein of interest is an antibody. In one embodiment, the antibody a single chain antibody. In another embodiment, at least one peptide derived from NKp44 (e.g., SEQ ID NO: 3, or SEQ ID NO: 4) is inserted between the heavy and light chain of a single chain antibody.

Peptide hormones may be secreted from glands such as the pituitary gland including the anterior pituitary gland (e.g., prolactin (PRL), adrenocorticotrophichormone (ACTH), and growth hormone (GH), follicle stimulating hormone (FSH), luteinizing hormone (LH), and thyroid stimulating hormone (TSH)), and the posterior pituitary gland (e.g., antidiuretic hormone, also called vasopressin, and oxytocin), the thyroid gland (e.g., calcitonin), the parathyroid gland (e.g., parathyroid hormone), alternatively peptide hormones may be secreted by the pancreas (e.g., glucagon, somatostatin, and insulin), or alternatively produced by many different organs and tissues, such as the heart (e.g., atrial-natriuretic peptide (ANP) or atrial natriuretic factor (ANF)), the gastrointestinal tract (e.g., cholecystokinin, gastrin), and adipose tissue stores (e.g., leptin), as well as by the placenta (e.g., chorionic gonadotropin).

In some embodiments, peptide hormones of the invention include without limitation: Insulin, Glucagon, Gonadotropin (FSH, LH, CG), human Thyroid Stimulating Hormone, angiotensin II, basic fibroblast growth factor-2, parathyroid hormone-related protein, vasopressin, oxytocin, atrial-natriuretic peptide (ANP) or atrial natriuretic factor (ANF), somatostatin, cholecystokinin, gastrin, and adipose tissue stores (leptin). In another embodiment, the protein of interest is a hormone such as HCG-β and GH.

In some embodiments, the proteins of interest of the invention are peptides hormones of the Somatotropin family. As used herein "Somatotropin family" is a protein family which includes somatotropin (growth hormone (GH)), choriomammotropin (lactogen), prolactin, placental prolactin-related proteins, proliferin, proliferin related protein, and somatolactin from various fishes.

In some embodiments, the proteins of interest of the invention are peptides of the secretin family. As used herein the secretin family is a family of evolutionarily related peptide hormones that regulate activity of G-protein coupled receptors from secretin receptor family. A number of polypeptidic hormones, mainly expressed in the intestine or the pancreas, belong to a group of these structurally related peptides include, but not limited to, Glucagon, gastric inhibitory polypeptide (GIP), secretin, vasoactive intestinal peptide (VIP), Pituitary adenylate cyclase-activating polypeptide (PACAP), and Growth hormone-releasing hormone (GHRH).

In some embodiments, the protein of interest is a glucagon-like peptide-1 (GLP-1). In one embodiment, "glucagon-like peptide-1" (GLP-1) refers to a mammalian polypeptide. In one embodiment, "glucagon-like peptide-1" (GLP-1) refers to a human polypeptide. In some embodiments, GLP-1 is cleaved from the glucagon preproprotein (Genbank accession No: NP002045) that has the ability to bind to the GLP-1 receptor and initiate a signal transduction pathway resulting in insulinotropic activity. In one embodiment, "insulinotropic activity" refers to the ability to stimulate insulin secretion in response to elevated glucose levels, thereby causing glucose uptake by cells and decreased plasma glucose levels. In some embodiments, GLP-1 polypeptides include, but are not limited to those described in U.S. Pat. No. 5,118,666; which is incorporated by reference herein. In some embodiments, the cytokine is a glucagon-like peptide-1 agonist (GLP-1 agonist). In some embodiments, the GLP-1 agonist is Exenatide.

In some embodiments, protein of interest of the invention is a human "reproductive" hormone. As used herein a human "reproductive" hormone represents a group of hormones, consisting of a subunits which are identical among the group, and β subunits which differ according to the member of the group. The human "reproductive" hormone include: human chorionic gonadotropin (HCG), follicle stimulating hormone (FSH), luteinizing hormone (LH) and thyroid stimulating hormone (TSH).

Chimeras of the Invention

In some embodiments, the chimera comprises a protein of interest and at least one peptide derived from NKp44 attached to its amino terminus and/or a carboxy terminus. In one aspect, the invention provides a chimera comprising: a protein of interest or an active fragment thereof and at least one peptide derived from NKp44. In one embodiment, the at least one peptide is attached to an amino terminus, a carboxy terminus, or both the amino and the carboxy terminuses of the protein of interest. In one embodiment, the at least one peptide derived from NKp44 is attached to an amino terminus of the protein of interest. In one embodiment, the at least one peptide derived from NKp44 is attached to a carboxy terminus of the protein of interest. In one embodiment, at least one peptide derived from NKp44 is attached to the amino terminus and to the carboxy terminus of the protein of interest. In one embodiment, at least two peptides derived from NKp44 are attached to the amino terminus and/or to the carboxy terminus of the protein of interest. In one embodiment, at least two peptides derived from NKp44 are attached to both the amino terminus and to the carboxy terminus of the protein of interest. In one embodiment, at least three peptides derived from NKp44 are attached to the amino terminus and/or to the carboxy terminus of the protein of interest. In some embodiments, at least one peptide derived from NKp44 is attached to the amino terminus of the peptide of interest and at least one peptide derived from NKp44 is attached to the carboxy terminus of the peptide of interest. In some embodiments, the peptide derived from NKp44 is attached to the carboxy terminus and/or the amino terminus of the protein of interest in tandem repeats (i.e., two or more contiguous repeats).

In some embodiments, the chimera comprises at least one peptide derived from NKp44 located between a first and a second portions of the protein of interest. As used herein the term "portion" refers to a fragment of contiguous amino acid residues of the protein of interest. As used herein, the first and the second portions refers to portions of the protein of interest which together, constitute the entire protein of interest, or alternatively a biologically active fragment thereof In some embodiments, the chimera comprises the formula $X_1$-$X_2$-$X_3$, wherein $X_1$ is a first portion of the peptide of interest (optionally, a signal peptide), $X_2$ is the NKp44 derived peptide described herein, and $X_3$ is a second portion of the peptide of interest. For a non-limiting example, wherein the peptide of interest is hGH, $X_1$ represents amino acids 1-87 of hGH and $X_3$ represents amino acid 88-217 of hGH. In yet another non-limiting example wherein the peptide of interest is hGH, $X_1$ represents amino acids 1-175 of hGH and $X_3$ represents amino acid 176-217 of hGH.

In some embodiments, the chimera comprises at least one peptides derived from NKp44 located between a first and a second part of the protein of interest and at least one peptide derived from NKp44 attached to the amino terminus and/or to the carboxy terminus of the protein of interest. In some embodiments, the chimera comprises a formula selected from the group consisting of: $X_2$-$X_1$-$X_2$-$X_3$, $X_2$-$X_2$-$X_1$-$X_2$-$X_3$, $X_2$-$X_1$-$X_2$-$X_2$-$X_3$, $X_2$-$X_2$-$X_1$-$X_2$-$X_2$-$X_3$, $X_1$-$X_2$- $X_3$-$X_2$, $X_2$-$X_2$-$X_3$-$X_2$-$X_2$, $X_1$-$X_2$-$X_2$-$X_3$-$X_2$, $X_1$-$X_2$-$X_2$-$X_3$-$X_2$-$X_2$, $X_2$-$X_1$-$X_2$-$X_3$-$X_2$, $X_2$-$X_2$-$X_1$-$X_2$- $X_3$-$X_2$, $X_2$-$X_2$-$X_1$-$X_2$-$X_3$-$X_2$, $X_2$-$X_1$-$X_2$-$X_3$-$X_2$-$X_2$, $X_2$-$X_1$-$X_2$-$X_2$-$X_3$-$X_2$, $X_2$-$X_2$- $X_1$-$X_2$-$X_2$-$X_3$-$X_2$, $X_2$-$X_1$-$X_2$-$X_2$-$X_3$-$X_2$-$X_2$, and $X_2$-$X_2$-$X_1$- $X_2$-$X_2$-$X_3$-$X_2$-$X_2$. In some embodiments, $X_1$ is a first part of the peptide of interest, $X_2$ represents the NKp44 derived peptide described herein, and $X_3$ is a second part of the peptide of interest. In some embodiments, $X_1$ is a first part of the peptide of interest, each of the $X_2$ is independently selected from any of the NKp44 derived peptide described herein, and $X_3$ is a second part of the peptide of interest.

In some embodiments, the protein of interest comprises at least two subunits (e.g., hCG). In said embodiments, the at least one peptide derived from NKp44 may be linked to the N and/or C terminus of each subunit. In said embodiments, the at least one peptide derived from NKp44 may be further linked to the N and/or C terminus of each subunit. In some embodiments, the at least one peptide derived from NKp44 is further attached to the amino terminus and/or to the carboxy terminus of the protein of interest.

In some embodiments, the peptide derived from NKp44 is attached to at least one position selected from the group consisting of: the amino terminus of the protein of interest, the carboxy terminus of the protein of interest, and between a first and a second portions of the protein of interest.

In another embodiment, the chimera comprises a cytokine or an active fragment thereof and a peptide derived from NKp44. In another embodiment, the chimera comprises a hormone or an active fragment thereof and a peptide derived from NKp44. In one embodiment, the peptide derived from NKp44 comprises amino acid sequence as set forth in SEQ ID NO: 2. In one embodiment, the peptide derived from NKp44 comprises amino acid sequence as set forth in SEQ ID NO: 3. In one embodiment, the peptide derived from NKp44 comprises amino acid sequence as set forth in SEQ ID NO: 4. In one embodiment, the peptide derived from NKp44 comprises amino acid sequence as set forth in SEQ ID NO: 5.

In some embodiments, the chimera comprises a protein of interest attached to one or more peptides selected from the peptides comprising amino acid sequences consisting of: SEQ ID NO: 2, SEQ ID NO: 3, SEQ ID NO: 4, and SEQ ID NO: 5. In some embodiments, the chimera comprises a protein of interest attached to at least two polypeptides selected from the group consisting of: SEQ ID NO: 2, SEQ ID NO: 3, SEQ ID NO: 4, and SEQ ID NO: 5. In some embodiments, the chimera comprises a protein of interest attached to at least two polypeptides comprising SEQ ID NO: 2 and a peptide selected from the group consisting of: SEQ ID NO: 2, SEQ ID NO: 3, SEQ ID NO: 4, and SEQ ID NO: 5. In some embodiments, the chimera comprises a protein of interest attached to at least two polypeptides comprising SEQ ID NO: 3 and a peptide selected from the group consisting of: SEQ ID NO: 2, SEQ ID NO: 3, SEQ ID NO: 4, and SEQ ID NO: 5. In some embodiments, the chimera comprises a protein of interest attached to at least two polypeptides comprising SEQ ID NO: 4 and a peptide selected from the group consisting of: SEQ ID NO: 2, SEQ ID NO: 3, SEQ ID NO: 4, and SEQ ID NO: 5. In some embodiments, the chimera comprises a protein of interest attached to at least two polypeptides comprising SEQ ID NO: 5 and a peptide selected from the group consisting of: SEQ ID NO: 2, SEQ ID NO: 3, SEQ ID NO: 4, and SEQ ID NO: 5.

In some embodiments, the chimera comprises a peptide comprising the amino acid sequence as set forth in SEQ ID NO: 2 attached to the amino terminus of the protein of interest. In some embodiments, the chimera comprises a peptide comprising the amino acid sequence as set forth in SEQ ID NO: 2 attached to the carboxy terminus of the protein of interest. In some embodiments, the chimera comprises a peptide comprising the amino acid sequence as set forth in SEQ ID NO: 2 attached to the amino terminus of the protein of interest and a peptide comprising the amino acid sequence as set forth in SEQ ID NO: 2 attached to the carboxy terminus of the protein of interest. In some embodiments, the chimera comprises a peptide comprising the amino acid sequence as set forth in SEQ ID NO: 2 attached to the amino terminus of the protein of interest between a first and a second portions of the protein of interest. In some embodiments, the chimera comprises a peptide comprising the amino acid sequence as set forth in SEQ ID NO: 2 attached between a first and a second portions of the protein of interest and further attached in a position selected from the group consisting of: the amino terminus of the protein of interest and the carboxy terminus of the protein of interest. In some embodiments, the chimera comprises a peptide comprising the amino acid sequence as set forth in SEQ ID NO: 3 attached to the amino terminus of the protein of interest. In some embodiments, the chimera comprises a peptide comprising the amino acid sequence as set forth in SEQ ID NO: 3 attached to the carboxy terminus of the protein of interest. In some embodiments, the chimera comprises a peptide comprising the amino acid sequence as set forth in SEQ ID NO: 3 attached to the amino terminus of the protein of interest and a peptide comprising the amino acid sequence as set forth in SEQ ID NO: 3 attached to the carboxy terminus of the protein of interest. In some embodiments, the chimera comprises a peptide comprising the amino acid sequence as set forth in SEQ ID NO: 3 attached to the amino terminus of the protein of interest between a first and a second portions of the protein of interest. In some embodiments, the chimera comprises a peptide comprising the amino acid sequence as set forth in SEQ ID NO: 3 attached between a first and a second portions of the protein of interest and further attached in a position selected from the group consisting of: the amino terminus of the protein of interest and the carboxy terminus of the protein of interest. In some embodiments, the chimera comprises a peptide comprising the amino acid sequence as set forth in SEQ ID NO: 4 attached to the amino terminus of the protein of interest. In some embodiments, the chimera comprises a peptide comprising the amino acid sequence as set forth in SEQ ID NO: 4 attached to the carboxy terminus of the protein of interest. In some embodiments, the chimera comprises a peptide comprising the amino acid sequence as set forth in SEQ ID NO: 4 attached to the amino terminus of the protein of interest and a peptide comprising the amino acid sequence as set forth in SEQ ID NO: 4 attached to the carboxy terminus of the protein of interest. In some embodiments, the chimera comprises a peptide comprising the amino acid sequence as set forth in SEQ ID NO: 4 attached to the amino terminus of the protein of interest between a first and a second portions of the protein of interest. In some embodiments, the chimera comprises a peptide comprising the amino acid sequence as set forth in SEQ ID NO: 4 attached between a first and a second portions of the protein of interest and further attached in a position selected from the group consisting of: the amino terminus of the protein of interest and the carboxy terminus of the protein of interest. In some embodiments, the chimera comprises a peptide comprising the amino acid sequence as set forth in SEQ ID NO: 5 attached to the amino terminus of the protein of interest. In some embodiments, the chimera comprises a peptide comprising the amino acid sequence as set forth in SEQ ID NO: 5 attached to the carboxy terminus of the protein of interest. In some embodiments, the chimera comprises a peptide comprising the amino acid sequence as set forth in SEQ ID NO: 5 attached to the amino terminus of the protein of interest and a peptide comprising the amino acid sequence as set forth in SEQ ID NO: 5 attached to the carboxy terminus of the protein of interest. In some embodiments, the chimera comprises a peptide comprising the amino acid sequence as set forth in SEQ ID NO: 5 attached to the amino terminus of the protein of interest between a first and a second portions of the protein of interest. In some embodiments, the chimera comprises a peptide comprising the amino acid sequence as set forth in SEQ ID NO: 5 attached between a first and a second portions of the protein of interest and further attached in a position selected from the group consisting of: the amino terminus of the protein of interest and the carboxy terminus of the protein of interest.

In some embodiments, the chimera comprises one or more peptides selected from the peptides comprising amino acid sequences consisting of: SEQ ID NO: 2, SEQ ID NO: 3, SEQ ID NO: 4, and SEQ ID NO: 5 attached between a first and a second portions of the protein of interest and/or to the amino terminus of the protein of interest and/or to the carboxy terminus of the protein of interest. In some embodiments, the chimera comprises one or more peptides selected from the peptides comprising amino acid sequences consisting of: SEQ ID NO: 2, SEQ ID NO: 3, SEQ ID NO: 4, and SEQ ID NO: 5 attached between a first and a second portions of the protein of interest and further attached in a position selected from the group consisting of: the amino terminus of the protein of interest and the carboxy terminus of the protein of interest.

In another embodiment, the peptide derived from NKp44 is attached to the protein of interest via a linker. In another embodiment, the linker is a covalent bond. In another embodiment, the linker is a peptide bond. In another embodiment, the linker is a substituted peptide bond. In some embodiments, the linker is an amino acid or a plurality of amino acids.

In some embodiments, the chimera further comprises a leader peptide. As used herein, the term "leader peptide" refers to a sequence located at the amino terminal end of a precursor form of a protein (e.g., the chimera of the present invention), ensuring entry into the secretory pathway. Typically, leader peptide sequence is cleaved off during maturation. In another embodiment, the chimera further comprises a leader peptide to direct the expressed chimera across the membrane of the endoplasmic reticulum (ER). In some embodiments, the leader peptide is attached to the amino terminus of the protein of interest. In some embodiments, the leader peptide is attached to the amino terminus of the peptide derived from NKp44. In some embodiments, the leader peptide comprises the amino acid sequence as set forth in SEQ ID NO: 8. In some embodiments, the leader peptide comprises the amino acid sequence as set forth in SEQ ID NO: 17.

In some embodiments, the chimera further comprises a tag. As used herein the term "tag" refers to a peptide sequence added to the chimera to facilitate detection and/or purification of the chimera. Non-limiting examples of commercially available tags include: FLAG peptide, a His-tag comprising histidine repeats, Glutathion-S-Transferase (GST), Staphylococcal protein A, Streptococcal protein G, β-galactosidase, Streptavidin, c-Myc, and Green Fluorescent Protein. In some embodiments, the tag is a His-tag comprising histidine repeats. In some embodiments, His tag comprises at least 2, 3, 4, 5, 6, 7, 8, 9, 10, 11, or 12 histidine repeats. In some embodiments, the tag comprises the amino acid sequence as set forth in SEQ ID NO: 7. In other embodiments, the tag comprises the amino acid sequence as set forth in SEQ ID NO: 6. In other embodiments, the tag comprises the amino acid sequence as set forth in SEQ ID NO: 18.

In some embodiments, the chimera comprises the protein of interest in its native form. Alternatively, in other embodiments, the chimera comprises a fragment or a truncated form of the protein of interest. In one embodiment, a protein of interest of the present invention is at least 50%, 60%, 70%, 80%, 90%, 95% homologous to the native protein of interest. Each possibility represents a separate embodiment of the instant invention. In some embodiments, the chimera comprises or consists of a sequence selected from the sequences denoted in Table 1.

TABLE 1

Amino acid sequences of chimeras of the invention

| SEQ ID NO: | Description | Sequence |
|---|---|---|
| 13 | hCG-β-strep tag (SEQ ID NO: 12) linked to a peptide derived from NKp44 (SEQ ID NO: 2) | MEMFQGLLLLLLLSMGGTWASKEP*WSHPQFEK*LRPRCR PINATLAVEKEGCPVCITVNTTICAGYCPTMTRVLQGVL PALPQVVCNYRDVRFESIRLPGCPRGVNPVVSYAVALS CQCALCRRSTTDCGGPKDHPLTCDDPRFQDSPASASTQ TSWTPRDLVSSQTQTQSCVPPTAGARQAPESPSTIPV PSHPSSPLPVPLPSRPQNSTLRPGP |
| 14 | hCG-β (without the leader peptide) linked to a peptide derived from NKp44 (SEQ ID NO: 2) | LRPRCRPINATLAVEKEGCPVCITVNTTICAGYCPTMTR VLQGVLPALPQVVCNYRDVRFESIRLPGCPRGVNPVVS YAVALSCQCALCRRSTTDCGGPKDHPLTCDDPRFQDSP ASASTQTSWTPRDLVSSQTQTQSCVPPTAGARQAPES PSTIPVPSHPSSPLPVPLPSRPQNSTLRPGP |
| 21 | hGH (SEQ ID NO: 15) having a peptide derived from NKp44 (SEQ ID NO: 2) and a His tag (SEQ ID NO: 7) attached to its carboxy terminus. | FPTIPLSRLFDNAMLRAHRLHQLAFDTYQEFEEAYIPKE QKYSFLQNPQTSLCFSESIPTPSNREETQQKSNLELLRISL LLIQSWLEPVQFLRSVFANSLVYGASDSNVYDLLKDLEE GIQTLMGRLEDGSPRTGQIFKQTYSKFDTNSHNDDALL KNYGLLYCFRKDMDKVETFLRIVQCRSVEGSCGFSPAS ASTQTSWTPRDLVSSQTQTQSCVPPTAGARQAPESPS TIPVPSHPSSPLPVPLPSRPQNSTLRPGPHHHHHHHH |
| 22 | hGH (SEQ ID NO: 15) linked to a peptide derived from NKp44 (SEQ ID NO: 2) | SPASASTQTSWTPRDLVSSQTQTQSCVPPTAGARFPTI PLSRLFDNAMLRAHRLHQLAFDTYQEFEEAYIPKEQKY SFLQNPQTSLCFSESIPTPSNREETQQKSNLELLRISLLLIQ SWLEPVQFLRSVFANSLVYGASDSNVYDLLKDLEEGIQ TLMGRLEDGSPRTGQIFKQTYSKFDTNSHNDDALLKNY GLLYCFRKDMDKVETFLRIVQCRSVEGSCGF |
| 23 | hGH (SEQ ID NO: 16) linked to a peptide derived from NKp44 (SEQ ID NO: 2) | FPTIPLSRLFDNAMLRAHRLHQLAFDTYQEFEEAYIPKE QKYSFLQNPQTSLCFSESIPTPSNREETQQKSNLELLRISL LLIQSWLEPVQFLRSVFANSLVYGASDSNVYDLLKDLEE GIQTLMGRLEDGSPRTGQIFKQTYSKFDTNSHNDDALL KNYGLLYCFRKDMDKVETFLRIVQCRSVEGSCGFSPAS ASTQTSWTPRDLVSSQTQTQSCVPPTAGARQAPESPS TIPVPSHPSSPLPVPLPSRPQNSTLRPGP |

TABLE 1-continued

Amino acid sequences of chimeras of the invention

| SEQ ID NO: | Description | Sequence |
|---|---|---|
| 24 | hGH (SEQ ID NO: 19) linked to a peptide derived from NKp44 (SEQ ID NO: 5) and His tag (SEQ ID NO:7) | MATGSRTSLLLAFGLLCLPWLQEGSADYKDHDGDYKD HDIDYKDDDDKFPTIPLSRLFDNAMLRAHRLHQLAFDT YQEFEEAYIPKEQKYSFLQNPQTSLCFSESIPTPSNREETQ QKSNLELLRISLLLIQSWLEPVQFLRSVFANSLVYGASDS NVYDLLKDLEEGIQTLMGRLEDGSPRTGQIFKQTYSKFD TNSHNDDALLKNYGLLYCFRKDMDKVETFLRIVQCRSV EGSCGFSPASASTQTSWTPRDLVSSQTQTQSCVPPTA GARQAPESPSTIPVPSHPSSPLPVPLPSRPQASTLRPGP HHHHHHHH |
| 25 | hGH (SEQ ID NO: 19) linked to a peptide derived from NKp44 (SEQ ID NO: 5) | MATGSRTSLLLAFGLLCLPWLQEGSADYKDHDGDYKD HDIDYKDDDDKFPTIPLSRLFDNAMLRAHRLHQLAFDT YQEFEEAYIPKEQKYSFLQNPQTSLCFSESIPTPSNREETQ QKSNLELLRISLLLIQSWLEPVQFLRSVFANSLVYGASDS NVYDLLKDLEEGIQTLMGRLEDGSPRTGQIFKQTYSKFD TNSHNDDALLKNYGLLYCFRKDMDKVETFLRIVQCRSV EGSCGFSPASASTQTSWTPRDLVSSQTQTQSCVPPTA GARQAPESPSTIPVPSHPSSPLPVPLPSRPQASTLRPGP |
| 26 | A peptide derived from NKp44 (SEQ ID NO: 5) attached to the carboxy terminus of hGH (SEQ ID NO: 16). | FPTIPLSRLFDNAMLRAHRLHQLAFDTYQEFEEAYIPKE QKYSFLQNPQTSLCFSESIPTPSNREETQQKSNLELLRISL LLIQSWLEPVQFLRSVFANSLVYGASDSNVYDLLKDLEE GIQTLMGRLEDGSPRTGQIFKQTYSKFDTNSHNDDALL KNYGLLYCFRKDMDKVETFLRIVQCRSVEGSCGFSPAS ASTQTSWTPRDLVSSQTQTQSCVPPTAGARQAPESPS TIPVPSHPSSPLPVPLPSRPQASTLRPGP |
| 27 | hGH (SEQ ID NO: 16) having a leader peptide (SEQ ID NO: 17) and a peptide derived from NKp44 (SEQ ID NO: 3) attached to its amino terminus, a peptide derived from NKp44 (SEQ ID NO: 3) attached to its carboxy terminus, and a His tag (SEQ ID NO: 7) attached to its carboxy terminus. | MATGSRTSLLLAFGLLCLPWLQEGSASPASASTQTSWT PRDLVSSQTQTQSCVPPTAGARFPTIPLSRLFDNAMLR AHRLHQLAFDTYQEFEEAYIPKEQKYSFLQNPQTSLCFS ESIPTPSNREETQQKSNLELLRISLLLIQSWLEPVQFLRSV FANSLVYGASDSNVYDLLKDLEEGIQTLMGRLEDGSPR TGQIFKQTYSKFDTNSHNDDALLKNYGLLYCFRKDMD KVETFLRIVQCRSVEGSCGFSPASASTQTSWTPRDLVSS QTQTQSCVPPTAGARHHHHHHHH |
| 28 | hGH (SEQ ID NO: 16) having a leader peptide (SEQ ID NO: 17) and a peptide derived from NKp44 (SEQ ID NO: 3) attached to its amino terminus, and a peptide derived from NKp44 (SEQ ID NO: 3) attached to its carboxy terminus. | MATGSRTSLLLAFGLLCLPWLQEGSASPASASTQTSWT PRDLVSSQTQTQSCVPPTAGARFPTIPLSRLFDNAMLR AHRLHQLAFDTYQEFEEAYIPKEQKYSFLQNPQTSLCFS ESIPTPSNREETQQKSNLELLRISLLLIQSWLEPVQFLRSV FANSLVYGASDSNVYDLLKDLEEGIQTLMGRLEDGSPR TGQIFKQTYSKFDTNSHNDDALLKNYGLLYCFRKDMD KVETFLRIVQCRSVEGSCGFSPASASTQTSWTPRDLVSS QTQTQSCVPPTAGAR |
| 29 | A peptide derived from NKp44 (SEQ ID NO: 3) attached to the amino terminus and the carboxy terminus of hGH (SEQ ID NO: 16) | SPASASTQTSWTPRDLVSSQTQTQSCVPPTAGARFPTI PLSRLFDNAMLRAHRLHQLAFDTYQEFEEAYIPKEQKY SFLQNPQTSLCFSESIPTPSNREETQQKSNLELLRISLLLIQ SWLEPVQFLRSVFANSLVYGASDSNVYDLLKDLEEGIQ TLMGRLEDGSPRTGQIFKQTYSKFDTNSHNDDALLKNY GLLYCFRKDMDKVETFLRIVQCRSVEGSCGFSPASAST QTSWTPRDLVSSQTQTQSCVPPTAGAR |
| 30 | hGH (SEQ ID NO: 15) having a peptide derived from NKp44 (SEQ ID NO: 3) and a His tag (SEQ ID NO: 7) attached to its carboxy terminus. | MATGSRTSLLLAFGLLCLPWLQEGSAFPTIPLSRLFDNA MLRAHRLHQLAFDTYQEFEEAYIPKEQKYSFLQNPQTS LCFSESIPTPSNREETQQKSNLELLRISLLLIQSWLEPVQF LRSVFANSLVYGASDSNVYDLLKDLEEGIQTLMGRLED GSPRTGQIFKQTYSKFDTNSHNDDALLKNYGLLYCFRK DMDKVETFLRIVQCRSVEGSCGFSPASASTQTSWTPRD LVSSQTQTQSCVPPTAGARHHHHHHHH |
| 31 | hGH (SEQ ID NO: 15) having a peptide derived from NKp44 (SEQ ID NO: 3) attached to its carboxy terminus. | MATGSRTSLLLAFGLLCLPWLQEGSAFPTIPLSRLFDNA MLRAHRLHQLAFDTYQEFEEAYIPKEQKYSFLQNPQTS LCFSESIPTPSNREETQQKSNLELLRISLLLIQSWLEPVQF LRSVFANSLVYGASDSNVYDLLKDLEEGIQTLMGRLED GSPRTGQIFKQTYSKFDTNSHNDDALLKNYGLLYCFRK DMDKVETFLRIVQCRSVEGSCGFSPASASTQTSWTPRD LVSSQTQTQSCVPPTAGAR |

TABLE 1-continued

Amino acid sequences of chimeras of the invention

| SEQ ID NO: | Description | Sequence |
|---|---|---|
| 32 | hGH (SEQ ID NO: 16) having a peptide derived from NKp44 (SEQ ID NO: 3) attached to its carboxy terminus. | FPTIPLSRLFDNAMLRAHRLHQLAFDTYQEFEEAYIPKE QKYSFLQNPQTSLCFSESIPTPSNREETQQKSNLELLRISL LLIQSWLEPVQFLRSVFANSLVYGASDSNVYDLLKDLEE GIQTLMGRLEDGSPRTGQIFKQTYSKFDTNSHNDDALL KNYGLLYCFRKDMDKVETFLRIVQCRSVEGSCGFSPAS ASTQTSWTPRDLVSSQTQTQSCVPPTAGAR |
| 33 | hGH (SEQ ID NO: 15) having a peptide derived from NKp44 (SEQ ID NO: 4) and a His tag (SEQ ID NO: XX) attached to its carboxy terminus. | MATGSRTSLLLAFGLLCLPWLQEGSAFPTIPLSRLFDNA MLRAHRLHQLAFDTYQEFEEAYIPKEQKYSFLQNPQTS LCFSESIPTPSNREETQQKSNLELLRISLLLIQSWLEPVQF LRSVFANSLVYGASDSNVYDLLKDLEEGIQTLMGRLED GSPRTGQIFKQTYSKFDTNSHNDDALLKNYGLLYCFRK DMDKVETFLRIVQCRSVEGSCGFQAPESPSTIPVPSHPS SPLPVPLPSRPQNSTLRPGPHHHHHHHH |
| 34 | hGH (SEQ ID NO: 15) having a peptide derived from NKp44 (SEQ ID NO: 4) attached to its carboxy terminus. | MATGSRTSLLLAFGLLCLPWLQEGSAFPTIPLSRLFDNA MLRAHRLHQLAFDTYQEFEEAYIPKEQKYSFLQNPQTS LCFSESIPTPSNREETQQKSNLELLRISLLLIQSWLEPVQF LRSVFANSLVYGASDSNVYDLLKDLEEGIQTLMGRLED GSPRTGQIFKQTYSKFDTNSHNDDALLKNYGLLYCFRK DMDKVETFLRIVQCRSVEGSCGFQAPESPSTIPVPSHPS SPLPVPLPSRPQNSTLRPGP |
| 35 | hGH (SEQ ID NO: 16) having a peptide derived from NKp44 (SEQ ID NO: 4) attached to its carboxy terminus. | FPTIPLSRLFDNAMLRAHRLHQLAFDTYQEFEEAYIPKE QKYSFLQNPQTSLCFSESIPTPSNREETQQKSNLELLRISL LLIQSWLEPVQFLRSVFANSLVYGASDSNVYDLLKDLEE GIQTLMGRLEDGSPRTGQIFKQTYSKFDTNSHNDDALL KNYGLLYCFRKDMDKVETFLRIVQCRSVEGSCGFQAPE SPSTIPVPSHPSSPLPVPLPSRPQNSTLRPGP |
| 36 | hGH (SEQ ID NO: 16) having a leader peptide (SEQ ID NO: 17) and a peptide derived from NKp44 (SEQ ID NO: 3) attached to its amino terminus, and peptide derived from NKp44 (SEQ ID NO: 4) and a His tag (SEQ ID NO: 7) attached to its carboxy terminus. | MATGSRTSLLLAFGLLCLPWLQEGSASPASASTQTSWT PRDLVSSQTQTQSCVPPTAGARFPTIPLSRLFDNAMLR AHRLHQLAFDTYQEFEEAYIPKEQKYSFLQNPQTSLCFS ESIPTPSNREETQQKSNLELLRISLLLIQSWLEPVQFLRSV FANSLVYGASDSNVYDLLKDLEEGIQTLMGRLEDGSPR TGQIFKQTYSKFDTNSHNDDALLKNYGLLYCFRKDMD KVETFLRIVQCRSVEGSCGFQAPESPSTIPVPSHPSSPLP VPLPSRPQNSTLRPGPHHHHHHHH |
| 37 | hGH (SEQ ID NO: 16) having a leader peptide (SEQ ID NO: 17) and a peptide derived from NKp44 (SEQ ID NO: 3) attached to its amino terminus, and peptide derived from NKp44 (SEQ ID NO: 4) attached to its carboxy terminus. | MATGSRTSLLLAFGLLCLPWLQEGSASPASASTQTSWT PRDLVSSQTQTQSCVPPTAGARFPTIPLSRLFDNAMLR AHRLHQLAFDTYQEFEEAYIPKEQKYSFLQNPQTSLCFS ESIPTPSNREETQQKSNLELLRISLLLIQSWLEPVQFLRSV FANSLVYGASDSNVYDLLKDLEEGIQTLMGRLEDGSPR TGQIFKQTYSKFDTNSHNDDALLKNYGLLYCFRKDMD KVETFLRIVQCRSVEGSCGFQAPESPSTIPVPSHPSSPLP VPLPSRPQNSTLRPGP |
| 38 | hGH (SEQ ID NO: 16) having a peptide derived from NKp44 (SEQ ID NO: 3) attached to its amino terminus, and peptide derived from NKp44 (SEQ ID NO: 4) attached to its carboxy terminus. | SPASASTQTSWTPRDLVSSQTQTQSCVPPTAGARFPTI PLSRLFDNAMLRAHRLHQLAFDTYQEFEEAYIPKEQKY SFLQNPQTSLCFSESIPTPSNREETQQKSNLELLRISLLLIQ SWLEPVQFLRSVFANSLVYGASDSNVYDLLKDLEEGIQ TLMGRLEDGSPRTGQIFKQTYSKFDTNSHNDDALLKNY GLLYCFRKDMDKVETFLRIVQCRSVEGSCGFQAPESPS TIPVPSHPSSPLPVPLPSRPQNSTLRPGP |
| 39 | hGH (SEQ ID NO: 15) having a leader peptide (SEQ ID NO: 17) and a peptide derived from NKp44 (SEQ ID NO: 4) attached to its amino terminus, and peptide derived from NKp44 (SEQ ID NO: 3) and a His tag (SEQ ID NO: 7) attached to its carboxy terminus. | MATGSRTSLLLAFGLLCLPWLQEGSAQAPESPSTIPVPS HPSSPLPVPLPSRPQNSTLRPGPFPTIPLSRLFDNAMLR AHRLHQLAFDTYQEFEEAYIPKEQKYSFLQNPQTSLCFS ESIPTPSNREETQQKSNLELLRISLLLIQSWLEPVQFLRSV FANSLVYGASDSNVYDLLKDLEEGIQTLMGRLEDGSPR TGQIFKQTYSKFDTNSHNDDALLKNYGLLYCFRKDMD KVETFLRIVQCRSVEGSCGFSPASASTQTSWTPRDLVSS QTQTQSCVPPTAGARHHHHHHHH |

TABLE 1-continued

Amino acid sequences of chimeras of the invention

| SEQ ID NO: | Description | Sequence |
|---|---|---|
| 40 | hGH (SEQ ID NO: 16) having a leader peptide (SEQ ID NO: 17) and a peptide derived from NKp44 (SEQ ID NO: 4) attached to its amino terminus, and peptide derived from NKp44 (SEQ ID NO: 3) attached to its carboxy terminus. | MATGSRTSLLLAFGLLCLPWLQEGSAQAPESPSTIPVPS HPSSPLPVPLPSRPQNSTLRPGPFPTIPLSRLFDNAMLR AHRLHQLAFDTYQEFEEAYIPKEQKYSFLQNPQTSLCFS ESIPTPSNREETQQKSNLELLRISLLLIQSWLEPVQFLRSV FANSLVYGASDSNVYDLLKDLEEGIQTLMGRLEDGSPR TGQIFKQTYSKFDTNSHNDDALLKNYGLLYCFRKDMD KVETFLRIVQCRSVEGSCGFSPASASTQTSWTPRDLVSS QTQTQSCVPPTAGAR |
| 41 | hGH (SEQ ID NO: 16) having a peptide derived from NKp44 (SEQ ID NO: 4) attached to its amino terminus, and peptide derived from NKp44 (SEQ ID NO: 3) attached to its carboxy terminus. | QAPESPSTIPVPSHPSSPLPVPLPSRPQNSTLRPGPFPTI PLSRLFDNAMLRAHRLHQLAFDTYQEFEEAYIPKEQKY SFLQNPQTSLCFSESIPTPSNREETQQKSNLELLRISLLLIQ SWLEPVQFLRSVFANSLVYGASDSNVYDLLKDLEEGIQ TLMGRLEDGSPRTGQIFKQTYSKFDTNSHNDDALLKNY GLLYCFRKDMDKVETFLRIVQCRSVEGSCGFSPASAST QTSWTPRDLVSSQTQTQSCVPPTAGAR |
| 42 | hGH (SEQ ID NO: 16) having a leader peptide (SEQ ID NO: 17) and a peptide derived from NKp44 (SEQ ID NO: 4) attached to its amino terminus. AND a peptide derived from NKp44 (SEQ ID NO: 4) and a His tag (SEQ ID NO: 7) attached to its carboxy terminus. | MATGSRTSLLLAFGLLCLPWLQEGSAQAPESPSTIPVPS HPSSPLPVPLPSRPQNSTLRPGPFPTIPLSRLFDNAMLR AHRLHQLAFDTYQEFEEAYIPKEQKYSFLQNPQTSLCFS ESIPTPSNREETQQKSNLELLRISLLLIQSWLEPVQFLRSV FANSLVYGASDSNVYDLLKDLEEGIQTLMGRLEDGSPR TGQIFKQTYSKFDTNSHNDDALLKNYGLLYCFRKDMD KVETFLRIVQCRSVEGSCGFQAPESPSTIPVPSHPSSPLP VPLPSRPQNSTLRPGPHHHHHHHH |
| 43 | hGH (SEQ ID NO: 16) having a leader peptide (SEQ ID NO: 17) attached to its amino terminus, and a peptide derived from NKp44 (SEQ ID NO: 4) attached to its amino terminus and carboxy terminus. | MATGSRTSLLLAFGLLCLPWLQEGSAQAPESPSTIPVPS HPSSPLPVPLPSRPQNSTLRPGPFPTIPLSRLFDNAMLR AHRLHQLAFDTYQEFEEAYIPKEQKYSFLQNPQTSLCFS ESIPTPSNREETQQKSNLELLRISLLLIQSWLEPVQFLRSV FANSLVYGASDSNVYDLLKDLEEGIQTLMGRLEDGSPR TGQIFKQTYSKFDTNSHNDDALLKNYGLLYCFRKDMD KVETFLRIVQCRSVEGSCGFQAPESPSTIPVPSHPSSPLP VPLPSRPQNSTLRPGP |
| 44 | hGH (SEQ ID NO: 16) having a peptide derived from NKp44 (SEQ ID NO: 4) attached to its amino and carboxy terminus. | QAPESPSTIPVPSHPSSPLPVPLPSRPQNSTLRPGPFPTI PLSRLFDNAMLRAHRLHQLAFDTYQEFEEAYIPKEQKY SFLQNPQTSLCFSESIPTPSNREETQQKSNLELLRISLLLIQ SWLEPVQFLRSVFANSLVYGASDSNVYDLLKDLEEGIQ TLMGRLEDGSPRTGQIFKQTYSKFDTNSHNDDALLKNY GLLYCFRKDMDKVETFLRIVQCRSVEGSCGFQAPESPS TIPVPSHPSSPLPVPLPSRPQNSTLRPGP |
| 45 | 'APE-GH-APE-APE' ('AGAA'): hGH (SEQ ID NO: 16) having a leader peptide (SEQ ID NO: 17) and a peptide derived from NKp44 (SEQ ID NO: 4) attached to its amino terminus, and two peptides derived from NKp44 (SEQ ID NO: 4) and a His tag (SEQ ID NO: 7) attached to its carboxy terminus in a sequential manner. | MATGSRTSLLLAFGLLCLPWLQEGSAQAPESPSTIPVPS HPSSPLPVPLPSRPQNSTLRPGPFPTIPLSRLFDNAMLR AHRLHQLAFDTYQEFEEAYIPKEQKYSFLQNPQTSLCFS ESIPTPSNREETQQKSNLELLRISLLLIQSWLEPVQFLRSV FANSLVYGASDSNVYDLLKDLEEGIQTLMGRLEDGSPR TGQIFKQTYSKFDTNSHNDDALLKNYGLLYCFRKDMD KVETFLRIVQCRSVEGSCGFQAPESPSTIPVPSHPSSPLP VPLPSRPQNSTLRPGPQAPESPSTIPVPSHPSSPLPVPL PSRPQNSTLRPGPHHHHHHHH |
| 46 | hGH (SEQ ID NO: 16) having a leader peptide (SEQ ID NO: 17) and a peptide derived from NKp44 (SEQ ID NO: 4) attached to its amino terminus, and two peptides derived from NKp44 (SEQ ID NO: 4) attached to its carboxy terminus in a sequential manner. | MATGSRTSLLLAFGLLCLPWLQEGSAQAPESPSTIPVPS HPSSPLPVPLPSRPQNSTLRPGPFPTIPLSRLFDNAMLR AHRLHQLAFDTYQEFEEAYIPKEQKYSFLQNPQTSLCFS ESIPTPSNREETQQKSNLELLRISLLLIQSWLEPVQFLRSV FANSLVYGASDSNVYDLLKDLEEGIQTLMGRLEDGSPR TGQIFKQTYSKFDTNSHNDDALLKNYGLLYCFRKDMD KVETFLRIVQCRSVEGSCGFQAPESPSTIPVPSHPSSPLP VPLPSRPQNSTLRPGPQAPESPSTIPVPSHPSSPLPVPL PSRPQNSTLRPGP |

TABLE 1-continued

Amino acid sequences of chimeras of the invention

| SEQ ID NO: | Description | Sequence |
|---|---|---|
| 47 | hGH (SEQ ID NO: 16) having a peptide derived from NKp44 (SEQ ID NO: 4) attached to its amino terminus, and two peptides derived from NKp44 (SEQ ID NO: 4) attached to its carboxy terminus in a sequential manner. | QAPESPSTIPVPSHPSSPLPVPLPSRPQNSTLRPGPFPTIPLSRLFDNAMLRAHRLHQLAFDTYQEFEEAYIPKEQKYSFLQNPQTSLCFSESIPTPSNREETQQKSNLELLRISLLLIQSWLEPVQFLRSVFANSLVYGASDSNVYDLLKDLEEGIQTLMGRLEDGSPRTGQIFKQTYSKFDTNSHNDDALLKNYGLLYCFRKDMDKVETFLRIVQCRSVEGSCGFQAPESPSTIPVPSHPSSPLPVPLPSRPQNSTLRPGPQAPESPSTIPVPSHPSSPLPVPLPSRPQNSTLRPGP |
| 48 | hGH (SEQ ID NO: 16) having a leader peptide (SEQ ID NO: 17) and a peptide derived from NKp44 (SEQ ID NO: 3) attached to its amino terminus, and two peptides derived from NKp44 (SEQ ID NO: 4) and a His tag (SEQ ID NO: 7) attached to its carboxy terminus in a sequential manner. | MATGSRTSLLLAFGLLCLPWLQEGSASPASASTQTSWTPRDLVSSQTQTQSCVPPTAGARFPTIPLSRLFDNAMLRAHRLHQLAFDTYQEFEEAYIPKEQKYSFLQNPQTSLCFSESIPTPSNREETQQKSNLELLRISLLLIQSWLEPVQFLRSVFANSLVYGASDSNVYDLLKDLEEGIQTLMGRLEDGSPRTGQIFKQTYSKFDTNSHNDDALLKNYGLLYCFRKDMDKVETFLRIVQCRSVEGSCGFQAPESPSTIPVPSHPSSPLPVPLPSRPQNSTLRPGPQAPESPSTIPVPSHPSSPLPVPLPSRPQNSTLRPGPHHHHHHHH |
| 49 | hGH (SEQ ID NO: 15) having a leader peptide (SEQ ID NO: 17) and a peptide derived from NKp44 (SEQ ID NO: 3) attached to its amino terminus, and two peptides derived from NKp44 (SEQ ID NO: 4) attached to its carboxy terminus in a sequential manner. | MATGSRTSLLLAFGLLCLPWLQEGSASPASASTQTSWTPRDLVSSQTQTQSCVPPTAGARFPTIPLSRLFDNAMLRAHRLHQLAFDTYQEFEEAYIPKEQKYSFLQNPQTSLCFSESIPTPSNREETQQKSNLELLRISLLLIQSWLEPVQFLRSVFANSLVYGASDSNVYDLLKDLEEGIQTLMGRLEDGSPRTGQIFKQTYSKFDTNSHNDDALLKNYGLLYCFRKDMDKVETFLRIVQCRSVEGSCGFQAPESPSTIPVPSHPSSPLPVPLPSRPQNSTLRPGPQAPESPSTIPVPSHPSSPLPVPLPSRPQNSTLRPGP |
| 50 | hGH (SEQ ID NO: 15) having a peptide derived from NKp44 (SEQ ID NO: 3) attached to its amino terminus, and two peptides derived from NKp44 (SEQ ID NO: 4) attached to its carboxy terminus in a sequential manner. | SPASASTQTSWTPRDLVSSQTQTQSCVPPTAGARFPTIPLSRLFDNAMLRAHRLHQLAFDTYQEFEEAYIPKEQKYSFLQNPQTSLCFSESIPTPSNREETQQKSNLELLRISLLLIQSWLEPVQFLRSVFANSLVYGASDSNVYDLLKDLEEGIQTLMGRLEDGSPRTGQIFKQTYSKFDTNSHNDDALLKNYGLLYCFRKDMDKVETFLRIVQCRSVEGSCGFQAPESPSTIPVPSHPSSPLPVPLPSRPQNSTLRPGPQAPESPSTIPVPSHPSSPLPVPLPSRPQNSTLRPGP |
| 51 | hGH (SEQ ID NO: 15) having a leader peptide (SEQ ID NO: 17) and a peptide derived from NKp44 (SEQ ID NO: 3) attached to its amino terminus, and two peptides derived from NKp44 (SEQ ID NO: 3) and a His tag (SEQ ID NO: 7) attached to its carboxy terminus in a sequential manner. | MATGSRTSLLLAFGLLCLPWLQEGSASPASASTQTSWTPRDLVSSQTQTQSCVPPTAGARFPTIPLSRLFDNAMLRAHRLHQLAFDTYQEFEEAYIPKEQKYSFLQNPQTSLCFSESIPTPSNREETQQKSNLELLRISLLLIQSWLEPVQFLRSVFANSLVYGASDSNVYDLLKDLEEGIQTLMGRLEDGSPRTGQIFKQTYSKFDTNSHNDDALLKNYGLLYCFRKDMDKVETFLRIVQCRSVEGSCGFSPASASTQTSWTPRDLVSSQTQTQSCVPPTAGARSPASASTQTSWTPRDLVSSQTQTQSCVPPTAGARHHHEIHHHH |
| 52 | hGH (SEQ ID NO: 16) having a peptide derived from NKp44 (SEQ ID NO: 3) attached to its amino terminus, and two peptides derived from NKp44 (SEQ ID NO: 3) attached to its carboxy terminus in a sequential manner. | SPASASTQTSWTPRDLVSSQTQTQSCVPPTAGARFPTIPLSRLFDNAMLRAHRLHQLAFDTYQEFEEAYIPKEQKYSFLQNPQTSLCFSESIPTPSNREETQQKSNLELLRISLLLIQSWLEPVQFLRSVFANSLVYGASDSNVYDLLKDLEEGIQTLMGRLEDGSPRTGQIFKQTYSKFDTNSHNDDALLKNYGLLYCFRKDMDKVETFLRIVQCRSVEGSCGFSPASASTQTSWTPRDLVSSQTQTQSCVPPTAGARSPASASTQTSWTPRDLVSSQTQTQSCVPPTAGAR |
| 71 | hGH (SEQ ID NO: 16) having two peptides derived from NKp44 (SEQ ID NO: 3) attached to its amino terminus, and two peptides derived from NKp44 (SEQ ID NO: 3) attached to its carboxy terminus in a sequential manner | SPASASTQTSWTPRDLVSSQTQTQSCVPPTAGARSPASASTQTSWTPRDLVSSQTQTQSCVPPTAGARFPTIPLSRLFDNAMLRAHRLHQLAFDTYQEFEEAYIPKEQKYSFLQNPQTSLCFSESIPTPSNREETQQKSNLELLRISLLLIQSWLEPVQFLRSVFANSLVYGASDSNVYDLLKDLEEGIQTLMGRLEDGSPRTGQIFKQTYSKFDTNSHNDDALLKNYGLLYCFRKDMDKVETFLRIVQCRSVEGSCGFSPASASTQTSWTPRDLVSSQTQTQSCVPPTAGAR |

TABLE 1-continued

Amino acid sequences of chimeras of the invention

| SEQ ID NO: | Description | Sequence |
|---|---|---|
| 53 | hGH (SEQ ID NO: 16) having a peptide derived from NKp44 (SEQ ID NO: 3) attached to its amino terminus, and two peptides derived from NKp44 (SEQ ID NO: 3) attached to its carboxy terminus in a sequential manner. | SPASASTQTSWTPRDLVSSQTQTQSCVPPTAGARSPA SASTQTSWTPRDLVSSQTQTQSCVPPTAGARFPTIPLS RLFDNAMLRAHRLHQLAFDTYQEFEEAYIPKEQKYSFL QNPQTSLCFSESIPTPSNREETQQKSNLELLRISLLLIQSW LEPVQFLRSVFANSLVYGASDSNVYDLLKDLEEGIQTL MGRLEDGSPRTGQIFKQTYSKFDTNSHNDDALLKNYGL LYCFRKDMDKVETFLRIVQCRSVEGSCGFSPASASTQTS WTPRDLVSSQTQTQSCVPPTAGARSPASASTQTSWTP RDLVSSQTQTQSCVPPTAGAR |
| 54 | hGH (SEQ ID NO: 16) having a leader peptide (SEQ ID NO: 17) and a peptide derived from NKp44 (SEQ ID NO: 4) attached to its amino terminus, and two peptides derived from NKp44 (SEQ ID NO: 3) and a His tag attachedto its carboxy terminus in a sequential manner. | MATGSRTSLLLAFGLLCLPWLQEGSAQAPESPSTIPVPS HPSSPLPVPLPSRPQNSTLRPGPFPTIPLSRLFDNAMLR AHRLHQLAFDTYQEFEEAYIPKEQKYSFLQNPQTSLCFS ESIPTPSNREETQQKSNLELLRISLLLIQSWLEPVQFLRSV FANSLVYGASDSNVYDLLKDLEEGIQTLMGRLEDGSPR TGQIFKQTYSKFDTNSHNDDALLKNYGLLYCFRKDMD KVETFLRIVQCRSVEGSCGFSPASASTQTSWTPRDLVSS QTQTQSCVPPTAGARSPASASTQTSWTPRDLVSSQTQ TQSCVPPTAGARHHHEIHHHH |
| 55 | hGH (SEQ ID NO: 16) having a leader peptide (SEQ ID NO: 17) and a peptide derived from NKp44 (SEQ ID NO: 4) attached to its amino terminus, and two peptides derived from NKp44 (SEQ ID NO: 3) attached to its carboxy terminus in a sequential manner. | MATGSRTSLLLAFGLLCLPWLQEGSAQAPESPSTIPVPS HPSSPLPVPLPSRPQNSTLRPGPFPTIPLSRLFDNAMLR AHRLHQLAFDTYQEFEEAYIPKEQKYSFLQNPQTSLCFS ESIPTPSNREETQQKSNLELLRISLLLIQSWLEPVQFLRSV FANSLVYGASDSNVYDLLKDLEEGIQTLMGRLEDGSPR TGQIFKQTYSKFDTNSHNDDALLKNYGLLYCFRKDMD KVETFLRIVQCRSVEGSCGFSPASASTQTSWTPRDLVSS QTQTQSCVPPTAGARSPASASTQTSWTPRDLVSSQTQ TQSCVPPTAGAR |
| 56 | hGH (SEQ ID NO: 16) having a peptide derived from NKp44 (SEQ ID NO: 4) attached to its amino terminus, and two peptides derived from NKp44 (SEQ ID NO: 3) attached to its carboxy terminus in a sequential manner. | QAPESPSTIPVPSHPSSPLPVPLPSRPQNSTLRPGPFPTI PLSRLFDNAMLRAHRLHQLAFDTYQEFEEAYIPKEQKY SFLQNPQTSLCFSESIPTPSNREETQQKSNLELLRISLLLIQ SWLEPVQFLRSVFANSLVYGASDSNVYDLLKDLEEGIQ TLMGRLEDGSPRTGQIFKQTYSKFDTNSHNDDALLKNY GLLYCFRKDMDKVETFLRIVQCRSVEGSCGFSPASAST QTSWTPRDLVSSQTQTQSCVPPTAGARSPASASTQTS WTPRDLVSSQTQTQSCVPPTAGAR |
| 57 | 'SPAmid': hGH (SEQ ID NO: 15) having a peptide derived from NKp44 (SEQ ID NO: 3) inserted between amino acids 175 and 176, and a His tag (SEQ ID NO: 7) attached to its carboxy terminus. | MATGSRTSLLLAFGLLCLPWLQEGSAFPTIPLSRLFDNA MLRAHRLHQLAFDTYQEFEEAYIPKEQKYSFLQNPQTS LCFSESIPTPSNREETQQKSNLELLRISLLLIQSWLEPVQF LRSVFANSLVYGASDSNVYDLLKDLEEGIQTLMGRLED GSPRTGQIFKQTYSKFDTNPASASTQTSWTPRDLVSS QTQTQSCVPPTAGARSHNDDALLKNYGLLYCFRKDM DKVETFLRIVQCRSVEGSCGFHHHHHHHH |
| 58 | hGH (SEQ ID NO: 15) having a peptide derived from NKp44 (SEQ ID NO: 3) inserted between amino acids 175 and 176 of its sequence. | MATGSRTSLLLAFGLLCLPWLQEGSAFPTIPLSRLFDNA MLRAHRLHQLAFDTYQEFEEAYIPKEQKYSFLQNPQTS LCFSESIPTPSNREETQQKSNLELLRISLLLIQSWLEPVQF LRSVFANSLVYGASDSNVYDLLKDLEEGIQTLMGRLED GSPRTGQIFKQTYSKFDTNPASASTQTSWTPRDLVSS QTQTQSCVPPTAGARSHNDDALLKNYGLLYCFRKDM DKVETFLRIVQCRSVEGSCGF |
| 59 | 'APEmidA': hGH (SEQ ID NO: 15) having a peptide derived from NKp44 (SEQ ID NO: 4) inserted between amino acids 175 and 176, and a His tag (SEQ ID NO: 7) attachedto its carboxy terminus. | MATGSRTSLLLAFGLLCLPWLQEGSAFPTIPLSRLFDNA MLRAHRLHQLAFDTYQEFEEAYIPKEQKYSFLQNPQTS LCFSESIPTPSNREETQQKSNLELLRISLLLIQSWLEPVQF LRSVFANSLVYGASDSNVYDLLKDLEEGIQTLMGRLED GSPRTGQIFKQTYSKFDTNQAPESPSTIPVPSHPSSPLPV PLPSRPQNSTLRPGPSHNDDALLKNYGLLYCFRKDMD KVETFLRIVQCRSVEGSCGFHHHHHHHH |
| 60 | hGH (SEQ ID NO: 16) having a peptide derived from NKp44 (SEQ ID NO: 4) inserted between amino acids 175 and 176 of its sequence. | FPTIPLSRLFDNAMLRAHRLHQLAFDTYQEFEEAYIPKE QKYSFLQNPQTSLCFSESIPTPSNREETQQKSNLELLRISL LLIQSWLEPVQFLRSVFANSLVYGASDSNVYDLLKDLEE GIQTLMGRLEDGSPRTGQIFKQTYSKFDTNQAPESPSTI PVPSHPSSPLPVPLPSRPQNSTLRPGPSHNDDALLKNY GLLYCFRKDMDKVETFLRIVQCRSVEGSCGF |

TABLE 1-continued

Amino acid sequences of chimeras of the invention

| SEQ ID NO: | Description | Sequence |
|---|---|---|
| 61 | hGH (SEQ ID NO: 15) having a peptide derived from NKp44 (SEQ ID NO: 4) inserted between amino acids 87 and 88, and a His tag (SEQ ID NO: 7) attached to its carboxy terminus. | MATGSRTSLLLAFGLLCLPWLQEGSAFPTIPLSRLFDNA MLRAHRLHQLAFDTYQEFEEAYIPKEQKYSFLQNPQTS LCFSESIPTPQAPESPSTIPVPSHPSSPLPVPLPSRPQNST LRPGPSNREETQQKSNLELLRISLLLIQSWLEPVQFLRSV FANSLVYGASDSNVYDLLKDLEEGIQTLMGRLEDGSPR TGQIFKQTYSKFDTNSHNDDALLKNYGLLYCFRKDMD KVETFLRIVQCRSVEGSCGFHHHHHHHH |
| 62 | hGH (SEQ ID NO: 16) having a peptide derived from NKp44 (SEQ ID NO: 4) inserted between amino acids 87 and 88 of its sequence. | FPTIPLSRLFDNAMLRAHRLHQLAFDTYQEFEEAYIPKE QKYSFLQNPQTSLCFSESIPTPQAPESPSTIPVPSHPSSPL PVPLPSRPQNSTLRPGPSNREETQQKSNLELLRISLLLIQ SWLEPVQFLRSVFANSLVYGASDSNVYDLLKDLEEGIQ TLMGRLEDGSPRTGQIFKQTYSKFDTNSHNDDALLKNY GLLYCFRKDMDKVETFLRIVQCRSVEGSCGF |
| 63 | hGH (SEQ ID NO: 15) having a peptide derived from NKp44 (SEQ ID NO: 3) inserted between amino acids 87 and 88, and a His tag (SEQ ID NO: 7) attached to its carboxy terminus. | MATGSRTSLLLAFGLLCLPWLQEGSAFPTIPLSRLFDNA MLRAHRLHQLAFDTYQEFEEAYIPKEQKYSFLQNPQTS LCFSESIPTPSPASASTQTSWTPRDLVSSQTQTQSCVPP TAGARSNREETQQKSNLELLRISLLLIQSWLEPVQFLRS VFANSLVYGASDSNVYDLLKDLEEGIQTLMGRLEDGSP RTGQIFKQTYSKFDTNSHNDDALLKNYGLLYCFRKDM DKVETFLRIVQCRSVEGSCGFHHHHHHHH |
| 64 | hGH (SEQ ID NO: 16) having a peptide derived from NKp44 (SEQ ID NO: 3) insertedd between amino acids 87 and 88 of its sequence. | FPTIPLSRLFDNAMLRAHRLHQLAFDTYQEFEEAYIPKE QKYSFLQNPQTSLCFSESIPTPSPASASTQTSWTPRDLV SSQTQTQSCVPPTAGARSNREETQQKSNLELLRISLLLI QSWLEPVQFLRSVFANSLVYGASDSNVYDLLKDLEEGI QTLMGRLEDGSPRTGQIFKQTYSKFDTNSHNDDALLKN YGLLYCFRKDMDKVETFLRIVQCRSVEGSCGF |
| 65 | S2A-precision-HIS: IL2 signal peptide-SPA-IL2-APE-Precision-HIS 8 (permitting HIS release) | MYRMLLSCIALSLALVTNGSASPASASTQTSWTPRDLVS SQTQTQSCVPPTAGARAPTSSSTKKTQLQLEHLLLDLQ MILNGINNYKNPKLTRMLTFKYMPKKATELKHLQCLE EELKPLEEVLNLAQSKNFHLRPRDLISNINVIVLELKGSE TTFMCEYADETATIVEFLNRWITFCQSIISTLTQAPESPST IPVPSHPSSPLPVPLPSRPQNSTLRPGPLEVLFQGPHHHH HHHH |
| 66 | S2A | SPASASTQTSWTPRDLVSSQTQTQSCVPPTAGARAPTSS STKKTQLQLEHLLLDLQMILNGINNYKNPKLTRMLTFK FYMPKKATELKHLQCLEEELKPLEEVLNLAQSKNFHLR PRDLISNINVIVLELKGSETTFMCEYADETATIVEFLNRW ITFCQSIISTLTQAPESPSTIPVPSHPSSPLPVPLPSRPQNST LRPGP |
| 67 | A2A-Lin-HIS: IL2 signal peptide-APE-IL2-APE-Precision-HIS 8 | MYRMLLSCIALSLALVTNGSAQAPESPSTIPVPSHPSSPL PVPLPSRPQNSTLRPGPAPTSSSTKKTQLQLEHLLLDLQ MILNGINNYKNPKLTRMLTFKYMPKKATELKHLQCLE EELKPLEEVLNLAQSKNFHLRPRDLISNINVIVLELKGSE TTFMCEYADETATIVEFLNRWITFCQSIISTLTQAPESPST IPVPSHPSSPLPVPLPSRPQNSTLRPGPLEVLFQGPHHHH HHHH |
| 68 | A2A | QAPESPSTIPVPSHPSSPLPVPLPSRPQNSTLRPGPAPTSSS TKKTQLQLEHLLLDLQMILNGINNYKNPKLTRMLTFKF YMPKKATELKHLQCLEEELKPLEEVLNLAQSKNFHLRP RDLISNINVIVLELKGSETTFMCEYADETATIVEFLNRWI TFCQSIISTLTQAPESPSTIPVPSHPSSPLPVPLPSRPQNSTL RPGP |
| 69 | S2S-precision-His IL2 signal peptide-SPA-IL2-SPA-Precision-HIS8 | MYRMLLSCIALSLALVTNGSASPASASTQTSWTPRDLVS SQTQTQSCVPPTAGARAPTSSSTKKTQLQLEHLLLDLQ MILNGINNYKNPKLTRMLTFKYMPKKATELKHLQCLE EELKPLEEVLNLAQSKNFHLRPRDLISNINVIVLELKGSE TTFMCEYADETATIVEFLNRWITFCQSIISTLTSPASASTQ TSWTPRDLVSSQTQTQSCVPPTAGARLEVLFQGPHHHH HHHH |

TABLE 1-continued

Amino acid sequences of chimeras of the invention

| SEQ ID NO: | Description | Sequence |
|---|---|---|
| 70 | S2S | SPASASTQTSWTPRDLVSSQTQTQSCVPPTAGARAPTSS STKKTQLQLEHLLLDLQMILNGINNYKNPKLTRMLTFK FYMPKKATELKHLQCLEEELKPLEEVLNLAQSKNFHLR PRDLISNINVIVLELKGSETTFMCEYADETATIVEFLNRW ITFCQSIISTLTSPASASTQTSWTPRDLVSSQTQTQSCVPP TAGAR |

In some embodiments, the biological activity of the chimera is at least equivalent to the biological activity of the proteins of interest. In some embodiments, the chimera is at least equivalent to the protein of interest in terms of pharmacological measures such as pharmacokinetics and pharmacodynamics. In other embodiments, the chimera has increased $C_{max}$ compared to the protein of interest. In other embodiments, the chimera has increased $C_{avg}$ compared to the protein of interest. In other embodiments, the chimera has increased $T_{max}$ compared to the protein of interest. In another embodiment, the chimera has improved AUC compared to the protein of interest. In another embodiment, the chimera has enhanced potency compared to the protein of interest. In another embodiment, the chimera has improved efficacy compared to the protein of interest.

In another embodiment, the chimera has increased serum half-life compared to the unmodified protein of interest. In another embodiment, the chimera has increased circulating half-life in comparison to the unmodified protein of interest. In another embodiment, the chimera has increased circulating half-life and plasma residence time, decreased clearance, and increased clinical activity in vivo, compared to the unmodified proteins of interest.

In another embodiment, the peptide derived from NKp44 acts as a protectant against degradation of proteins of interest. In another embodiment, the peptide derived from NKp44 increases the $C_{max}$ of the proteins of interest. In another embodiment, the peptide derived from NKp44 extends the $T_{max}$ of the proteins of interest. In another embodiment, the peptide derived from NKp44 increases the $C_{avg}$ of the proteins of interest. In another embodiment, the peptide derived from NKp44 improves the AUC of the proteins of interest. In another embodiment, the peptide derived from NKp44 extends circulatory half-lives of the proteins of interest. In some embodiments, the peptide derived from NKp44 enhances the potency of the proteins of interest. In some embodiments, the peptide derived from NKp44 enhances the efficacy of the proteins of interest.

As used herein, "half-life", refers to the time required to eliminate one-half of the quantity of an agent. For a non-limiting example, the time at which the concentration of an agent has reached one-half its initial or maximum value. The terms "extended biological half-life", "prolonged biological half-life", "increased serum half-life" and "increased circulatory half-life" used herein in reference to the chimeras of the invention to indicate that the chimeras of the invention are cleared at a slower rate than either the endogenous protein or the recombinantly produced version thereof. For a non-limiting example, the half-life of a synthetic HCG-β produced by the methods of the present invention (e.g., a chimera comprising HCG-β or a fragment thereof and at least one peptide derived from NKp44) in a subject would be "increased" if it exceeds the half-life of either endogenous HCG-β or recombinantly produced native HCG-β.

As used herein throughout the text the terms "improve", "increase", "extend" and "enhance", and all their grammatical forms, are used interchangeably to indicate at least 1.1, 1.2, 1.3, 1.4, 1.5, 1.6, 1.7, 1.8, 1.9, 2, 2.5, 3, 3.5, 4, 4.5, 5, 5.5, 6, 6.5, 7, 7.5, 8, 8.5, 9, 9.5, 10, or 20 folds increase. In some embodiments, there is provided at least 5%, 10%, 15%, 20%, 25%, 30%, 35%, 40%, 50%, 60%, 70%, 80%, 90%, 100%, 150%, or 200% increase. Each possibility represents a separate embodiment of the instant invention.

As used herein, the term "pharmacological properties" refers to any desirable or favorable biological activities or physicochemical characteristics of an agent (e.g., a protein of interest) administered to a physiological system. As used herein, the term "pharmacokinetic properties" refers to the action of an agent (e.g., protein of interest) in a subject, cell, tissue, or organ over a period of time including, but not limited to, the processes of absorption, distribution, localization in tissues, biotransformation, and excretion.

The terms "AUC", "$C_{max}$", and "$T_{max}$" are used herein in accordance with their normal meaning to refer to pharmacokinetic parameters that may be used to characterize the pharmacokinetic responses of a particular drug product in an animal or human subject. The term "AUC" as used herein, means an area under the plasma concentration-time curve, AUC represents changes in blood, serum, or plasma concentrations of a substance, e.g., a protein of interest, over time. As used herein, the term "$C_{max}$" refers to the maximum or peak concentration of a drug observed after its administration, and the term "$T_{max}$" refers to the time at which maximum concentration ($C_{max}$) occurs.

The term "$C_{avg}$" as used herein, means the plasma concentration of the drug within the dosing interval, i.e. about 24-hours, and is calculated as AUC/dosing interval.

As used herein the term "potency" refers to the specific ability or capacity of the protein, as indicated by appropriate laboratory tests, to yield a given result. A high potency refers to the ability to induce a larger response at low concentrations. As used herein, "EC50" is intended to refer to the concentration of a substance (e.g., a protein, a compound or a drug) that is required to induce 50% of the maximum effect (e.g., a biological process). As used herein, "IC50," is intended to refer to the concentration of a substance (e.g., a protein, a compound or a drug) that is required to induce 50% inhibitory effect.

As used herein, the term "efficacy" refers to the degree to which a desired effect is obtained.

In another embodiment, the chimera is used in the same manner as unmodified protein of interest.

In another embodiment, the chimera has enhanced potency in comparison to the protein of interest. In some embodiments, the chimera of the invention has a lower EC50 compared to that of the unmodified protein of interest.

In another embodiment, chimeras of this invention have an increased circulating half-life and plasma residence time, decreased clearance, and increased clinical activity in vivo. In another embodiment, due to the improved properties of the chimeras as described herein, these chimeras are administered less frequently than unmodified proteins of interest. In another embodiment, decreased frequency of administration will result in improved patient compliance leading to improved treatment outcomes, as well as improved patient quality of life.

In another embodiment, chimeras of the instant invention have an improved potency, improved stability, elevated AUC levels, and/or enhanced circulating half-life compared to unmodified cytokines and/or conventional conjugates of cytokines (e.g., linked to poly(ethylene glycol)). In some embodiments, the conventional conjugates have the molecular weight and linker structure of the conjugates (chimeras) of this invention.

In some embodiments of the instant invention, hCG half-life is extended compared to naturally occurring hCG by substituting 28 amino acids located at the carboxy terminus of the hCG with at least one peptide derived from NKp44.

In some embodiments, biological half-life of proteins of interest (e.g., cytokines) prepared by the teachings of the instant invention is increased compared to that of unmodified proteins of interest or cytokines. In some embodiments, potency of proteins of interest (e.g., cytokines) prepared by the teachings of the instant invention is enhanced compared to that of unmodified proteins of interest or cytokines.

As exemplified in the example section of the instant invention, a growth hormone prepared by the teachings of the instant invention has extended half-life compared to that of unmodified growth hormone. Further, a growth hormone prepared by the teachings of the instant invention has lower EC50 value compared to that of unmodified growth hormone. In some embodiments, a growth hormone prepared by the teachings of the instant invention has improved efficacy compared to that of unmodified growth hormone. In some embodiments, a growth hormone prepared by the teachings of the instant invention has improved potency compared to that of an unmodified growth hormone.

Synthesizing the Chimera

According to one embodiment, the chimeras of the present invention may be synthesized or prepared by any method and/or technique known in the art for peptide synthesis. According to another embodiment, the chimeras may be synthesized by a solid phase peptide synthesis method of Merrifield (see J. Am. Chem. Soc, 85:2149, 1964). According to another embodiment, the chimeric polypeptides of the present invention can be synthesized using standard solution methods well known in the art (see, for example, Bodanszky, M., Principles of Peptide Synthesis, Springer-Verlag, 1984).

In general, the synthesis methods comprise sequential addition of one or more amino acids or suitably protected amino acids to a growing peptide chain bound to a suitable resin. Normally, either the amino or carboxyl group of the first amino acid is protected by a suitable protecting group. The protected or derivatized amino acid can then be either attached to an inert solid support (resin) or utilized in solution by adding the next amino acid in the sequence having the complimentary (amino or carboxyl) group suitably protected, under conditions conductive for forming the amide linkage. The protecting group is then removed from this newly added amino acid residue and the next amino acid (suitably protected) is added, and so forth. After all the desired amino acids have been linked in the proper sequence, any remaining protecting groups are removed sequentially or concurrently, and the peptide chain, if synthesized by the solid phase method, is cleaved from the solid support to afford the final peptide.

In the solid phase peptide synthesis method, the alpha-amino group of the amino acid is protected by an acid or base sensitive group. Such protecting groups should have the properties of being stable to the conditions of peptide linkage formation, while being readily removable without destruction of the growing peptide chain. Suitable protecting groups are t-butyloxycarbonyl (BOC), benzyloxycarbonyl (Cbz), biphenylisopropyloxycarbonyl, t-amyloxycarbonyl, isobornyloxycarbonyl, (alpha, alpha)-dimethyl-3,5 dimethoxybenzyloxycarbonyl, o-nitrophenylsulfenyl, 2-cyano-t-butyloxycarbonyl, 9-fluorenylmethyloxycarbonyl (FMOC) and the like. In the solid phase peptide synthesis method, the C-terminal amino acid is attached to a suitable solid support. Suitable solid supports useful for the above synthesis are those materials, which are inert to the reagents and reaction conditions of the stepwise condensation-deprotection reactions, as well as being insoluble in the solvent media used. Suitable solid supports are chloromethylpolystyrene-divinylbenzene polymer, hydroxymethyl-polystyrene-divinylbenzene polymer, and the like. The coupling reaction is accomplished in a solvent such as ethanol, acetonitrile, N,N-dimethylformamide (DMF), and the like. The coupling of successive protected amino acids can be carried out in an automatic polypeptide synthesizer as is well known in the art.

In another embodiment, peptides of the invention may be synthesized such that one or more of the bonds, which link the amino acid residues of the peptides are non-peptide bonds. In another embodiment, the non-peptide bonds include, but are not limited to, imino, ester, hydrazide, semicarbazide, and azo bonds, which can be formed by reactions well known to skilled in the art.

In another embodiment, the chimeric polypeptide of the present invention is provided to the subject per se. In one embodiment, the chimeric polypeptide of the present invention is provided to the subject as part of a pharmaceutical composition where it is mixed with a pharmaceutically acceptable carrier.

Polynucleotides of the Invention

The invention further encompasses a polynucleotide sequence comprising a nucleic acid encoding any of the peptides of the invention. In another embodiment, the nucleic acid sequence encoding the peptide derived from NKp44 is at least 70%, or alternatively at least 80%, or alternatively at least 90%, or alternatively at least 95%, or alternatively at least 99% homologous to the nucleic acid sequence encoding amino acids 130 to 199 of native human NKp44 nucleic acid sequence or a fragment thereof. Each possibility represents a separate embodiment of the present invention.

In some embodiment, the invention provides a polynucleotide encoding a chimera comprising a protein of interest and a peptide derived from NKp44.

In some embodiments, the polynucleotide of the present invention is ligated into an expression vector, comprising a transcriptional control of a cis-regulatory sequence (e.g., promoter sequence). In some embodiments, the cis-regulatory sequence is suitable for directing constitutive expression of the chimera of the present invention. In some embodiments, the cis-regulatory sequence is suitable for directing tissue-specific expression of the chimera of the present invention. In some embodiments, the cis-regulatory sequence is suitable for directing inducible expression of the chimera of the present invention.

In some embodiments, tissue-specific promoters suitable for use with the present invention include sequences which are functional in specific cell population. Examples include, but are not limited to, promoters such as albumin that is liver specific (Pinkert et al., (1987) Genes Dev. 1:268-277), lymphoid specific promoters (Calame et al., (1988) Adv. Immunol. 43:235-275); in particular promoters of T-cell receptors (Winoto et al., (1989) EMBO J. 8:729-733) and immunoglobulins; (Banerji et al. (1983) Cell 33729-740), neuron-specific promoters such as the neurofilament promoter (Byrne et al. (1989) Proc. Natl. Acad. Sci. USA 86:5473-5477), pancreas-specific promoters (Edlunch et al. (1985) Science 230:912-916) or mammary gland-specific promoters such as the milk whey promoter (U.S. Pat. No. 4,873,316 and European Application Publication No. 264, 166). Inducible promoters suitable for use with the present invention include, for example, the tetracycline-inducible promoter (Srour, M. A., et al., 2003. Thromb. Haemost. 90: 398-405).

The term "polynucleotide" refers to a nucleic acid (e.g., DNA or RNA) sequence that comprises coding sequences necessary for the production of a polypeptide. In one embodiment, the a polynucleotide refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

In one embodiment, "complementary polynucleotide sequence" refers to a sequence, which results from reverse transcription of messenger RNA using a reverse transcriptase or any other RNA dependent DNA polymerase. In one embodiment, the sequence can be subsequently amplified in vivo or in vitro using a DNA polymerase.

In one embodiment, "genomic polynucleotide sequence" refers to a sequence derived (isolated) from a chromosome and thus it represents a contiguous portion of a chromosome.

In one embodiment, "composite polynucleotide sequence" refers to a sequence, which is at least partially complementary and at least partially genomic. In one embodiment, a composite sequence can include some exonal sequences required to encode the polypeptide of the present invention, as well as some intronic sequences interposing there between. In one embodiment, the intronic sequences can be of any source, including of other genes, and typically will include conserved splicing signal sequences. In one embodiment, intronic sequences include cis acting expression regulatory elements.

In one embodiment, the polynucleotides of the present invention further comprise a signal sequence encoding a signal peptide to direct the chimera of the invention across or into a cell membrane. In one embodiment, the signal peptide directs the chimera of the present invention for secretion from cells. In one embodiment, following expression and secretion, the signal peptides are cleaved from the precursor proteins resulting in the mature proteins.

In some embodiments, polynucleotides of the present invention are prepared using PCR techniques as described in Example 1, or any other method or procedure known to one skilled in the art. In some embodiments, the procedure involves the ligation of two different DNA sequences (See, for example, "Current Protocols in Molecular Biology", eds. Ausubel et al., John Wiley & Sons, 1992).

In one embodiment, polynucleotides of the present invention are inserted into expression vectors (i.e., a nucleic acid construct) to enable expression of the recombinant polypeptide. In one embodiment, the expression vector of the present invention includes additional sequences which render this vector suitable for replication and integration in prokaryotes. In one embodiment, the expression vector of the present invention includes additional sequences which render this vector suitable for replication and integration in eukaryotes. In one embodiment, the expression vector of the present invention includes a shuttle vector which renders this vector suitable for replication and integration in both prokaryotes and eukaryotes. In some embodiments, cloning vectors comprise transcription and translation initiation sequences (e.g., promoters, enhancers) and transcription and translation terminators (e.g., polyadenylation signals).

In one embodiment, a variety of prokaryotic or eukaryotic cells can be used as host-expression systems to express the chimera of the present invention. In some embodiments, these include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence.

In some embodiments, non-bacterial expression systems are used (e.g. mammalian expression systems) to express the chimera of the present invention. In one embodiment, the expression vector is used to express polynucleotides of the present invention in mammalian cells.

In some embodiments, in bacterial systems of the present invention, several expression vectors can be advantageously selected depending upon the use intended for the polypeptide expressed. In one embodiment, large quantities of polypeptide are desired. In one embodiment, vectors that direct the expression of high levels of the protein product, possibly as a fusion with a hydrophobic signal sequence, which directs the expressed product into the periplasm of the bacteria or the culture medium where the protein product is readily purified are desired. In one embodiment, certain fusion protein engineered with a specific cleavage site to aid in recovery of the polypeptide. In one embodiment, vectors adaptable to such manipulation include, but are not limited to, the pET series of E. coli expression vectors [Studier et al., Methods in Enzymol. 185:60-89 (1990)].

In one embodiment, yeast expression systems are used. In one embodiment, a number of vectors containing constitutive or inducible promoters can be used in yeast as disclosed in U.S. Pat. No. 5,932,447. In another embodiment, vectors which promote integration of foreign DNA sequences into the yeast chromosome are used.

In one embodiment, the expression vector of the present invention may further include additional polynucleotide sequences that allow, for example, the translation of several proteins from a single mRNA such as an internal ribosome entry site (IRES) and sequences for genomic integration of the promoter-chimeric polypeptide.

In some embodiments, mammalian expression vectors include, but are not limited to, pcDNA3, pcDNA3.1 (±), pGL3, pZeoSV2(±), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

In some embodiments, expression vectors containing regulatory elements from eukaryotic viruses such as retroviruses are used by the present invention. SV40 vectors include pSVT7 and pMT2. In some embodiments, vectors derived from bovine papilloma virus include pBV-1MTHA, and vectors derived from Epstein Bar virus include pHEBO, and p205. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

In some embodiments, recombinant viral vectors, which offer advantages such as lateral infection and targeting specificity, are used for in vivo expression of the chimera of the present invention. In one embodiment, lateral infection is inherent in the life cycle of, for example, retrovirus and is the process by which a single infected cell produces many progeny virions that bud off and infect neighboring cells. In one embodiment, the result is that a large area becomes rapidly infected, most of which was not initially infected by the original viral particles. In one embodiment, viral vectors are produced that are unable to spread laterally. In one embodiment, this characteristic can be useful if the desired purpose is to introduce a specified gene into only a localized number of targeted cells.

Various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

A person with skill in the art will appreciate that the chimera of the present invention can also be expressed from a nucleic acid construct administered to the individual employing any suitable mode of administration, described hereinabove (i.e., in vivo gene therapy). In one embodiment, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex vivo gene therapy).

In one embodiment, in vivo gene therapy using a cytokine has been attempted in animal models such as rodents [Bohl et al., Blood. 2000; 95:2793-2798], primates [Gao et al., Blood, 2004, Volume 103, Number 9] and has proven successful in human clinical trials for patients with chronic renal failure [Lippin et al Blood 2005, 106, Number 7].

In one embodiment, plant expression vectors are used. In one embodiment, the expression of a polypeptide coding sequence is driven by a number of promoters. In some embodiments, viral promoters such as the 35S RNA and 19S RNA promoters of CaMV [Brisson et al., Nature 310:511-514 (1984)], or the coat protein promoter to TMV [Takamatsu et al., EMBO J. 6:307-311 (1987)] are used. In another embodiment, plant promoters are used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. In one embodiment, constructs are introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VIII, pp 421-463 (1988)]. Other expression systems such as insects and mammalian host cell systems, which are well known in the art, can also be used by the present invention.

It will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

In some embodiments, transformed cells are cultured under effective conditions, which allow for the expression of high amounts of recombinant polypeptide. In some embodiments, effective culture conditions include, but are not limited to, effective media, bioreactor, temperature, pH and oxygen conditions that permit protein production. In one embodiment, an effective medium refers to any medium in which a cell is cultured to produce the recombinant polypeptide of the present invention. In some embodiments, a medium typically includes an aqueous solution having assimilable carbon, nitrogen and phosphate sources, and appropriate salts, minerals, metals and other nutrients, such as vitamins. In some embodiments, cells of the present invention can be cultured in conventional fermentation bioreactors, shake flasks, test tubes, microtiter dishes and petri plates. In some embodiments, culturing is carried out at a temperature, pH and oxygen content appropriate for a recombinant cell. In some embodiments, culturing conditions are within the expertise of one of ordinary skill in the art.

In some embodiments, depending on the vector and host system used for production, resultant chimeras of the present invention either remain within the recombinant cell, secreted into the fermentation medium, secreted into a space between two cellular membranes, such as the periplasmic space in *E. coli*; or retained on the outer surface of a cell or viral membrane. In one embodiment, following a predetermined time in culture, recovery of the recombinant polypeptide is affected.

In one embodiment, the phrase "recovering the recombinant polypeptide" used herein refers to collecting the whole fermentation medium containing the polypeptide and need not imply additional steps of separation or purification.

In one embodiment, chimeras of the present invention are purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

In one embodiment, to facilitate recovery, the expressed coding sequence can be engineered to encode the polypeptide of the present invention and fused cleavable moiety. In one embodiment, a fusion protein can be designed so that the polypeptide can be readily isolated by affinity chromatography; e.g., by immobilization on a column specific for the cleavable moiety. In one embodiment, a cleavage site is engineered between the polypeptide and the cleavable moiety, and the polypeptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

In one embodiment, the chimeric polypeptide of the present invention is retrieved in "substantially pure" form that allows for the effective use of the protein in the applications described herein.

As used herein, the term "substantially pure" describes a peptide/ polypeptide or other material which has been separated from its native contaminants. Typically, a monomeric peptide is substantially pure when at least about 60 to 75% of a sample exhibits a single peptide backbone. Minor variants or chemical modifications typically share the same peptide sequence. A substantially pure peptide can comprise over about 85 to 90% of a peptide sample, and can be over 95% pure, over 97% pure, or over about 99% pure. Purity can be measured on a polyacrylamide gel, with homogeneity determined by staining. Alternatively, for certain purposes high resolution may be necessary and HPLC or a similar means for purification can be used. For most purposes, a simple chromatography column or polyacrylamide gel can be used to determine purity.

The term "purified" does not require the material to be present in a form exhibiting absolute purity, exclusive of the presence of other compounds. Rather, it is a relative definition. A peptide is in the "purified" state after purification of the starting material or of the natural material by at least one order of magnitude, 2 or 3, or 4 or 5 orders of magnitude.

In one embodiment, the chimeric polypeptides of the present invention are substantially free of naturally-associated host cell components. The term "substantially free of naturally-associated host cell components" describes a peptide or other material which is separated from the native contaminants which accompany it in its natural host cell state. Thus, a peptide which is chemically synthesized or synthesized in a cellular system different from the host cell from which it naturally originates will be free from its naturally-associated host cell components.

In one embodiment, the polypeptide of the present invention can also be synthesized using in vitro expression systems. In one embodiment, in vitro synthesis methods are well known in the art and the components of the system are commercially available.

Pharmaceutical Compositions

According to another aspect, the invention provides a pharmaceutical composition comprising as an active ingredient a therapeutically effective amount of the chimera of the present invention, and a pharmaceutically acceptable carrier and/or diluents. In some embodiments, the pharmaceutical composition facilitates administration of a compound to an organism.

In another embodiment, the pharmaceutical compositions of the invention may be formulated in the form of a pharmaceutically acceptable salt of the chimeras of the present invention or their analogs, or derivatives thereof. In another embodiment, pharmaceutically acceptable salts include those salts formed with free amino groups such as salts derived from non-toxic inorganic or organic acids such as hydrochloric, phosphoric, acetic, oxalic, tartaric acids, and the like, and those salts formed with free carboxyl groups such as salts derived from non-toxic inorganic or organic bases such as sodium, potassium, ammonium, calcium, ferric hydroxides, isopropylamine, triethylamine, 2-ethylamino ethanol, histidine, procaine, and the like.

As used herein, the term "carrier" refers to a diluent, adjuvant, excipient, or vehicle with which the therapeutic compound is administered. Such pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerin, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfate; and agents for the adjustment of tonicity such as sodium chloride or dextrose are also envisioned. The carrier may comprise, in total, from about 0.1% to about 99.99999% by weight of the pharmaceutical compositions presented herein.

As used herein, the term "pharmaceutically acceptable" means suitable for administration to a subject, e.g., a human. For example, the term "pharmaceutically acceptable" can mean approved by a regulatory agency of the Federal or a state government or listed in the U. S. Pharmacopeia or other generally recognized pharmacopeia for use in animals, and more particularly in humans.

In another embodiment, the compositions of the invention take the form of solutions, suspensions, emulsions, tablets, pills, capsules, powders, gels, creams, ointments, foams, pastes, sustained-release formulations and the like. In another embodiment, the compositions of the invention can be formulated as a suppository, with traditional binders and carriers such as triglycerides, microcrystalline cellulose, gum tragacanth or gelatin. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in: Remington's Pharmaceutical Sciences" by E. W. Martin, the contents of which are hereby incorporated by reference herein. Such compositions will contain a therapeutically effective amount of the chimera of the invention, preferably in a substantially purified form, together with a suitable amount of carrier so as to provide the form for proper administration to the subject.

According to an embodiment of the invention, pharmaceutical compositions contain 0.1%-95% of the chimeric polypeptide(s) of the present invention, derivatives, or analogs thereof. According to another embodiment of the invention, pharmaceutical compositions contain 1%-70% of the chimeric polypeptide(s) derivatives, or analogs thereof. According to another embodiment of the invention, the composition or formulation to be administered may contain a quantity of chimeric polypeptide(s), derivatives, or analogs thereof, according to embodiments of the invention in an amount effective to treat the condition or disease of the subject being treated.

An embodiment of the invention relates to chimeric polypeptides of the present invention, derivatives, or analogs thereof, presented in unit dosage form and prepared by any of the methods well known in the art of pharmacy. In an embodiment of the invention, the unit dosage form is in the form of a tablet, capsule, lozenge, wafer, patch, ampoule, vial or pre-filled syringe. In addition, in vitro assays may optionally be employed to help identify optimal dosage ranges. The precise dose to be employed in the formulation will also depend on the route of administration, and the nature of the disease or disorder, and should be decided according to the judgment of the practitioner and each patient's circumstances. Effective doses can be extrapolated from dose-response curves derived from in-vitro or in-vivo animal model test bioassays or systems.

According to one embodiment, the compositions of the present invention are administered in the form of a pharmaceutical composition comprising at least one of the active components (chimeras) of this invention together with a pharmaceutically acceptable carrier or diluent. In another embodiment, the compositions of this invention can be administered either individually or together in any conventional oral, parenteral or transdermal dosage form.

As used herein, the terms "administering," "administration," and like terms refer to any method which, in sound medical practice, delivers a composition containing an active agent to a subject in such a manner as to provide a therapeutic effect.

Depending on the location of the tissue of interest, the chimeras of the present invention can be administered in any manner suitable for the provision of the chimeric polypeptides to cells within the tissue of interest. Thus, for example, a composition containing the chimeric polypeptides of the present invention can be introduced, for example, into the systemic circulation, which will distribute the peptide to the tissue of interest. Alternatively, a composition can be applied topically to the tissue of interest (e.g., injected, or pumped as a continuous infusion, or as a bolus within a tissue, applied to all or a portion of the surface of the skin, etc.).

In some embodiments, the chimeras and/ or the pharmaceutical compositions comprising the chimeras are administered via oral, rectal, vaginal, topical, nasal, ophthalmic, transdermal, subcutaneous, intramuscular, intraperitoneal or intravenous routes of administration. The route of administration of the pharmaceutical composition will depend on the disease or condition to be treated. Suitable routes of administration include, but are not limited to, parenteral injections, e.g., intradermal, intravenous, intramuscular, intralesional, subcutaneous, intrathecal, and any other mode of injection as known in the art. Although the bioavailability of peptides administered by other routes can be lower than when administered via parenteral injection, by using appropriate formulations it is envisaged that it will be possible to administer the compositions of the invention via transdermal, oral, rectal, vaginal, topical, nasal, inhalation and ocular modes of treatment. In addition, it may be desirable to introduce the pharmaceutical compositions of the invention by any suitable route, including intraventricular and intrathecal injection; intraventricular injection may be facilitated by an intraventricular catheter, for example, attached to a reservoir. Pulmonary administration can also be employed, e.g., by use of an inhaler or nebulizer.

For topical application, a peptide of the present invention, derivative, analog or a fragment thereof can be combined with a pharmaceutically acceptable carrier so that an effective dosage is delivered, based on the desired activity. The carrier can be in the form of, for example, and not by way of limitation, an ointment, cream, gel, paste, foam, aerosol, suppository, pad or gelled stick.

For oral applications, the pharmaceutical composition may be in the form of tablets or capsules, which can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate; or a glidant such as colloidal silicon dioxide. When the dosage unit form is a capsule, it can contain, in addition to materials of the above type, a liquid carrier such as fatty oil. In addition, dosage unit forms can contain various other materials which modify the physical form of the dosage unit, for example, coatings of sugar, shellac, or other enteric agents. The tablets of the invention can further be film coated.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes.

According to some embodiments, the peptides (e.g., chimeras) of the present invention, derivatives, or analogs thereof can be delivered in a controlled release system. In another embodiment, an infusion pump can be used to administer the peptide such as the one that is used, for example, for delivering insulin or chemotherapy to specific organs or tumors. In another embodiment, the peptides of the invention are administered in combination with a biodegradable, biocompatible polymeric implant, which releases the peptide over a controlled period of time at a selected site. Examples of preferred polymeric materials include, but are not limited to, polyanhydrides, polyorthoesters, polyglycolic acid, polylactic acid, polyethylene vinyl acetate, copolymers and blends thereof (See, Medical applications of controlled release, Langer and Wise (eds.), 1974, CRC Pres., Boca Raton, Fla., the contents of which are hereby incorporated by reference in their entirety). In yet another embodiment, a controlled release system can be placed in proximity to a therapeutic target, thus requiring only a fraction of the systemic dose.

The presently described peptides (e.g., chimeras), derivatives, or analogs thereof may also be contained in artificially created structures such as liposomes, ISCOMS, slow-releasing particles, and other vehicles which increase the half-life of the peptides or polypeptides in serum. Liposomes include emulsions, foams, micelles, insoluble monolayers, liquid crystals, phospholipid dispersions, lamellar layers and the like. Liposomes for use with the presently described peptides are formed from standard vesicle-forming lipids which generally include neutral and negatively charged phospholipids and a sterol, such as cholesterol. The selection of lipids is generally determined by considerations such as liposome size and stability in the blood. A variety of methods are available for preparing liposomes as reviewed, for example, by Coligan, J. E. et al, Current Protocols in Protein Science, 1999, John Wiley & Sons, Inc., New York, and see also U.S. Pat. Nos. 4,235,871, 4,501,728, 4,837,028, and 5,019,369.

The compositions also include incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivoclearance.

In one embodiment, the present invention provides combined preparations. In one embodiment, "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

In one embodiment, it will be appreciated that the chimeras of the present invention can be provided to the individual with additional active agents to achieve an improved therapeutic effect as compared to treatment with each agent by itself. In another embodiment, measures (e.g., dosing and selection of the complementary agent) are taken to adverse side effects which are associated with combination therapies.

In one embodiment, depending on the severity and responsiveness of the condition to be treated, dosing can be of a single or a plurality of administrations, with course of treatment lasting from several days to several weeks or until cure is effected or diminution of the disease state is achieved.

In some embodiments, the peptides (e.g., chimeras) are administered in a therapeutically safe and effective amount. As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the presently described manner. In another embodiment, a therapeutically effective amount of the chimera is the amount of the chimera necessary for the in vivo measurable expected biological effect. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in Remington: The Science and Practice of Pharmacy, 21st Ed., Lippincott Williams & Wilkins, Philadelphia, Pa., (2005). In some embodiments, preparation of effective amount or dose can be estimated initially from in vitro assays. In one embodiment, a dose can be formulated in animal models and such information can be used to more accurately determine useful doses in humans.

In one embodiment, toxicity and therapeutic efficacy of the active ingredients described herein can be determined by standard pharmaceutical procedures in vitro, in cell cultures or experimental animals. In one embodiment, the data obtained from these in vitro and cell culture assays and animal studies can be used in formulating a range of dosage for use in human. In one embodiment, the dosages vary depending upon the dosage form employed and the route of administration utilized. In one embodiment, the exact formulation, route of administration and dosage can be chosen by the individual physician in view of the patient's condition. [See e.g., Fingl, et al., (1975) "The Pharmacological Basis of Therapeutics", Ch. 1 p.1].

Pharmaceutical compositions containing the presently described chimeric polypeptide as the active ingredient can be prepared according to conventional pharmaceutical compounding techniques. See, for example, Remington's Pharmaceutical Sciences, 18th Ed., Mack Publishing Co., Easton, Pa. (1990). See also, Remington: The Science and Practice of Pharmacy, 21st Ed., Lippincott Williams & Wilkins, Philadelphia, Pa. (2005).

In one embodiment, compositions including the preparation of the present invention formulated in a compatible pharmaceutical carrier are prepared, placed in an appropriate container, and labeled for treatment of an indicated condition.

In one embodiment, compositions of the present invention are presented in a pack or dispenser device, such as an FDA approved kit, which contain one or more unit dosage forms containing the active ingredient. In one embodiment, the pack, for example, comprises metal or plastic foil, such as a blister pack. In one embodiment, the pack or dispenser device is accompanied by instructions for administration. In one embodiment, the pack or dispenser is accommodated by a notice associated with the container in a form prescribed by a governmental agency regulating the manufacture, use or sale of pharmaceuticals, which notice is reflective of approval by the agency of the form of the compositions or human or veterinary administration. Such notice, in one embodiment, is labeling approved by the U.S. Food and Drug Administration for prescription drugs or of an approved product insert.

As used herein, the terms "subject" or "individual" or "animal" or "patient" or "mammal," refers to any subject, particularly a mammalian subject, for whom diagnosis, prognosis, or therapy is desired, for example, a human.

As used herein, the terms "treatment" or "treating" of a disease, disorder, or condition encompasses alleviation of at least one symptom thereof, a reduction in the severity thereof, or inhibition of the progression thereof. Treatment need not mean that the disease, disorder, or condition is totally cured. To be an effective treatment, a useful composition herein needs only to reduce the severity of a disease, disorder, or condition, reduce the severity of symptoms associated therewith, or provide improvement to a patient or subject's quality of life.

As used herein, the term "prevention" of a disease, disorder, or condition encompasses the delay, prevention, suppression, or inhibition of the onset of a disease, disorder, or condition. As used in accordance with the presently described subject matter, the term "prevention" relates to a process of prophylaxis in which a subject is exposed to the presently described peptides prior to the induction or onset of the disease/disorder process. This could be done where an individual has a genetic pedigree indicating a predisposition toward occurrence of the disease/disorder to be prevented. For example, this might be true of an individual whose ancestors show a predisposition toward certain types of, for example, inflammatory disorders. The term "suppression" is used to describe a condition wherein the disease/disorder process has already begun but obvious symptoms of the condition have yet to be realized. Thus, the cells of an individual may have the disease/disorder but no outside signs of the disease/disorder have yet been clinically recognized. In either case, the term prophylaxis can be applied to encompass both prevention and suppression. Conversely, the term "treatment" refers to the clinical application of active agents to combat an already existing condition whose clinical presentation has already been realized in a patient.

As used herein, the term "condition" includes anatomic and physiological deviations from the normal that constitute an impairment of the normal state of the living animal or one of its parts, that interrupts or modifies the performance of the bodily functions.

Any concentration ranges, percentage range, or ratio range recited herein are to be understood to include concentrations, percentages or ratios of any integer within that range and fractions thereof, such as one tenth and one hundredth of an integer, unless otherwise indicated.

Any number range recited herein relating to any physical feature, such as polymer subunits, size or thickness, are to be understood to include any integer within the recited range, unless otherwise indicated.

Use of the Compositions

According to some aspects, there is provided a method comprising the step of: attaching at least one peptide derived from amino acids 130 to 199 of SEQ ID NO: 1, wherein said peptide is devoid of: (a) a fragment comprising amino acids 1 to 129, (b) a fragment comprising amino acids 200 to 270, to a protein of interest, thereby producing a chimera comprising the protein of interest.

In some embodiments, the method is for extending a biological half-life of the protein of interest. In some embodiments, the method is for increasing a biological effect of the protein of interest. In some embodiments, the method is for reducing a dosing frequency of the protein of interest. In some embodiments, the method is for reducing a dosage of a protein of interest. In some embodiments, the method is for reducing a dosing frequency, reducing a dosage or both of the protein of interest. In some embodiments, the method is for increasing compliance of the protein of interest.

In some embodiments, the invention provides a method of extending a biological half-life of a protein of interest, comprising the step of: attaching at least one peptide derived from amino acids 130 to 199 of SEQ ID NO: 1, wherein said peptide is devoid of: (a) a fragment comprising amino acids 1 to 129, (b) a fragment comprising amino acids 200 to 270, to a protein of interest, thereby producing a chimera comprising the protein of interest with extended biological half-life compared to the protein of interest itself (unmodified protein of interest).

In another embodiment, the present invention further provides a method of improving the area under the curve (AUC) of a protein of interest, comprising the step of attaching at least one peptide derived from amino acids 130 to 199 of SEQ ID NO: 1, wherein said peptide is devoid of: (a) a fragment comprising amino acids 1 to 129, (b) a fragment comprising amino acids 200 to 270, to a protein of interest, thereby improving the area under the curve (AUC) of a protein of interest.

In some embodiments, the invention provides a method of reducing a dosing frequency of a protein of interest, the method comprises the step of attaching at least one peptide derived from amino acids 130 to 199 of SEQ ID NO: 1, wherein said peptide is devoid of: (a) a fragment comprising amino acids 1 to 129, (b) a fragment comprising amino acids 200 to 270, to a protein of interest, thereby reducing a dosing frequency of said protein of interest.

In another embodiment, the present invention further provides a method of increasing compliance in the use of peptide therapy, comprising: providing to a subject in need thereof, a chimera comprising a protein of interest attached to at least one peptide derived from amino acids 130 to 199 of SEQ ID NO: 1, wherein said peptide is devoid of: (a) a fragment comprising amino acids 1 to 129, (b) a fragment comprising amino acids 200 to 270, thereby increasing compliance in the use of a peptide therapy.

According to some aspects, the invention provides a method of treating or reducing a disease treatable or reducible by a protein of interest or a pharmaceutical formulation comprising the same, in a subject, the method comprises the step of administering to a subject a therapeutically effective amount of a chimera comprising a protein of interest and at least one peptide derived from NKp44, thereby treating or reducing a disease treatable or reducible by the protein of interest in a subject.

According to another embodiment, the method comprises administering to a subject in need thereof an effective amount of the chimeras of the invention or the pharmaceutical composition comprising same in a smaller dosage than needed when using the protein of interest that was not modified by the teaching of the instant invention. As used herein the term "dosage" refers to the size, frequency, and number of doses to be administered to a subject in need thereof. According to another embodiment, the method comprises administering to the subject in need thereof an effective amount of the chimeras of the invention or the pharmaceutical composition comprising same in less frequency than needed when using the protein of interest that was not modified by the teaching of the instant invention.

According to another embodiment, the method comprises administering to the subject in need thereof an effective amount of the chimeras of the invention or the pharmaceutical composition comprising same in smaller dose than needed when administering a therapeutic protein of interest which is not fused to the peptides of the present invention. As used herein the term "dose" relates to the quantity/amount of a therapeutic active agent (e.g., the chimera of the invention) to be administered at one time. In another embodiment, there is provided use of the chimera of the present invention or a composition comprising the chimera, for the preparation of a medicament for treating a condition that can be treated with the protein of interest in a subject in need thereof.

In another embodiment, there is provided use of the chimera of the present invention or a composition comprising the chimera, for the preparation of a medicament for treating a condition that can be treated with the protein of interest in a subject in need thereof.

In another embodiment, the invention provides the chimera of the present invention or the composition comprising the chimera for use in treating or reducing a condition treatable or reducible by the protein of interest in a subject in need thereof.

In another embodiment, the chimera of the instant invention is used to facilitate organ transplantation. In another embodiment, the chimera of the instant invention is used to reduce inflammation. In another embodiment, the chimera of the instant invention is used to induce erythropoiesis. In another embodiment, the chimera of the instant invention is used to induce growth. In another embodiment, the chimera of the instant invention is used to induce weight gain. In another embodiment, the chimera of the instant invention is used to reduce weight gain. In another embodiment, the chimera of the instant invention is used in cancer therapy as will be readily understood by one of ordinary skill in the art. In another embodiment, the chimera of the instant invention is used to induce an immune response. In another embodiment, the chimera of the instant invention is used in infectious disease therapy as will be readily understood by one of ordinary skill in the art. In another embodiment, the infectious disease is selected from the group consisting of: a parasitic infection, bacterial infection, fungal infection, and viral infection. In another embodiment, the chimera of the instant invention is used in bacterial infection therapy. In another embodiment, the chimera of the instant invention is used in viral infection therapy. In another embodiment, the viral infection is inflicted by a virus of a viral family selected from the group consisting of: Adenoviridae, Papillomaviridae, Polyomaviridae, Herpesviridae, Poxviridae, Hepadnaviridae, Parvoviridae, Astroviridae, Caliciviridae and Picornaviridae, Coronoviridae, Flaviviridae, Retroviridae, Togaviridae, Arenaviridae, Bunyaviridae, Filoviridae, Orthomyxoviridae, Paramyxoviridae and Rhabdoviridae, Reoviridae, Anelloviridae, and Hepatitis D virus. In another embodiment, the chimera of the instant invention is used in treating allergy as will be readily understood by one of ordinary skill in the art.

As used herein "cancer" or "pre-malignancy" are diseases associated with cell proliferation. Non-limiting types of cancer include carcinoma, sarcoma, lymphoma, leukemia, blastoma and germ cells tumors. In one embodiment, carcinoma refers to tumors derived from epithelial cells including but not limited to breast cancer, prostate cancer, lung cancer, pancreas cancer, and colon cancer. In one embodiment, sarcoma refers of tumors derived from mesenchymal cells including but not limited to sarcoma botryoides, chondrosarcoma, ewings sarcoma, malignant hemangioendothelioma, malignant schwannoma, osteosarcoma and soft tissue sarcomas. In one embodiment, lymphoma refers to tumors derived from hematopoietic cells that leave the bone marrow and tend to mature in the lymph nodes including but not limited to hodgkin lymphoma, non-hodgkin lymphoma, multiple myeloma and immunoproliferative diseases. In one embodiment, leukemia refers to tumors derived from hematopoietic cells that leave the bone marrow and tend to mature in the blood including but not limited to acute lymphoblastic leukemia, chronic lymphocytic leukemia, acute myelogenous leukemia, chronic myelogenous leukemia, hairy cell leukemia, T-cell prolymphocytic leukemia, large granular lymphocytic leukemia and adult T-cell leukemia. In one embodiment, blastoma refers to tumors derived from immature precursor cells or embryonic tissue including but not limited to hepatoblastoma, medulloblastoma, nephroblastoma, neuroblastoma, pancreatoblastoma, pleuropulmonary blastoma, retinoblastoma and glioblastoma-multiforme. In one embodiment, germ cell tumors refers to tumors derived from germ cells including but not limited to germinomatous or seminomatous germ cell tumors (GGCT, SGCT) and nongerminomatous or nonseminomatous germ cell tumors (NGGCT, NSGCT). In one embodiment, germinomatous or seminomatous tumors include but not limited to germinoma, dysgerminoma and seminoma. In one embodiment, nongerminomatous or non-seminomatous tumors refers to pure and mixed germ cells tumors including but not limited to embryonal carcinoma, endodermal sinus tumor, choriocarcinoma, tearoom, polyembryoma, gonadoblastoma and teratocarcinoma.

Use of Growth Hormones of the Invention

In another embodiment, chimeras comprising growth hormones as taught by the instant invention include constructs comprising a signal peptide. In another embodiment, chimeras comprising growth hormones as taught by the instant invention include truncated constructs. Non-limiting exemplary chimeras comprising growth hormones as taught by the instant invention are set forth in SEQ ID NOs: 16 to 18.

In another embodiment, chimeras comprising growth hormones, as taught by the instant invention, stimulate body growth by stimulating the liver and other tissues to secrete IGF-I. In another embodiment, IGF-I stimulates proliferation of chondrocytes, resulting in bone growth.

In another embodiment, chimeras comprising growth hormones, as taught by the instant invention, induce metabolic effects on protein, lipid and carbohydrate metabolism. In another embodiment, chimeras comprising growth hormones, as taught by the instant invention, have a direct effect. In another embodiment, chimeras comprising growth hormones as taught by the instant invention stimulate fat metabolism. In another embodiment, chimeras comprising growth hormones as taught by the instant invention stimulate the utilization of fat by stimulating triglyceride breakdown and oxidation in adipocytes. In another embodiment, chimeras comprising growth hormones, as taught by the instant invention, have an indirect effect through induction of IGF-I. In another embodiment, chimeras comprising growth hormones, as taught by the instant invention, stimulate carbohydrate metabolism. In another embodiment, chimeras comprising growth hormones, as taught by the instant invention, maintain blood glucose within a normal range. In another embodiment, chimeras comprising growth hormones, as taught by the instant invention, comprise an anti-insulin activity. In another embodiment, chimeras comprising growth hormones, as taught by the instant invention, suppress the abilities of insulin to stimulate uptake of glucose in peripheral tissues and enhance glucose synthesis in the liver. In another embodiment, chimeras comprising growth hormones, as taught by the instant invention, stimulate insulin secretion, leading to hyperinsulinemia.

In another embodiment, chimeras comprising growth hormones, as taught by the instant invention, stimulate protein anabolism in a tissue. In another embodiment, chimeras comprising growth hormones, as taught by the instant invention, stimulate amino acid uptake, increased protein synthesis, and decreased oxidation of proteins.

In another embodiment, chimeras comprising growth hormones, as taught by the instant invention, are used to compensate for limited or no production of growth hormone in a subject. In another embodiment, chimeras comprising growth hormones, as taught by the instant invention, compensate for limited or no production of growth hormone-releasing hormone (GHRH). In another embodiment, chimeras comprising growth hormones, as taught by the instant invention, compensate for the increased activity of somatostatin. In another embodiment, chimeras comprising growth hormones, as taught by the instant invention, compensate for limited or no production of ghrelin.

In another embodiment, chimeras comprising growth hormones, as taught by the instant invention, are used to treat diseases associated with lesions in either the hypothalamus, the pituitary, or in target cells. In another embodiment, chimeras comprising growth hormones, as taught by the instant invention, are used to treat diseases associated with reduced target cell's response to the hormone.

In another embodiment, chimeras comprising growth hormones, as taught by the instant invention, are used to treat children with severe growth retardation. In another embodiment, chimeras comprising growth hormones, as taught by the instant invention, are used to treat children of pathologically short stature. In another embodiment, chimeras comprising growth hormones, as taught by the instant invention, are used to enhance athletic performance. In another embodiment, chimeras comprising growth hormones, as taught by the instant invention, are used to treat symptoms of aging. In another embodiment, chimeras comprising growth hormones, as taught by the instant invention, are used to treat cosmetic symptoms of aging.

In another embodiment, chimeras comprising growth hormones, as taught by the instant invention, are used for enhancing milk production in a female subject. In another embodiment, chimeras comprising cow growth hormones, as taught by the instant invention, is used for enhancing milk production in dairy cattle. In another embodiment, chimeras comprising animal growth hormones, as taught by the instant invention, are used in animal agriculture technology. In another embodiment, chimeras comprising farm animal growth hormones, as taught by the instant invention, are used for enhancing growth of farm animal such as, but not limited to, pigs.

Use of Chorionic Gonadotropins of the Invention

In another embodiment, chimeras comprising chorionic gonadotropins (CG), as taught by the instant invention, include constructs comprising a signal peptide. In another embodiment, chimeras comprising CG, as taught by the instant invention, include truncated constructs. In another embodiment, the CG is a human chorionic gonadotropin (hCG). Non-limiting exemplary sequences of a chimera comprising hCG, as taught by the instant invention, is set forth in SEQ ID NO: 13.

In another embodiment, chimeras comprising CG, as taught by the instant invention, are used to compensate for limited or no production of chorionic gonadotropin in a subject. In another embodiment, chimeras comprising CG, as taught by the instant invention, are used in treating infertility in mammals. In another embodiment, chimeras comprising hCG, as taught by the instant invention, are used in treating infertility in humans. In another embodiment, chimeras comprising hCG, as taught by the instant invention, induce menstruation in mammals such as human. In another embodiment, chimeras comprising hCG, as taught by the instant invention, trigger ovulation. In another embodiment, chimeras comprising hCG, as taught by the instant invention, improve endometrial thickness during ovarian stimulation. In another embodiment, chimeras comprising hCG, as taught by the instant invention, are used in conjunction with other hormones such as LH and/or FSH. In another embodiment, chimeras comprising hCG, as taught by the instant invention, reduce symptoms of testosterone deficiency. In another embodiment, chimeras comprising hCG, as taught by the instant invention, when administered with testosterone and/or anastrozole reduce symptoms of testosterone deficiency.

In another embodiment, chimeras comprising hCG, as taught by the instant invention, are used in controlling or treating a viral infection. In another embodiment, the viral infection is a retroviral infection. In another embodiment, chimeras comprising CG, as taught by the instant invention, are used in controlling or treating a human immunodeficiency virus (HIV) infection and other virus-related immunodeficiency disorders. As used herein the term "control" means to diminish, ameliorate, or stabilize the infection and/or any other existing unwanted condition or side effect caused by the virus.

In another embodiment, chimeras comprising hCG, as taught by the instant invention, are used in treating and/or ameliorating neurodegenerative disease or condition (e.g., Alzheimer's disease or other dimentia, multiple sclerosis (MS), schizophrenia, macular degeneration, glaucoma, diabetic retinopathy, peripheral neuropathy, Huntington's disease, amyotrophic lateral sclerosis, and Parkinson's disease, CNS injuries which include, for example, cerebrovascular events like strokes). As used herein the term "treating and/or ameliorating" mean the reduction or complete removal of one or more symptoms (including neurologic symptoms or behavioral performance) of a disease or medical condition. Such treatment or amelioration can include the delay or elimination of the onset of one or more symptoms when administered to a person at risk for the disease or medical condition. Tests for the success of treatment or amelioration are well known in the art.

In another embodiment, chimeras comprising hCG, as taught by the instant invention, induce metabolic effects on protein, lipid and/or carbohydrate metabolism. In another embodiment, chimeras comprising hCG, as taught by the instant invention, have a direct effect. In another embodiment, chimeras comprising hCG, as taught by the instant invention, are used in treating type 2 diabetes mellitus. In another embodiment, chimeras comprising hCG, as taught by the instant invention, are used with one or more antidiabetic agents (e.g., insulin, alpha glucosidase inhibitors etc.) in treating type 2 diabetes mellitus.

In another embodiment, chimeras comprising hCG, as taught by the instant invention, are used in treating malignancies. In another embodiment, chimeras comprising hCG, as taught by the instant invention, are used in treating breast cancer. In another embodiment, chimeras comprising hCG, as taught by the instant invention, are used in treating mammary tumors.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a," "an" and "at least one" are used interchangeably in this application.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In the description and claims of the present application, each of the verbs, "comprise," "include" and "have" and conjugates thereof, are used to indicate that the object or objects of the verb are not necessarily a complete listing of components, elements, or parts of the subject or subjects of the verb.

Other terms as used herein are meant to be defined by their well-known meanings in the art.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Strategies for Protein Purification and Characterization—A Laboratory Course Manual" CSHL Press (1996); "Bacteriophage Methods and Protocols", Volume 1: Isolation, Characterization, and Interactions, all of which are incorporated by reference. Other general references are provided throughout this document.

Various embodiments and aspects of the present invention as delineated hereinabove and as claimed in the claims section below find experimental support in the following examples. Reference is now made to the following examples, which together with the above descriptions illustrate some embodiments of the invention in a non-limiting fashion.

Materials and Methods hCG-β and hGH variants: Amino acid sequences used for construction of hCG-β-44 tail variant (SEQ ID NO: 13), and control variants are listed in table 2 and 3.

TABLE 2 amino acid sequences for construction of hCG-β variants.

| SEQ ID NO: | Name | Description | Sequence |
|---|---|---|---|
| 2 | 44 tail | AA 130-199 of NKp44 | SPASASTQTSWTPRDLVSSQTQTQSCVPPTAGARQ APESPSTIPVPSHPSSPLPVPLPSRPQNSTLRPGP |
| 6 | Strep tag | | WSHPQFEK |
| 8 | hCG-β Leader peptide | First 24 amino acids of hCG-β | MEMFQGLLLLLLLSMGGTWASKEP |
| 9 | (UniProt entry number: P0DN86) | | MEMFQGLLLLLLLSMGGTWASKEPLRPRCRPINA TLAVEKEGCPVCITVNTTICAGYCPTMTRVLQGVL PALPQVVCNYRDVRFESIRLPGCPRGVNPVVSYAV ALSCQCALCRRSTTDCGGPKDHPLTCDDPRFQDSS SSKAPPPSLPSPSRLPGPSDTPILPQ |

TABLE 2-continued amino acid sequences for construction of hCG-β variants.

| SEQ ID NO: | Name | Description | Sequence |
|---|---|---|---|
| 10 | hCG-β-WT with strep-tag | Strep tag is located between amino acids 24 and 25 of hCG-β | MEMFQGLLLLLLLSMGGTWASKEP*WSHPQFEK*LRPRCRPINATLAVEKEGCPVCITVNTTICAGYCPTMTRVLQGVLPALPQVVCNYRDVRFESIRLPGCPRGVNPVVSYAVALSCQCALCRRSTTDCGGPKDHPLTCDDPRFQDSSSSKAPPPSLPSPSRLPGPSDTPILPQ |
| 11 | hCG-β-ΔCTP | Amino acids 1-136 of hCG-β | MEMFQGLLLLLLLSMGGTWASKEPLRPRCRPINATLAVEKEGCPVCITVNTTICAGYCPTMTRVLQGVLPALPQVVCNYRDVRFESIRLPGCPRGVNPVVSYAVALSCQCALCRRSTTDCGGPKDHPLTCDDPRFQD |
| 12 | hCG-β-ΔCTP with strep tag | Amino acids 1-136 of hCG-β with strep-tag | MEMFQGLLLLLLLSMGGTWASKEP*WSHPQFEK*LRPRCRPINATLAVEKEGCPVCITVNTTICAGYCPTMTRVLQGVLPALPQVVCNYRDVRFESIRLPGCPRGVNPVVSYAVALSCQCALCRRSTTDCGGPKDHPLTCDDPRFQD |
| 13 | hCG-β3-44 tail variant | SEQ ID NO: 11 having a peptide derived from NKp44 (SEQ ID NO: 2) attached to its carboxy terminus. | MEMFQGLLLLLLLSMGGTWASKEP*WSHPQFEK*LRPRCRPINATLAVEKEGCPVCITVNTTICAGYCPTMTRVLQGVLPALPQVVCNYRDVRFESIRLPGCPRGVNPVVSYAVALSCQCALCRRSTTDCGGPKDHPLTCDDPRFQDSPASASTQTSWTPRDLVSSQTQTQSCVPPTAGARQAPESPSTIPVPSHPSSPLPVPLPSRPQNSTLRPGP |

TABLE 3

Amino acid sequences for construction of hGH variants.

| SEQ ID NO: | Name | Description | Sequence |
|---|---|---|---|
| 2 | 44 tail | AA 130-199 of NKp44 | SPASASTQTSWTPRDLVSSQTQTQSCVPPTAGARQAPESPSTIPVPSHPSSPLPVPLPSRPQNSTLRPGP |
| 5 | 44 tail NA | AA 130-199 of NKp44 (N to A substitution) | SPASASTQTSWTPRDLVSSQTQTQSCVPPTAGARQAPESPSTIPVPSHPSSPLPVPLPSRPQASTLRPGP |
| 3 | SPA sequence | | SPASASTQTSWTPRDLVSSQTQTQSCVPPTAGAR |
| 4 | APE sequence | | QAPESPSTIPVPSHPSSPLPVPLPSRPQNSTLRPGP |
| 7 | His tag | | HHHHHHHH |
| 15 | hGH | Uniprot entry number: P01241 | MATGSRTSLLLAFGLLCLPWLQEGSAFPTIPLSRLFDNAMLRAHRLHQLAFDTYQEFEEAYIPKEQKYSFLQNPQTSLCFSESIPTPSNREETQQKSNLELLRISLLLIQSWLEPVQFLRSVFANSLVYGASDSNVYDLLKDLEEGIQTLMGRLEDGSPRTGQIFKQTYSKFDTNSHNDDALLKNYGLLYCFRKDMDKVETFLRIVQCRSVEGSCGF |
| 16 | Amino acids 27-217 of hGH | | FPTIPLSRLFDNAMLRAHRLHQLAFDTYQEFEEAYIPKEQKYSFLQNPQTSLCFSESIPTPSNREETQQKSNLELLRISLLLIQSWLEPVQFLRSVFANSLVYGASDSNVYDLLKDLEEGIQTLMGRLEDGSPRTGQIFKQTYSKFDTNSHNDDALLKNYGLLYCFRKDMDKVETFLRIVQCRSVEGSCGF |
| 17 | Native GH leader peptide | | MATGSRTSLLLAFGLLCLPWLQEGSQA |
| 18 | Flag tag | | DYKDHDGDYKDHDIDYKDDDDK |
| 19 | hGH-with leader and flag | A Flag tag (SEQ ID NO: 18) is inserted following leader peptide (SEQ ID NO: 17) | MATGSRTSLLLAFGLLCLPWLQEGSADYKDHDGDYKDHDIDYKDDDDKFPTIPLSRLFDNAMLRAHRLHQLAFDTYQEFEEAYIPKEQKYSFLQNPQTSLCFSESIPTPSNREETQQKSNLELLRISLLLIQSWLEPVQFLRSVFANSLVYGASDSNVYDLLKDLEEGIQTLMGRLEDGSPRTGQIFKQT |

TABLE 3-continued

Amino acid sequences for construction of hGH variants.

| SEQ ID NO: | Name | Description | Sequence |
|---|---|---|---|
| | | between amino acids 26 and 27 of hGH. | YSKFDTNSHNDDALLKNYGLLYCFRKDMDKVETFLRI VQCRSVEGSCGF |
| 20 | hGH-wt with flag and His tag | hGH A Flag tag (SEQ ID NO: 18) is inserted following leader peptide (SEQ ID NO: 17) between amino acids 26 and 27 and a His tag (SEQ ID NO: 7) is attached to its carboxy terminus. | MATGSRTSLLLAFGLLCLPWLQEGSADYKDHDGDYK DHDIDYKDDDDKFPTIPLSRLFDNAMLRAHRLHQLAF DTYQEFEEAYIPKEQKYSFLQNPQTSLCFSESIPTPSNRE ETQQKSNLELLRISLLLIQSWLEPVQFLRSVFANSLVYG ASDSNVYDLLKDLEEGIQTLMGRLEDGSPRTGQIFKQT YSKFDTNSHNDDALLKNYGLLYCFRKDMDKVETFLRI VQCRSVEGSCGFHHHHHHHH |
| 21 | hGH-44 tail variant | | MATGSRTSLLLAFGLLCLPWLQEGSADYKDHDGDYK DHDIDYKDDDDKFPTIPLSRLFDNAMLRAHRLHQLAF DTYQEFEEAYIPKEQKYSFLQNPQTSLCFSESIPTPSNRE ETQQKSNLELLRISLLLIQSWLEPQFLRSVFANSLVYGA SDSNVYDLLKDLEEGIQTLMGRLEDGSPRTGQIFKQTY SKFDTNSHNDDALLKNYGLLYCFRKDMDKVETFLRIV QCRSVEGSCGFSPASASTQTSWTPRDLVSSQTQTQSC VPPTAGARQAPESPSTIPVPSHPSSPLPVPLPSRPQNS TLRPGPHHHHHHHH |
| 24 | hGH-44 tail-NA | | MATGSRTSLLLAFGLLCLPWLQEGSADYKDHDGDYK DHDIDYKDDDDKFPTIPLSRLFDNAMLRAHRLHQLAF DTYQEFEEAYIPKEQKYSFLQNPQTSLCFSESIPTPSNRE ETQQKSNLELLRISLLLIQSWLEPVQFLRSVFANSLVYG ASDSNVYDLLKDLEEGIQTLMGRLEDGSPRTGQIFKQT YSKFDTNSHNDDALLKNYGLLYCFRKDMDKVETFLRI VQCRSVEGSCGFSPASASTQTSWTPRDLVSSQTQTQS CVPPTAGARQAPESPSTIPVPSHPSSPLPVPLPSRPQA STLRPGPHHHHHHHH |
| 33 | APE variant | | MATGSRTSLLLAFGLLCLPWLQEGSAFPTIPLSRLFDN AMLRAHRLHQLAFDTYQEFEEAYIPKEQKYSFLQNPQ TSLCFSESIPTPSNREETQQKSNLELLRISLLLIQSWLEP VQFLRSVFANSLVYGASDSNVYDLLKDLEEGIQTLMG RLEDGSPRTGQIFKQTYSKFDTNSHNDDALLKNYGLL YCFRKDMDKVETFLRIVQCRSVEGSCGFQAPESPSTIP VPSHPSSPLPVPLPSRPQNSTLRPGPHHHHHHHH |
| 30 | SPA variant | | MATGSRTSLLLAFGLLCLPWLQEGSAFPTIPLSRLFDN AMLRAHRLHQLAFDTYQEFEEAYIPKEQKYSFLQNPQ TSLCFSESIPTPSNREETQQKSNLELLRISLLLIQSWLEP VQFLRSVFANSLVYGASDSNVYDLLKDLEEGIQTLMG RLEDGSPRTGQIFKQTYSKFDTNSHNDDALLKNYGLL YCFRKDMDKVETFLRIVQCRSVEGSCGFSPASASTQTS WTPRDLVSSQTQTQSCVPPTAGARHHHHHHHH |
| 27 | SPA-SPA variant | | MATGSRTSLLLAFGLLCLPWLQEGSASPASASTQTSW TPRDLVSSQTQTQSCVPPTAGARFPTIPLSRLFDNAM LRAHRLHQLAFDTYQEFEEAYIPKEQKYSFLQNPQTSL CFSESIPTPSNREETQQKSNLELLRISLLLIQSWLEPVQF LRSVFANSLVYGASDSNVYDLLKDLEEGIQTLMGRLE DGSPRTGQIFKQTYSKFDTNSHNDDALLKNYGLLYCF RKDMDKVETFLRIVQCRSVEGSCGFSPASASTQTSWT PRDLVSSQTQTQSCVPPTAGARHEIHHHHHH |

Production of hGH variants: Suspended HEK293F cells were transiently transfected with a plasmid encoding the chimeric peptide variant using a transfection reagent (GeneTran transfection reagent purchased from Biomiga) in order to produce secreted SPA-SPA hGH variant. The secreted SPA-SPA hGH variant was purified from the suspension medium by using a Fast protein liquid chromatography (FPLC).

Injection of GH derived variants, and serum purification: 5 rat groups were used: Biotropin group 50 ug/ml (2.26 uM), Biotropin group 100 ug/ml (4.52 uM), SPA-SPA group (2.26 uM), SPA-SPA group (4.52 uM), Saline group. (n=3). Rats were weighted prior to injection. Next rats were anaesthetized using Isoflurane 3% and 0.45 ml of each injection variant was injected to its group subcutaneously (SC). Rats were supplied with water and food during the experiment.

Serum purification: A 450 or 250 microliters blood sample were collected from caudal artery into 0.5 ml protein LoBind tube. Collected sample was incubated for 30 minutes at room temperate (RT) to allow blood clotting. Next blood was centrifuged at 3,000 g for 5 min, 4° C. and the serum was transferred into a new 0.5 ml LoBind tube. The serum samples were kept in −20° C. until tested. Blood samples were collected into prior to injection and 2 hr, 4 hr, 8 hr, 12 hr, and 24 hr post injection. (2 hr and 4 hr following injection, 250 ul of blood was collected. Prior to injection and 8 hr, 12 hr and 24 hr following injection 450 ul of blood was collected, since higher levels of serum are needed for detection).

hGH derived protein measurement: The samples were thawed on ice for 30min, vortexed briefly and spined down at 4° C. Next, dilution for measuring the serum samples were made: (optimal volume of the diluted sample should be at least 200 ul). For the 2 hr and 4 hr time point samples: The serum sample was diuted 1:2 with dilution buffer. For the 0, 8 hr 12 hr 24 hr and 48 hr time point samples, there was no need to dilute the serum sample as the samples need to be more concentrated due to the degradation of the proteins. Next, the GH levels are measured using Immulite 2000 device, and the amount of the hGH detected for each sample was calculated. Further, the average result for each time point in each injected protein was calculated. The number of moles of each injected protein that is present in the serum of the rat was calculated using the results received from the Immulite 2000 device.

For example: Biotropin 2.26 uM at the second time point showed result of 7.09 ng/ml in serum sample: 7.09 ng -1 ml serum. As the volume of the rat's blood (in a rat with a weight of 400 gr) is approximately 25.5 ml, the serum volume is ~50%-60% of the bloods volume, meaning the serum volume is ~13.5 ml. In the first time point ~300 ul of serum was collected, meaning there was left ~13.2 ml.
serum7.09 ng-1 ml serum
Xng-13.5 ml serum
X=(7.09 ng*13.5 ml)/1 ml=95.7 ng
There is 95.7 ng of hGH in the whole serum of the mouse body.
As Biotropin MW is 22126Da:
22129 gr-1 mol
22129 ngr-1 nmol
95.7 ngr-Xnmol
X=(95.7 ngr*1 nmol)/22129 ngr=0.0043 nmol=4.327 pmol.
There is 4.327 pmol in the whole mouse body at the second time point.
Injection dose (ug/kg) calculated based on the molar concentration calculated on stef 7.4: 400 gr rat is injected with 400 ul of 74.4 ug/ml solution:
1 ml-74.4 ug
0.4 ml-X
X=(0.4 ml*74.4 ug)/1 ml=29.76 ug
injection of 29.76 ug to weight of 0.4 kg, thus:
0.4 kg-29.76 ug
1 kg-X
X=(1 kg*29.76 ug)/0.4 kg=74.4 ug
For 2.26 uM of SPA-SPA the injection dose was 74.4 ug/kg.
For 4.52 uM of SPA-SPA the injection dose was 149 ug/kg.

Pharmacokinetic parameters: In order to calculate the pharmacokinetic parameters PLSolver (Excel Add-on) was used. To get better understanding whether the t1/2 is influenced by the injected dose—Injection dose/t1/2 ratio was calculated.

Example 1

A Chimera of hCG-β and a Peptide Derived from NKp44 Exhibits Extended Serum Half-Life A chimera of hCG-β attached to a peptide derived from NKp44 (hCG-β-44 tail variant) was produced to evaluate the effect of peptides derived from NKp44 on serum half-life.

The serum half-life of the hCG-β-44tail variant with a strep tag (SEQ ID NO:13) in rat plasma was evaluated compared to hCG-β-WT with a strep tag (SEQ ID NO: 10), and to hCG-β-ΔCTP with a strep tag (SEQ ID NO: 12). The different proteins were injected into Sprague Dawley rats. As demonstrated in FIG. 1, the hCG-β-44tail with strep tag variant demonstrates higher plasma concentration than hCG-β-WT with strep tag and hCG-β-ΔCTP with strep tag. This result demonstrates the ability of the peptides derived from NKp44 of the invention to extend serum half-life of hCG-β (FIG. 1).

Example 2

A Chimera of hGH and a Peptide Derived from NKp44 Exhibits Extended Serum Half-Life Chimeras of human growth hormone (hGH) attached to a peptide derived from NKp44 of the invention were produced to evaluate the effect of the peptides derived from NKp44 on serum half-life.

Figure 2A:
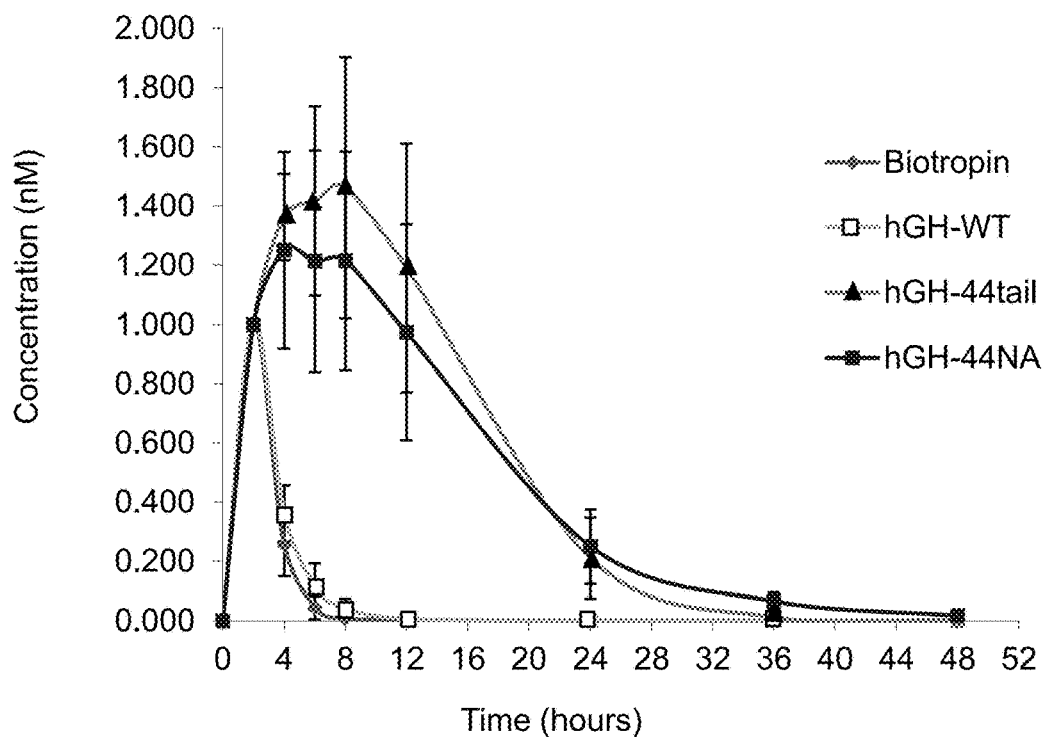
FIG. 2A is a graph illustrating changes of hGH-derived proteins concentration (nM) in rat's serum, over time.
Figure 2B:
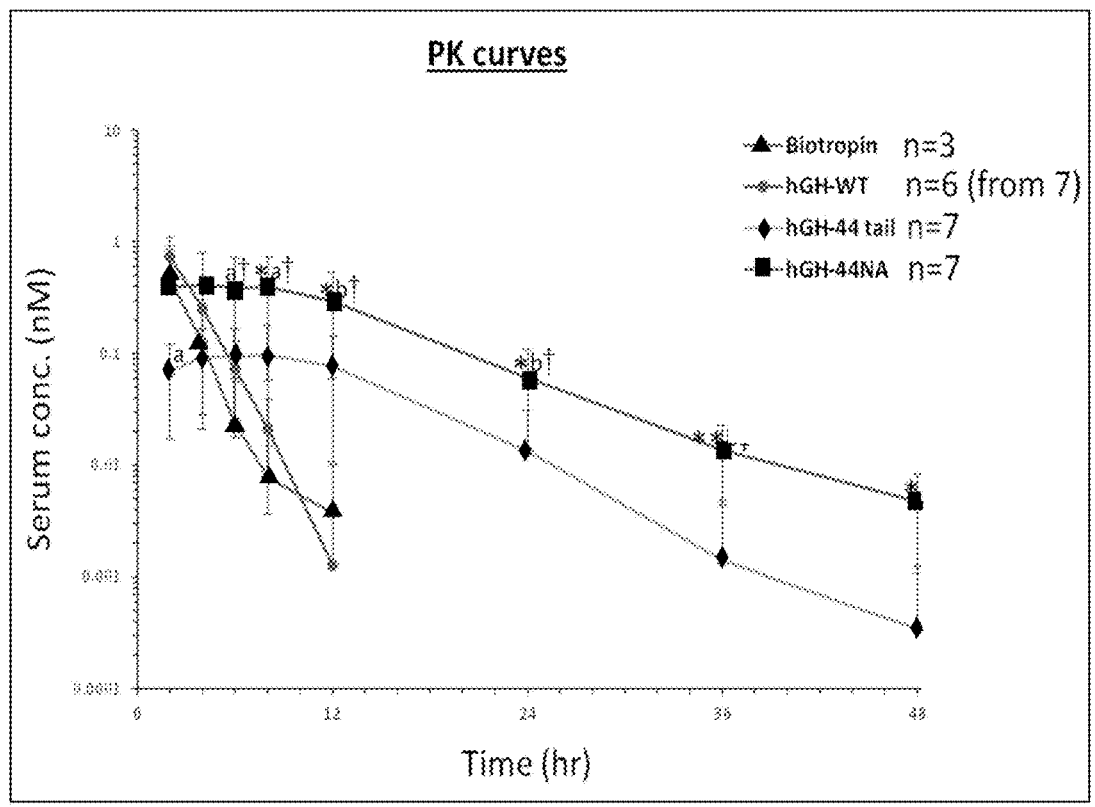
FIG. 2B is a graph showing changes of hGH-derived proteins concentration (nM) in rat's serum, over time, the concentrations are normalized to the levels of the drug on the first measurement following injection.

In order to evaluate whether the chimeras exhibit extended serum half-life, the different proteins, hGH-WT with flag (SEQ ID NO: 20), hGH-44tail (SEQ ID NO: 21), and hGH-44tail-NA (SEQ ID NO: 24), each having a His tag at the carboxy terminus to allow detection of the protein, were injected into Sprague Dawley rats. As demonstrated in FIG. 2, the chimeras demonstrate higher plasma concentration than wild type hGH (SEQ ID NO: 20). These results demonstrate the ability of the peptides derived from NKp44 of the invention to extend serum half-life of hGH (FIG. 2A-B).

Example 3

Pharmacokinetic Properties of the SPA-SPA and the SPA Variants of hGH

The pharmacokinetic properties of an SPA-SPA variant of hGH (SEQ ID NO: 27) which was produced according to the instant invention were compared to a commercially available variant of hGH (Biotropin™). His tag (SEQ ID NO: 7) was added to the carboxy terminus of each tested variant in order to allow detection of the protein.

Figure 3A:
FIG. 3A is a time line illustration of the in vivo assay.

Sprague Dawley rats were injected with the protein SPA-SPA variant and Biotropin in 2 different concentrations. Saline was used as a negative control. Blood was collected at several time points (0, 2 hours (hr), 4 hr, 8 hr, 12 hr, 24 hr, and 48 hr) and serum was tested in order to detect hGH (FIG. 3A).

Figure 3B:
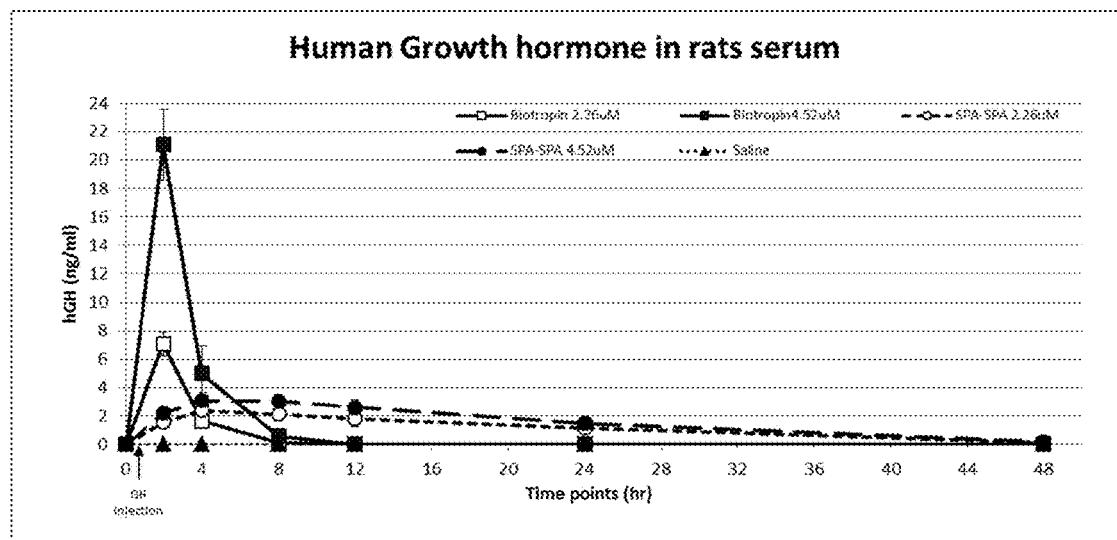
FIG. 3B is a graph illustrating the change in serum concentration of hGH (ng/ml) following subcutaneously (SC) injection of Bio-tropin, SPA-SPA variant, or saline to rats.
Figure 3C:
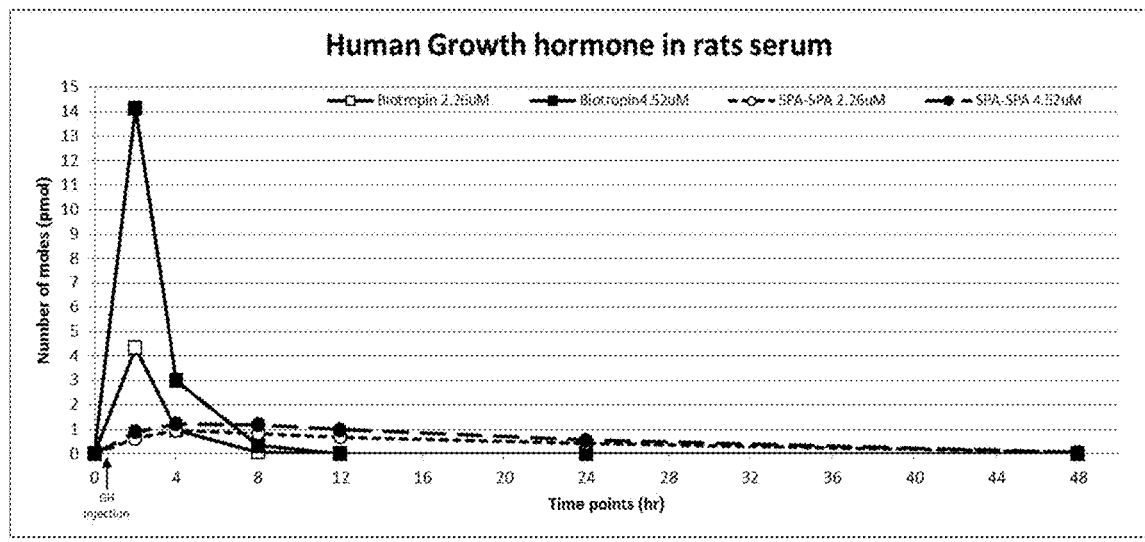
FIG. 3C is a graph showing the change in the number of moles (pmol) of human growth hormone (hGH) in rats' serum in time dependent manner, following subcutaneously (SC) injection of Bio-tropin, SPA-SPA variant, or saline to rats.

Biotropin concentration in the blood showed a fast increase immediately following injection, with a peak concentration reached 2 hours post injection for both of the injected concentrations. Following the 2-hour peak, Biotropin concentration sharply decreases, and hGH levels disappear. Biotropin becomes fully undetectable at 12hr post injection (Tables 4 and 5, and FIG. 3B-C).

In contrast to Biotropin, the SPA-SPA variant shows a slow and moderate increase. In both of the injection groups a peak of hGH concentration was achieved 4hr post injection. Following the 4-hour peak, the SPA-SPA variant is slowly decreased, but remains detectable even 48 hr post injection (Tables 4 and 5, and FIG. 3B-C).

Further results demonstrate that rats injected with 2.26 uM Biotropin presented a hGH peak of 7.09 ng/ml, while rats that were injected with 4.52 uM (twice as much) presented a peak of 21.09 ng/ml (3 times higher than the result in the 2.26 um group). In contrast, rats that were injected with 2.26 uM SPA-SPA variant presented a hGH peak of 2.39 ng/ml, while the rats injected with 4.52 uM (twice as much) presented a peak of 3.08 ng/ml (~1.3 times higher than the result in the 2.26 um group). One possible explanation for the low amount of SPA-SPA variant in the serum, could be a slow release of the peptide. Thus, it slowly accumulates until reaching its peak 4 hr after the injection, and then the peptide slowly is cleared.

TABLE 4

Mean result of hGH detected in rat serum (ng/ml).

| Time point (hr)/ Injected GH | 0 | 2 | 4 | 8 | 12 | 24 | 48 |
|---|---|---|---|---|---|---|---|
| Biotropin 2.26 uM | 0 | 7.09 | 1.64 | 0.13 | 0 | 0 | 0 |
| Biotropin 4.52 uM | 0 | 21.09 | 5.01 | 0.58 | 0 | 0 | 0 |
| SPA-SPA 2.26 uM | 0 | 1.53 | 2.39 | 2.12 | 1.79 | 1.16 | 0.13 |
| SPA-SPA 4.52 uM | 0 | 2.19 | 3.08 | 3.06 | 2.59 | 1.49 | 0.17 |
| Saline | 0 | 0 | 0 | 0 | 0 | 0 | 0 |

TABLE 5 hGH in rat total serum (pmol). Calculations are based on Table 4.

| Time point (hr)/ Injected GH | 0 | 2 | 4 | 8 | 12 | 24 | 48 |
|---|---|---|---|---|---|---|---|
| Biotropin 2.26 uM | 0 | 4.327 | 0.979 | 0.074 | 0 | 0 | 0 |
| Biotropin 4.52 uM | 0 | 14.155 | 2.990 | 0.338 | 0 | 0 | 0 |
| SPA-SPA 2.26 uM | 0 | 0.629 | 0.957 | 0.830 | 0.683 | 0.433 | 0.048 |
| SPA-SPA 4.52 uM | 0 | 0.897 | 1.235 | 1.197 | 0.990 | 0.555 | 0.062 |

Figure 4A:
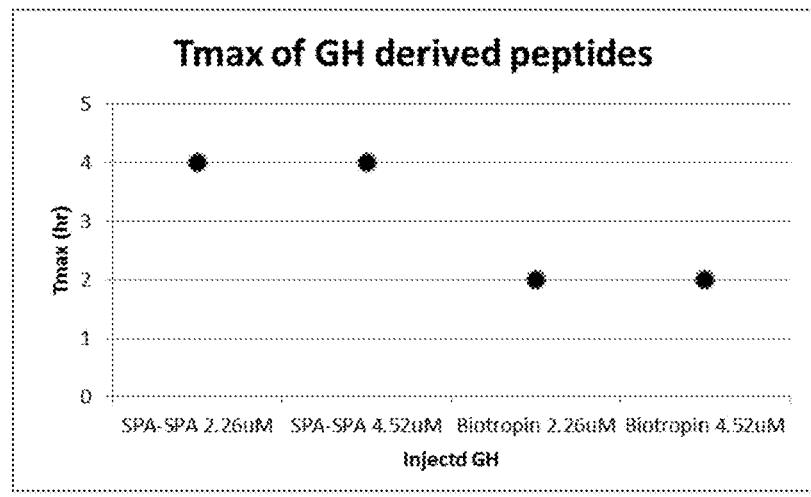
FIGS. 4A-4C are graphs comparing pharmacokinetic parameters: Tmax (4A), Cmax (4B), and t1/2 (4C) of Biotropin and SPA-SPA in rat total serum.
Figure 4B:
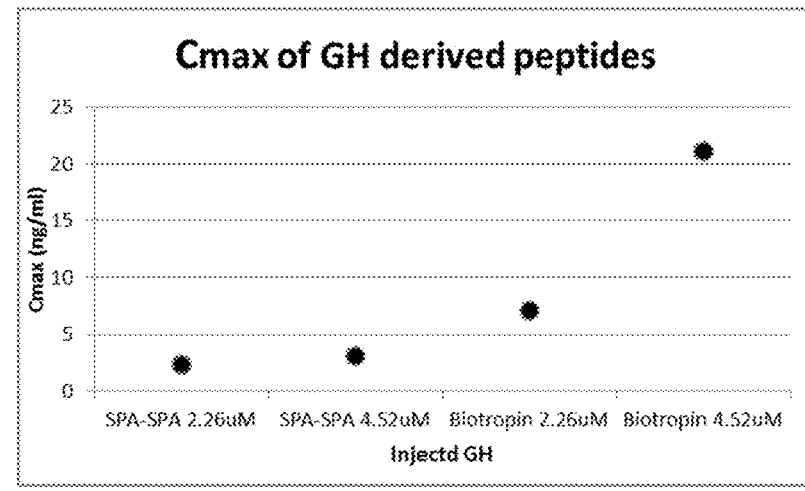
Figure 4C:
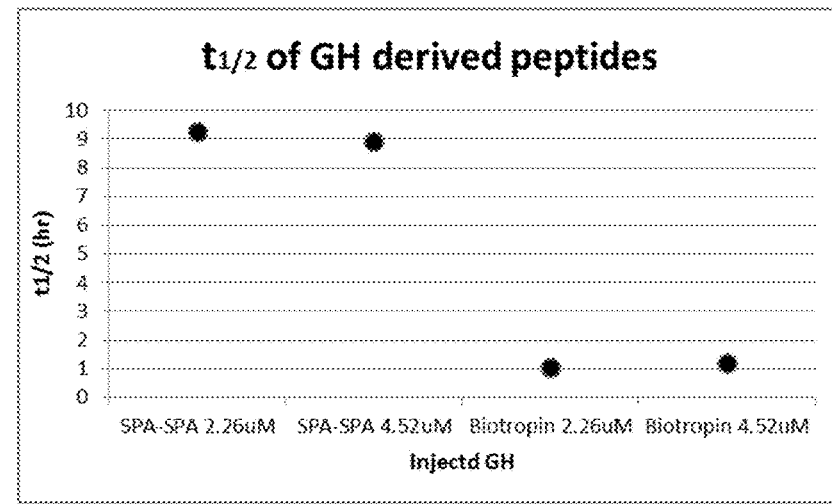

Results show that the t1/2 of the SPA-SPA variant is higher than the commercially available variant of hGH (Bio-tropin) (Table 6, FIG. 4C), meaning that the SPA-SPA peptide presents slower elimination rate and better stability and thus, stays longer in the blood flow. Furthermore, while Biotropin is undetectable 12 hours post injection the SPA-SPA variant is still detectable 48 hr post inj ecti on.

TABLE 6

Pharmacokinetic analysis of hGH variants in rat total serum based on Table 5, conducted by PKSolver analyzer.

| | t1/2 (hr) | Tmax (hr) | Cmax (ng/ml) | Injection dose (ug/kg) |
|---|---|---|---|---|
| SPA-SPA 2.26 uM (74.4 ug/kg) | 9.23 | 4 | 2.39 | 74.4 |
| SPA-SPA 4.52 uM (149 ug/kg) | 8.91 | 4 | 3.08 | 149 |
| Bio-tropin 2.26 uM (50 ug/kg) | 1.04 | 2 | 7.09 | 50 |
| Bio-tropin 4.52 uM (100 ug/kg) | 1.17 | 2 | 21.09 | 100 |

Figure 5A:
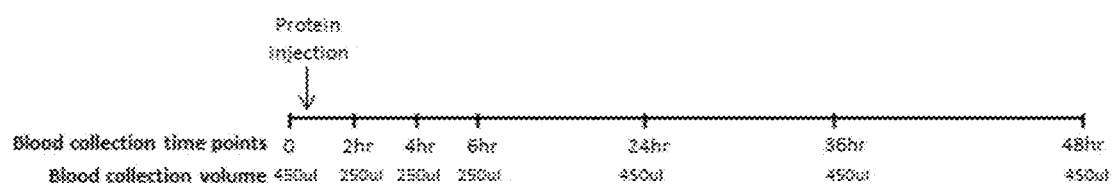
FIG. 5A is a time line illustration of the in vivo assay.

Further, experiments were conducted in order to test a single-SPA variant of hGH (SEQ ID NO: 30). Sprague Dawley rats were injected with Biotropin, SPA and SPA-SPA variants. Saline was used as a negative control. Blood was collected at several time points (0, 2 hr, 4 hr, 6 hr, 24 hr, 36 hr, and 48 hr) and serum was tested in order to detect hGH (FIG. 5A).

Figure 5B:
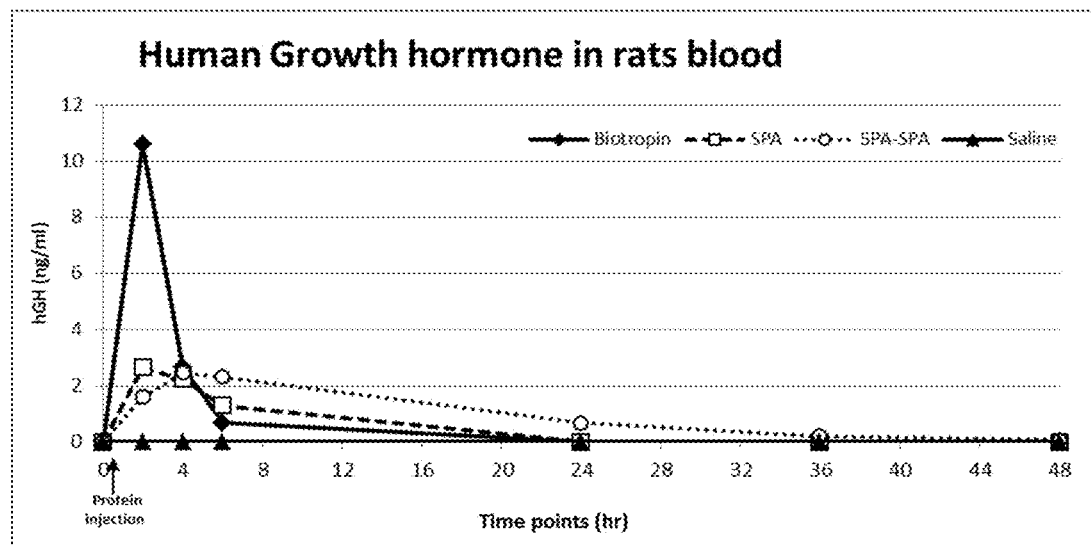
FIG. 5B is a graph illustrating the change in serum concentration of hGH (ng/ml) following subcutaneously injection of Biotropin, SPA, SPA-SPA variant, or saline to rats.
Figure 5C:
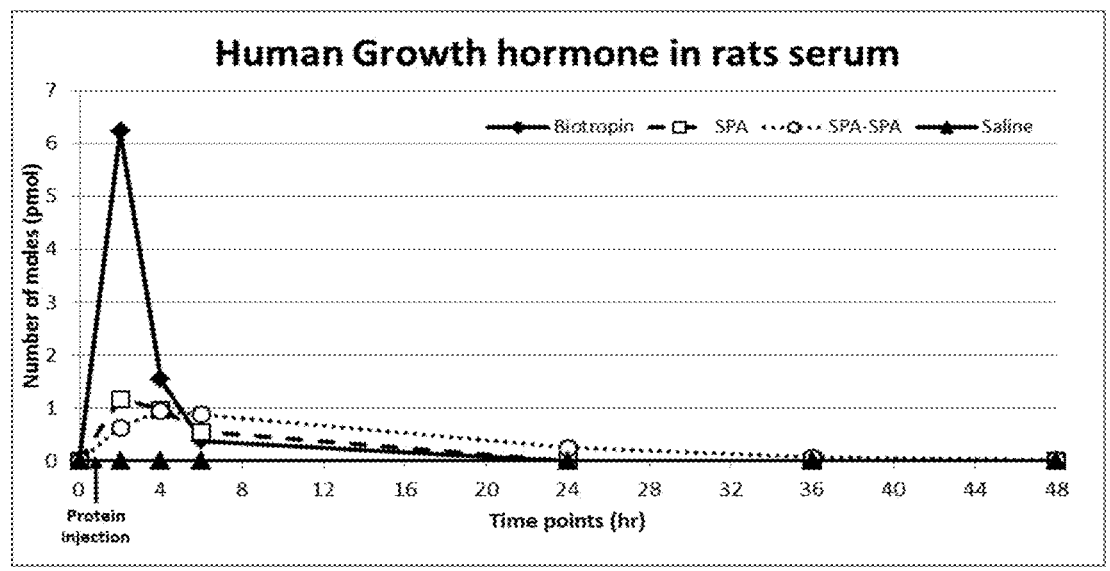
FIG. 5C is a graph showing the change in the number of moles (pmol) of hGH in rats' serum in time dependent manner, following subcutaneously (SC) injection of Biotropin, SPA, SPA-SPA variant, or saline to rats.

Biotropin concentration in the blood demonstrates a fast increase which reaches a peak of ~10.6 ng/ml 2 hours post injection. A sharp decrease of hGH level is presented 4 hours post injection, and hGH levels disappears completely by 24 hours post injection (Tables 7 and 8, and FIG. 5B-C). The SPA variant demonstrates a lower peak of concentration in the blood at 2 hours post injection (2.6 ng/ml), and afterwards the hGH decreases and disappears by 24hr post injection (Tables 7 and 8, and FIG. 5B-C). The SPA-SPA variant shows slow and moderate increase, and reaches a peak of concentration at 6 hours post injection. After that, the level of the SPA-SPA variant decreases slowly and there are still detectable levels of the peptide 48 hours post injection (Tables 7, 8 and FIG. 5B-C).

TABLE 7

Mean result of hGH detected in rat serum (ng/ml)

| Time point (hr) Injected protein (ng/ml) | 0 | 2 | 4 | 6 | 24 | 36 | 48 |
|---|---|---|---|---|---|---|---|
| Biotropin | 0 | 10.61 | 2.67 | 0.69 | 0 | 0 | 0 |
| SPA | 0 | 2.66 | 2.24 | 1.31 | 0 | 0 | 0 |
| SPA-SPA | 0 | 1.59 | 2.46 | 2.31 | 0.68 | 0.21 | 0.07 |
| Saline | 0 | 0 | 0 | 0 | 0 | 0 | 0 |

TABLE 8 hGH in rat total serum (pmol).

| Time point (hr) Injected protein (pmol) | 0 | 2 | 4 | 6 | 24 | 36 | 48 |
|---|---|---|---|---|---|---|---|
| Bio-tropin | 0 | 6.32 | 1.54 | 0.39 | 0 | 0 | 0 |
| SPA | 0 | 1.17 | 0.97 | 0.55 | 0 | 0 | 0 |
| SPA-SPA | 0 | 0.63 | 0.95 | 0.88 | 0.25 | 0.07 | 0.03 |
| Saline | 0 | 0 | 0 | 0 | 0 | 0 | 0 |

Further, the pharmacokinetic parameters of the tested variants were compared to Biotropin. Results demonstrate that the Cmax and Tmax of Biotropin are higher than the chimeric peptides. In contrast, the t1/2 of the SPA-SPA variant is higher than the other peptides, meaning that the SPA-SPA peptide stays longer in the body and presents a slower elimination rate (Table 9).

TABLE 9

Pharmacokinetic analysis of hGH variants and Biotropin in rat total serum based on Table 3.

| | $t_{1/2}$ (hr) | Tmax (hr) | Cmax (ng/ml) |
|---|---|---|---|
| Biotropin | 1.013 | 2 | 10.610 |
| SPA | 3.90 | 2 | 2.66 |
| SPA-SPA | 7.48 | 4 | 2.46 |

Example 4

Determination of EC50 of Three hGH Preparations Using FDC-P1-9D11 Cell Line

Three hGH variants: APE (200 µg/ml) (SEQ ID NO: 33), SPA-SPA (200 µg/ml) (SEQ ID NO: 27) and SPA (200 µg/ml) (SEQ ID NO: 30) were used for bioassay. First each sample was filter-sterilized and then diluted with media to 50 µg/ml. The bioassay was conducted as described in Solomon et al., Growth hormone & IGF Research 16 (2006) 297 to 307, the context of which is incorporated by reference herein.

Figure 6A:
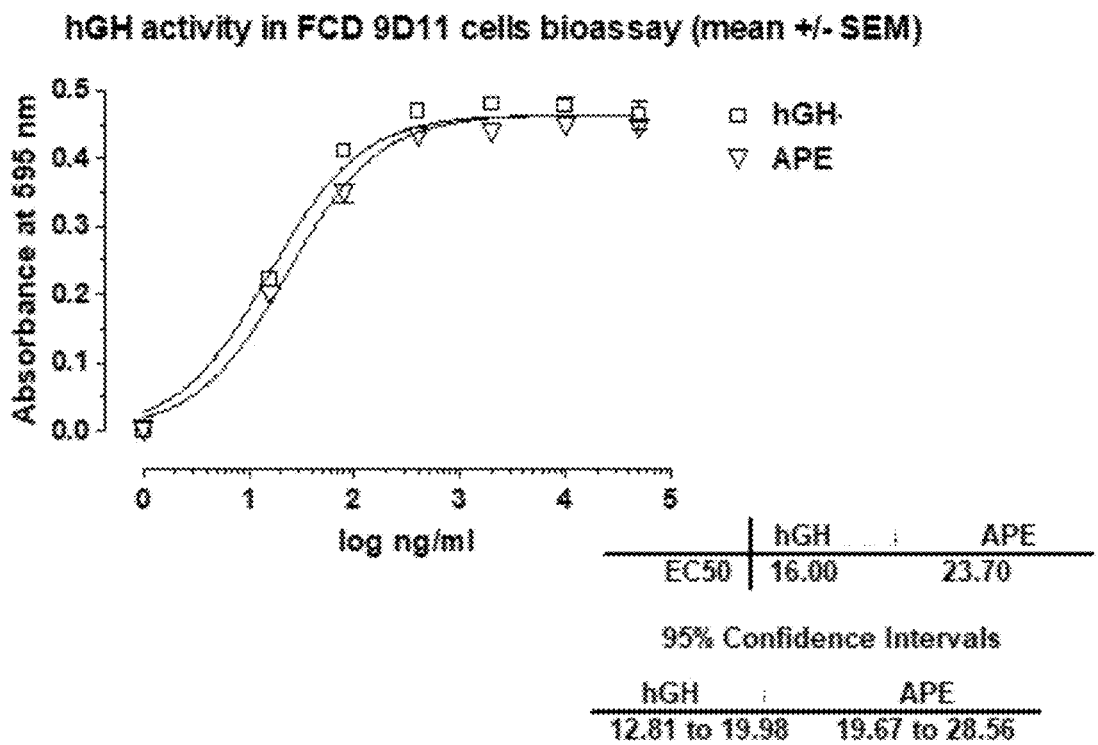
FIGS. 6A-6B are graphs comparing EC50 measurements of commercially available recombinant hGH (hGH) to that of hGH variants APE (6A), SPA and SPA-SPA (6B)

The postulated protein concentration of the 3 supplied samples was 0.2 mg/ml. The bioassay was conducted in triplicates, in two 96 well plates using only the 60 inner wells. hGH which is a commercially available recombinant pituitary human growth hormone (also referred to as hGH (PLR), see www.plr-ltd.com catalog no: GHP-24) was used as a control. Results demonstrate that Protein APE is ~1.5 times less active compared to hGH, but the difference is statistically borderline (FIG. 6A, Table 10).

Figure 6B:
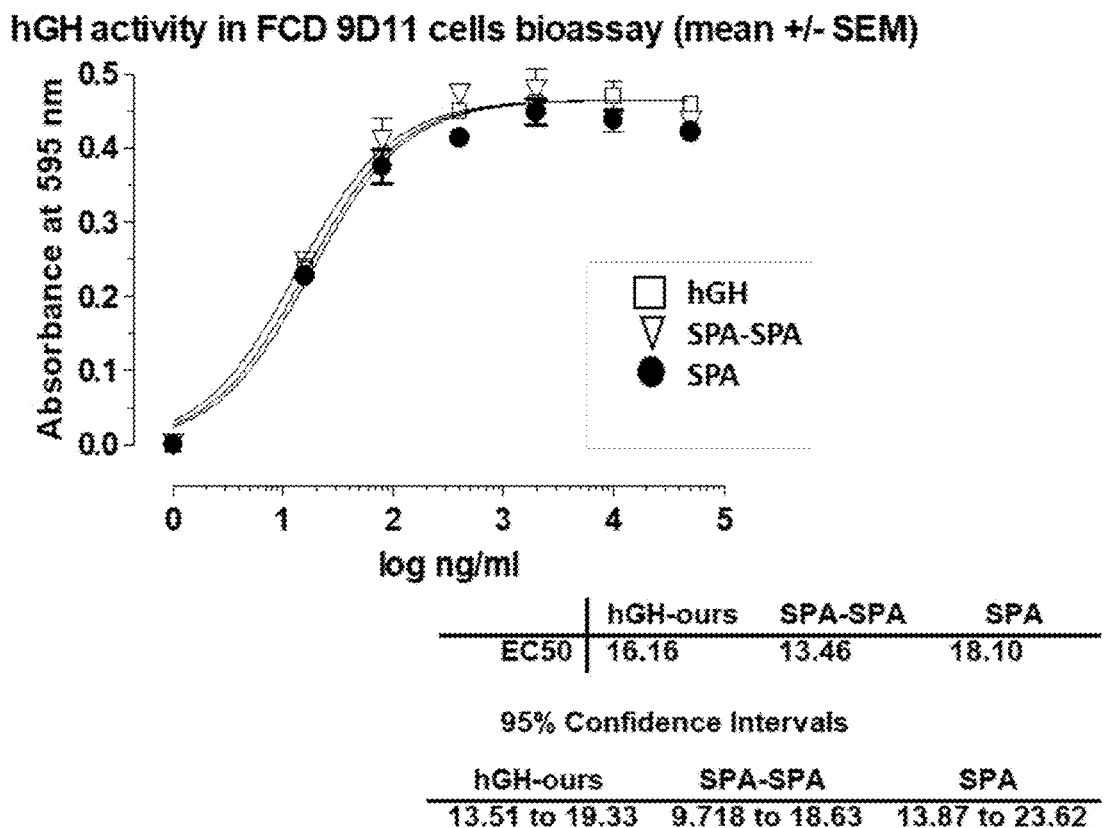

Protein SPA-SPA is ~1.2-fold more active and protein SPA is ~12% less active compared to hGH, but those differences are not statistically significant (FIG. 6B, Table 10). Results are presented in FIGS. 6A and 6B and summarized in Table 10.

TABLE 10

Summary of EC50 bioassay results

| Protein tested | EC50 (ng/ml)* | 95% confidence intervals (ng/ml)* |
|---|---|---|
| Plate 1 | | |
| hGH (PLR) | 16.00 | 12.51 to 19.98 |
| hGH-APE | 23.70 | 19.69 to 28.56 |
| Plate 2 | | |
| hGH (PLR) | 16.16 | 13.33 to 19.33 |
| hGH-SPA-SPA | 13.46 | 9.71 to 18.63 |
| hGH-SPA | 18.10 | 13.87 to 23.62 |

*The concentration is that of the applied protein; 10 µl was added to 100 µl of cell suspension.

The molecular weight (MW) of hGH-SPA-SPA (SEQ ID NO: 27), hGH-SPA (SEQ ID NO: 30), hGH-APE (SEQ ID NO: 33) are different from that of PLR's hGH, (~21.5 kDa). Therefore, activity should be compared not on weight but on a molecular basis. The correction was made by calculating the molarity (M) of each protein using its molecular weight and the EC50 received from the assay, using the following equation:

$$EC50 \text{ by } M = \frac{EC50\left(\frac{ng}{ml}\right) PLR}{Mw(kDa)}$$

For example:
SPA variant: [18.1/29.43]=0.62

The corrected results are presented in Table 11, and indicate that the SPA and SPA-SPA variants are more efficient than the GH reference, as they require fewer molecules in order to reach their EC50 (0.62M, and 0.41M of the variants, respectively, as opposed to 0.74M of the reference). The APE variant presented lower efficacy, as more molecules were needed to reach its EC50 (0.8M).

TABLE 11

Calculated results based on Mw

| Variant | Mw(kDa) | $EC_{50}$ (ng/ml) PLR | $EC_{50}$ by M |
|---|---|---|---|
| SPA | 29.43 | 18.1 | 0.62 |
| APE | 29.65 | 23.7 | 0.80 |
| SPA SPA | 32.92 | 13.46 | 0.41 |
| PLR GH | 21.5 | 16 | 0.74 |

Example 5

Assessing the Effect of Human Growth Hormone (hGH) Variants on Weight Gain in Rats In order to assess the effects of the hGH SPA-SPA variant and Biotropin on weight gain in rats, an in vivo study is conducted. Hypophysectomized Sprague Dawley male rats having a weight of 100 grams (approximately simulating rats at age of 5 weeks, when they are still in their potentially growth phase) are injected subcutaneously (SC) for a duration of 10 days with either: 1) a daily dose of 0.12 mg/kg of Biotropin according to a standard protocol, which amounts to a total dose of 1.2 mg/kg (The molar concentration will be calculated based on this value.); 2) hGH SPA-SPA variant in the same molar concentration as the Biotropin, injected once every 5 days; or 3) Biotropin in the same molar dose, injected once every 5 days.

Blood samples are taken from each rat at day 0, day 1, day 2, day 5, day 8 and day 11 and hGH serum levels are tested as described above. Additionally, rats are weighted at day 0, day 1, day 2, day 5, day 8 and day 11, to follow the growth rate. Optionally the rats are weighed at day 14, 17, 21, 24, 27 and 30 to further follow the growth rate.

EXxample 6

In Vivo Effect of Human Growth Hormone (hGH) Variants on Weight Gain in Rats

Hypophysectomized Sprague Dawley male rats at weight of ~90 grams (simulating rats at an age of ~5 weeks, when they are still in their potentially growth phase) were injected subcutaneously (SC) with Zomacton (commercial GH), or other GH variants: APEmidA (SEQ ID NO: 59), and SPAmid (SEQ ID NO:57), AGAA (SEQ ID NO: 45), at a dosage containing the same number of molecules as the Zomacton 1.8 mg/kg. Rats were treated once every 5 days for 10 days. Weights were measured during the study in order to measure the effect of GH.

In this assay, the tested variants were APEmidA, SPAmid, and AGAA, compared to Zomacton (commercial GH) and to untreated control rats. The rats were observed during several weeks before the assay to make sure that there wasn't any weight gain.

4 groups of hypophysectomized rats (~90gr) were injected once every 5 days with GH variants in the following order:

1) Zomacton injections~total dose of 1.8 mg/kg. (Injection stock of 81.3 uM, 7.3 nmol/90 gr rat).
2) APEmidA injections containing the same molar concentration as the Zomacton injected in group 1.
3) SPAmid injections containing the same molar concentration as the Zomacton injected in group 1.
4) AGAA injections containing the same molar concentration as the Zomacton injected in group 1.

In addition, a group of untreated hypophysectomized rats was used as control. Weight was measured on the day of injection, one and two days post injection and on day 10 (end of study).

Figure 7A:
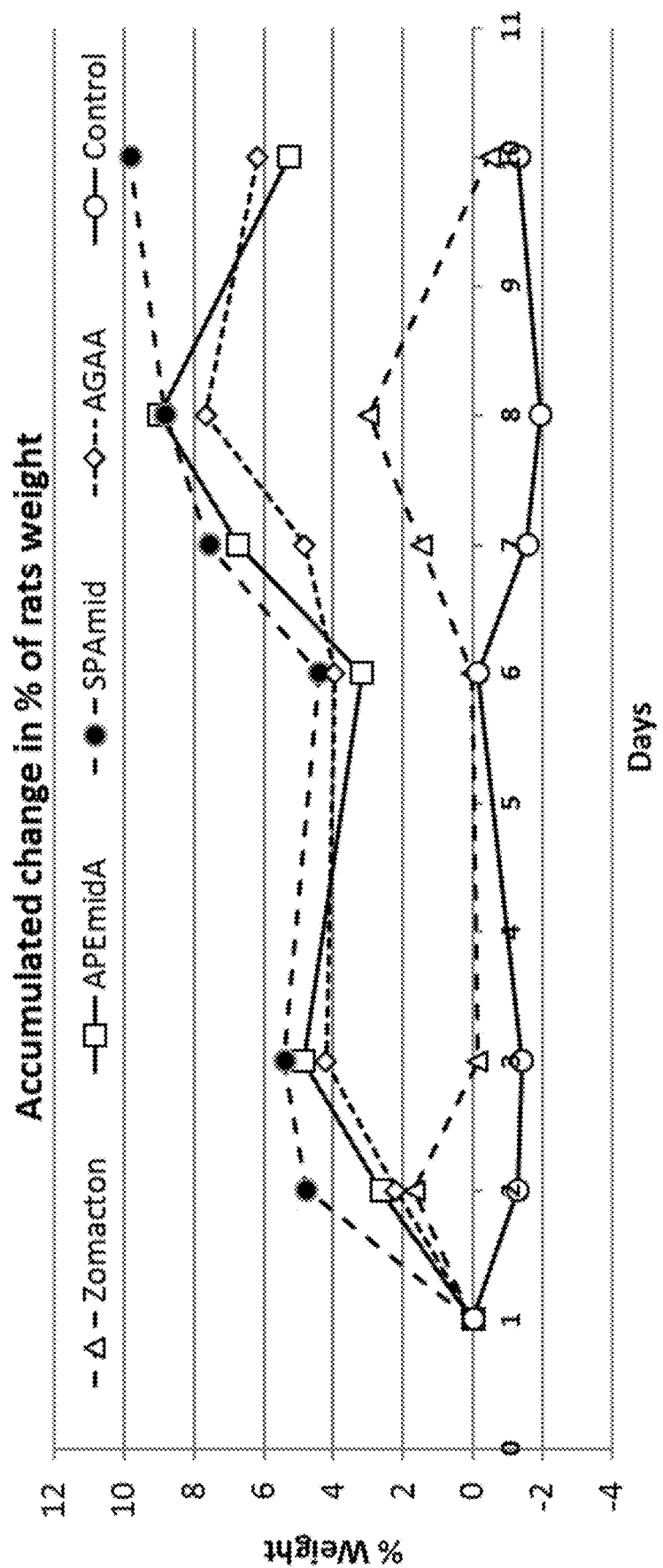
FIGS. 7A-7B are graphs showing accumulated change of rats' weight in % (7A) and grams (7B) during treatment with GH variants, injection days are marked with arrows.
Figure 7B:
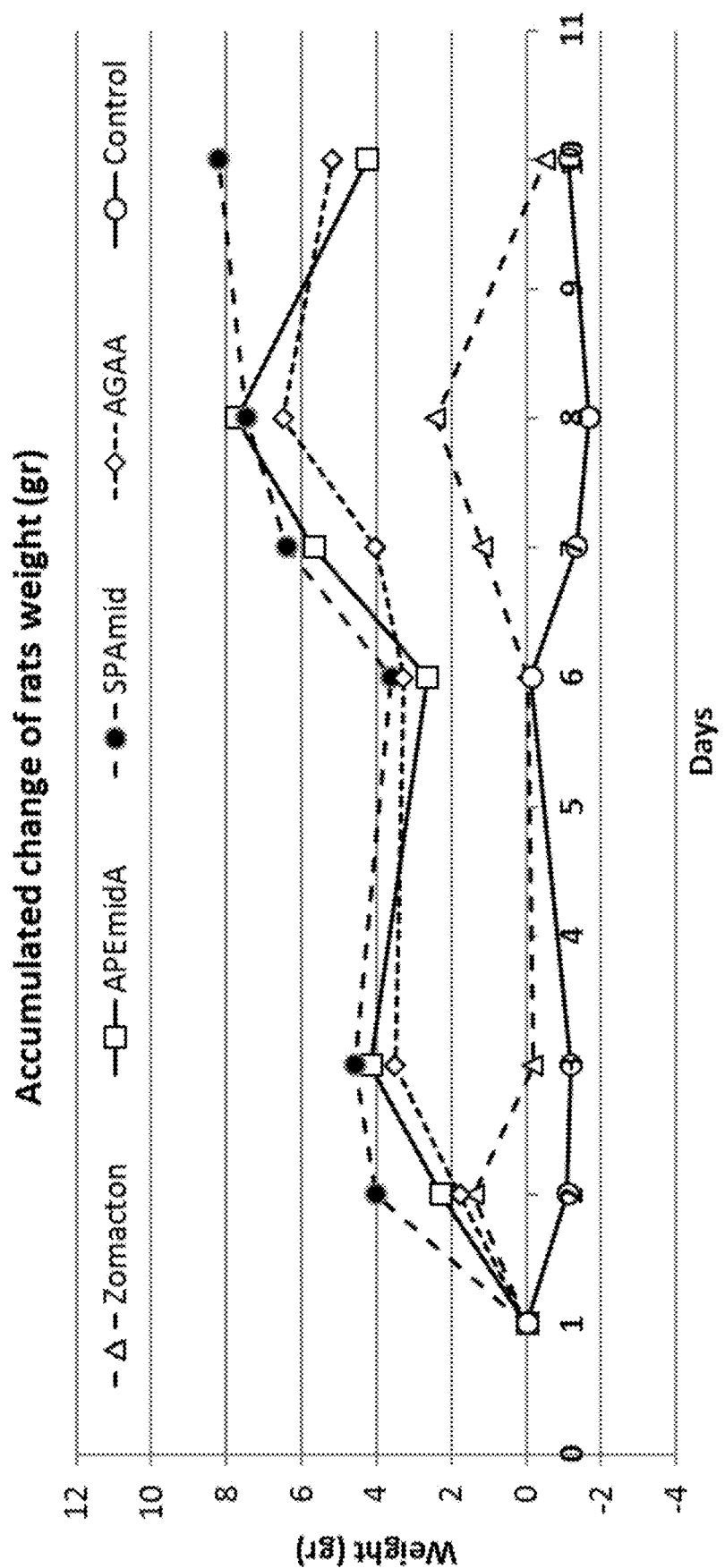

Results demonstrated that the highest weight gain was observed in the SPAmid injected group—9.8% of total weight gained. The APEmidA group gained a total of 5.3%, the AGAA group gained a total of 6.2% (FIG. 7). The control group lost 1.3% of their weight (see control, FIG. 7). The group injected with Zomacton showed weight loss totaling 0.5% (see Zomacton, FIG. 7) This was the first time that the Zomacton group lost weight during this test. One of the rats in the Zomacton group (no.50) showed weight loss in most of the experiment days. It gained weight right after the injection, however it showed a dramatic weight loss (~5%) on the second day after the injection. This could be due to high sensitivity to the Zomacton—a sharp weight gain resulting from the Zomacton administration, and a fast weight loss when the Zomacton stopped its effect. The tested group are composed of only 4 rats each, meaning each rat has a high influence on the average of the group. If this rat is eliminated from the analysis, the total weight change is a gain of 0.7%. It is important to take into consideration that each individual rat may response differently to the injected variant. Thus, this is a possible explaination.

These results correspond with the results of a PLR assay (not shown), that presented SPAmid to be the most effective variant (EC50=~43-59), APEmidA was close with EC50=~45-76. AGAA had a high range result of EC50=~617-1775.

Notably, when focusing on the SPAmid group, there seems to be two main groups of weight gain: one group that gained ~6% of their weight and second group with a gain of ~14% (see Table 12). Interestingly the group that gained the highest percentage contained rats with lower starting weight (79.7ge compared to 89.4 gr). This result contradicts the hypothesis that rats with higher starting weight would gain more weight as compared to rats with lower starting weight. The other two rats in this group presented relatively close weights (81.3 gr and 81.0 gr), one of them gained ~6%, and the other gained ~14%.

2) 1.2 mg/kg SPAmid injection—containing the same molar concentration as the 0.9 mg/kg Zomacton (Injection stock of 40.7 uM, 3.66 nmol/90 gr rat).

3) 2.4 mg/kg SPAmid injection—containing the same molar concentration as the 1.8 mg/kg Zomacton (Injection stock of 81.3 uM, 7.3 nmol/90 gr rat).

Weight was measured on the day of injection, one and two days post injection and on day 10 (end of study).

Figure 8A:
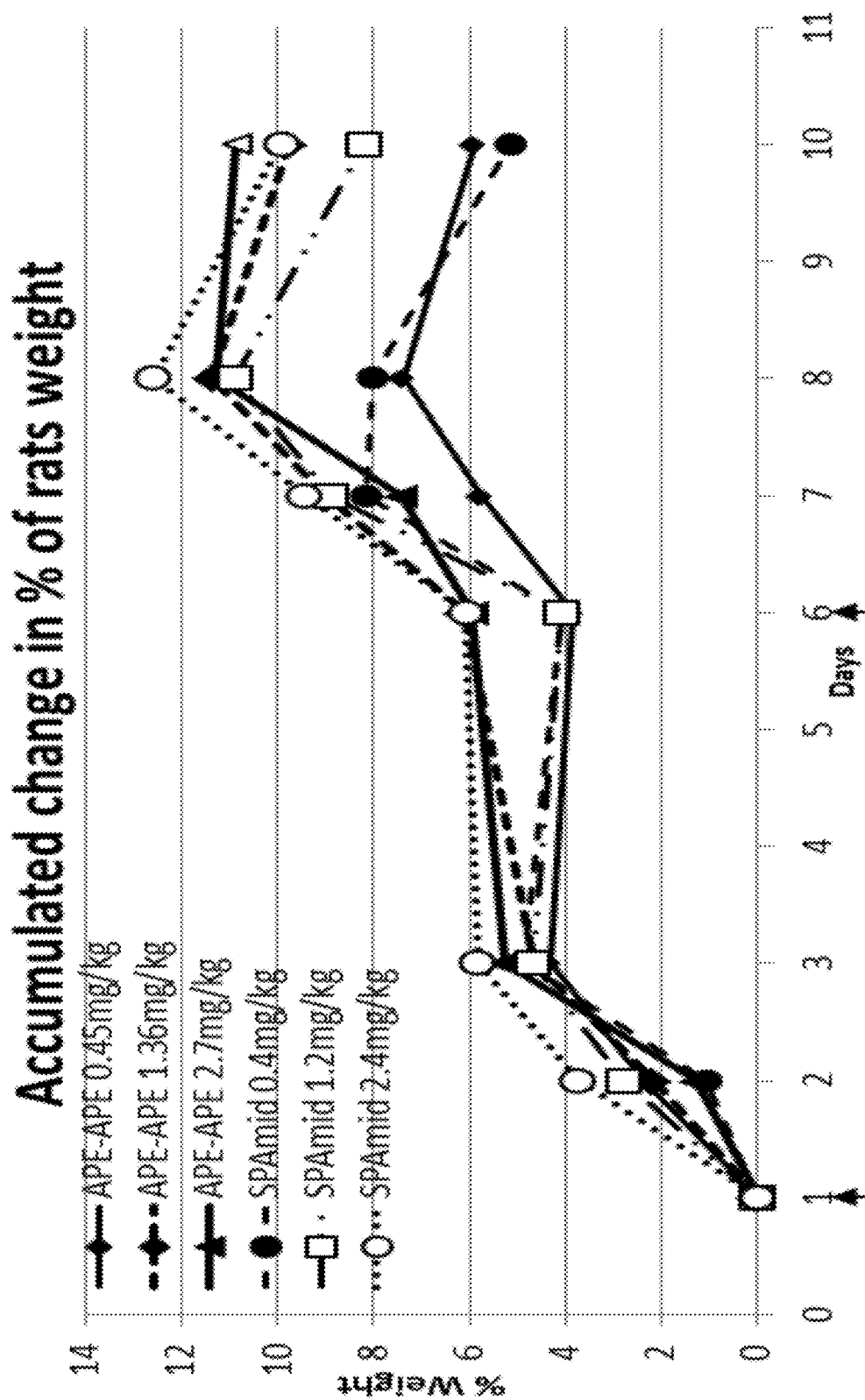
FIGS. 8A-8B are graphs showing accumulated change of rats' weight in % (8A) and grams (8B) during treatment with different doses of GH variants APE-APE and SPAmid, injection days are marked with arrows.
Figure 8B:
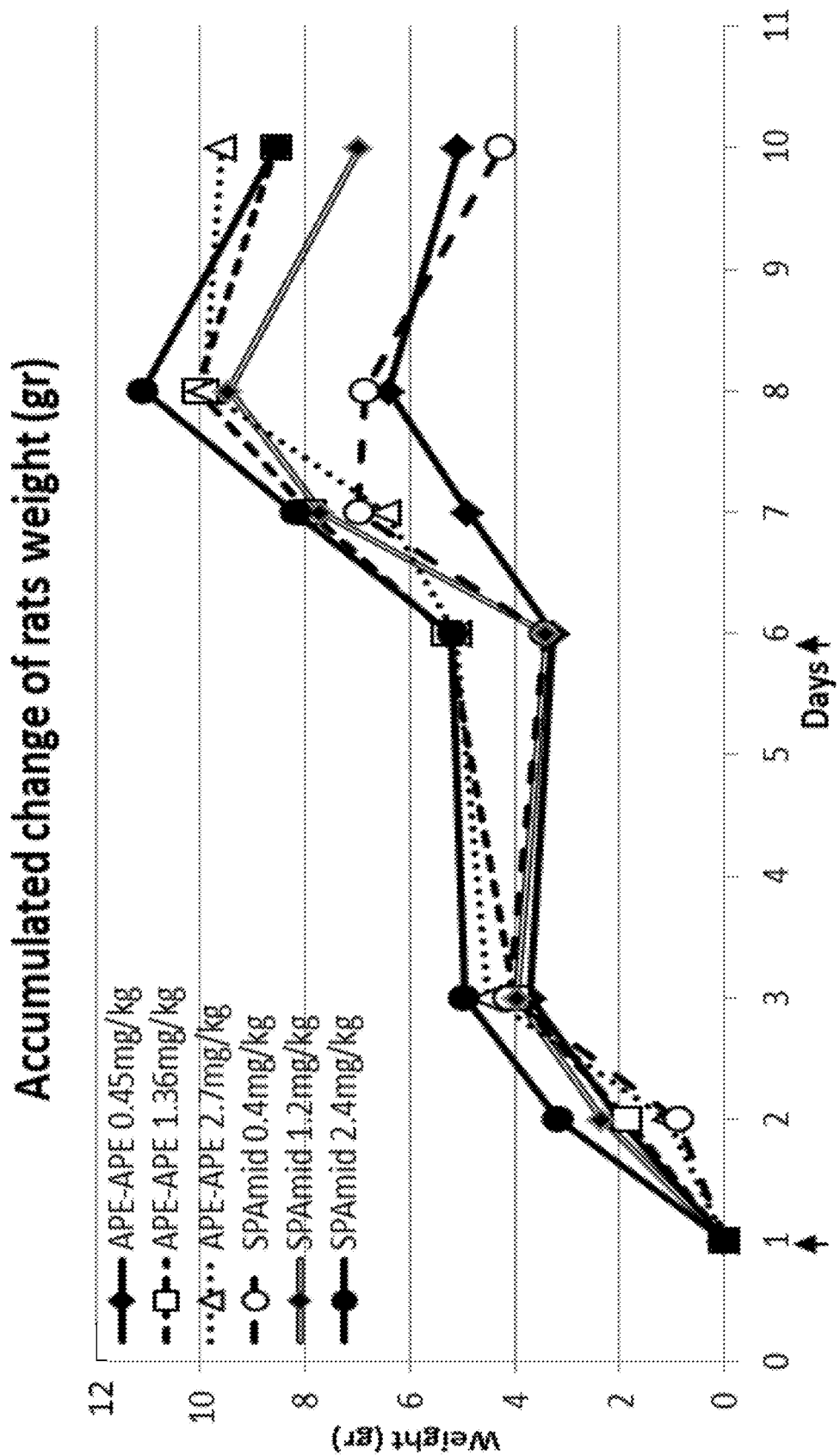

The results (FIG. 8A-B) indicate that the APE-APE variant caused higher weight gain then the SPAmid, in all the tested groups. Specifically, the highest average weight gain was observed while the rats received the highest dosage of the GH (at a molecular number equivalent to 1.8 mg/kg of Zomacton)—the APE-APE variant demonstrated gain of 10.8%, while SPAmid caused 9.9% weight gain. The second dosage (molecular number equivalent to 0.9 mg/kg of Zomacton) caused 9.8% weight gain when APE-APE was injected and 8.2% when SPAmid was used. The lowest dosage (containing molecular number equivalent to 0.3 mg/kg of Zomacton) caused a gain of 5.9% in the APE-APE group and 5.2% in the SPAmid group.

It should be noted that, in the groups equivalent to 0.9 mg/kg and 1.8 mg/kg of the APE-APE variant there are usually two rats presenting higher weigh gain and one rat presenting a lower one. While in the SPAmid groups there are two rats with lower weight gain and one with a relatively higher one. Thus, it is a possible hypothesis that the APE-APE groups could gain more weight than the average shows, while the SPAmid groups could gain less weight. As there

TABLE 12

Weight follow up of hypophysectomized rats injected with SPAmid variant once every 5 days.

| Rat Number | Days | | | | | | | Sum of Weight |
|---|---|---|---|---|---|---|---|---|
| | 1<br>1$^{st}$ injection | 2 | 3 | 6<br>2$^{nd}$ injection | 7 | 8 | 10 | (%) change following 10 days |
| 11 | 81.3 | 84.5 | 84.8 | 85.1 | 86.5 | 88.5 | 86.1 | 5.9 |
| 44 | 89.4 | 96.1 | 96.8 | 93.3 | 98.5 | 98.2 | 94.2 | 5.8 |
| 53 | 81 | 83.4 | 83.7 | 81.7 | 84.8 | 86.5 | 92.7 | 13.9 |
| 65 | 79.7 | 83.5 | 84.4 | 85.8 | 87.2 | 88.1 | 91.3 | 13.8 |

Further experiments were conducted to estimate the optimal dose of each of APE-APE (SEQ ID NO: 42) and SPAmid (SEQ ID NO: 57). Hypophysectomized Sprague Dawley male rats at weight of ~90 gr were divided into 3 groups, each group was injected subcutaneously (SC) once every 5 days with APE-APE or SPAmid variants at doses containing the same number of molecules as the commercial GH (Zomacton) at 0.3 mg/kg, 0.9 mg/kg and 1.8 mg/kg. The rats were divided and injected in the following order:

1) 0.45 mg/kg APE-APE injection—containing the same molar concentration as the 0.3mg/kg Zomacton (Injection stock of 13.5 uM, 1.22 nmol/90 gr rat).

2) 1.36 mg/kg APE-APE injection—containing the same molar concentration as the 0.9mg/kg Zomacton (Injection stock of 40.7 uM, 3.66 nmol/90 gr rat).

3) 2.7 mg/kg APE-APE injection—containing the same molar concentration as the 1.8 mg/kg Zomacton (Injection stock of 81.3 uM, 7.3 nmol/90 gr rat).

1) 0.4 mg/kg SPAmid injection—containing the same molar concentration as the 0.3 mg/kg Zomacton (Injection stock of 13.5 uM, 1.22 nmol/90 gr rat).

were only 3 rats in each group that hypothesis can't be relied on and more studies need to be done.

Example 7

GH Effect on Hypophysectomized Rats

Hypophysectomized Sprague Dawley male rats at weight of ~82 gr (simulating rats at age of ~5 weeks, when they are still in their potentially growth phase) were injected subcutaneously (SC) with Zomacton (commercial GH) and also with another GH variant—SPAmid. Total dosage of SPAmid was 5 mg/kg, 10 mg/kg and 15 mg/kg. Total dosage of Zomacton was at similar molar ratio as the SPAmid 5 mg/kg (i.e. 3.76 mg/kg) and 15 mg/kg (i.e. 11.28 mg/kg). Zomacton, 3.76 mg/kg group was administrated once a day for 9 days. While the Zomacton 11.28 mg/kg group and SPAmid groups were administrated once every 5 days. Weight of the mice was measured during the study in order to measure the effect of GH.

Figure 9A:
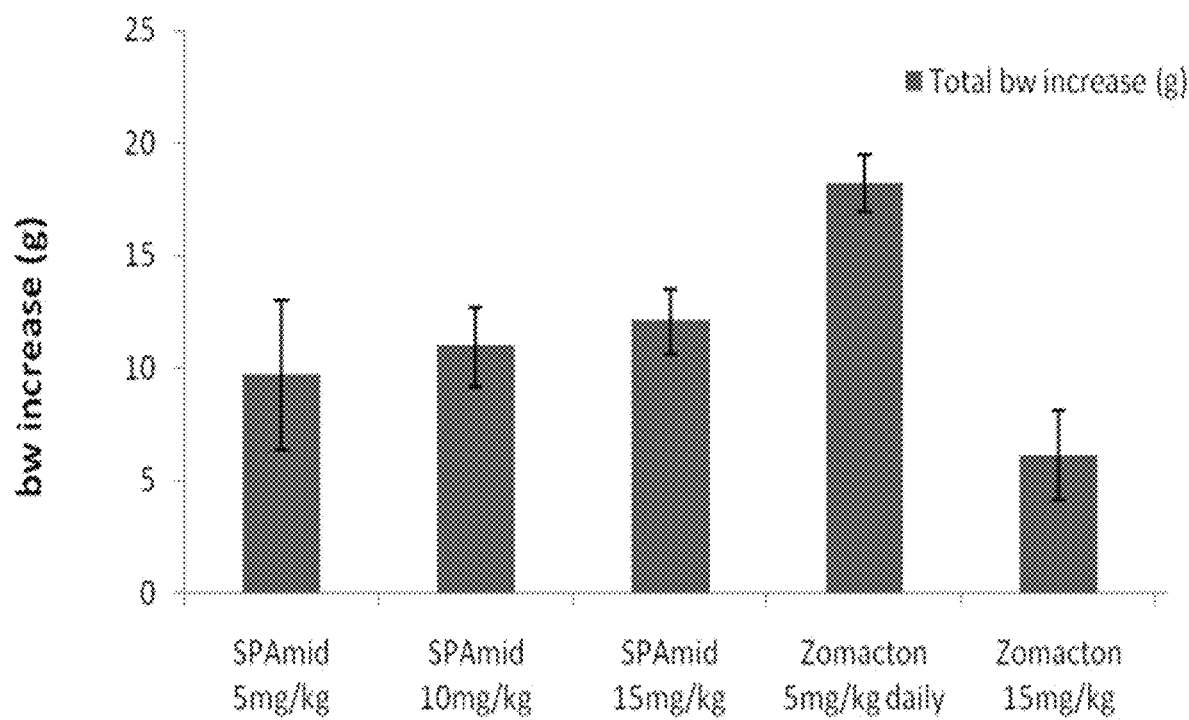
FIGS. 9A-9B are graphs illustrating the increase in body weight (g) (9A) and grams (9B) of SPAmid and Zomacton treated group of rats.
Figure 9B:
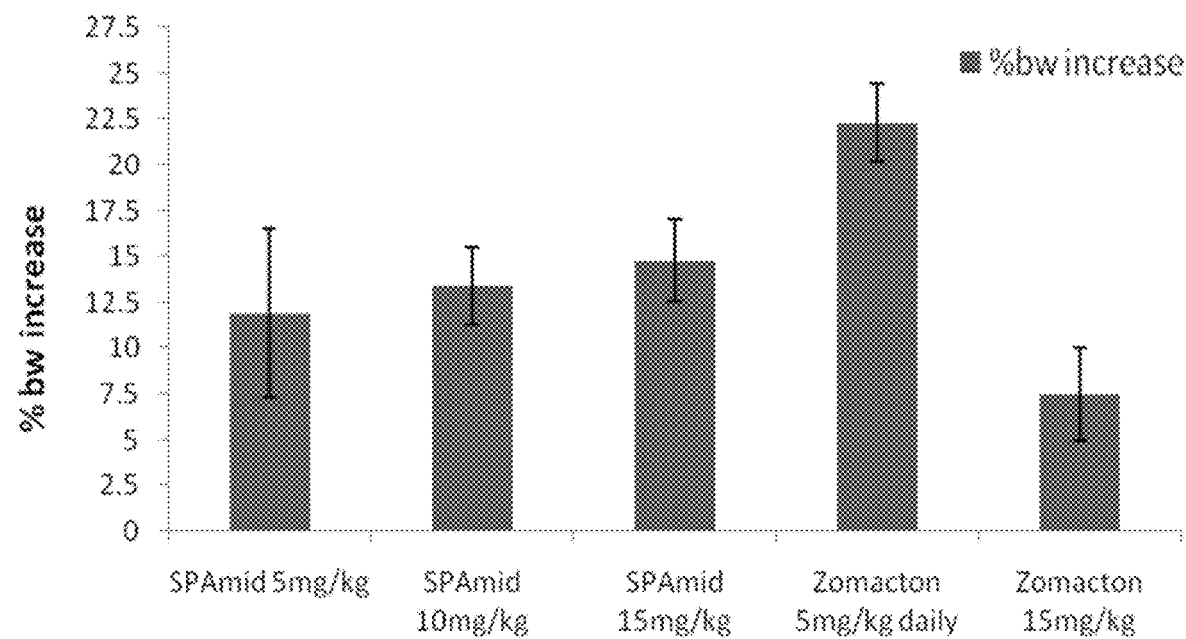

In the SPAmid (5 mg/kg) group, body weight increase of 11.9% was seen, in the SPAmid (10 mg/kg) group, body weight increase of 13.4% was seen, and in the SPAmid (15 mg/kg) group, body weight increase of 14.8% was seen. This indicated that there is a positive correlation between increasing doses of SPAmid and body weight increase (FIG. 9A-B).

In contrast, in the Zomacton 3.76 mg/kg (equivalent to 5 mg/kg SPAmid) group, injections were given daily for 9 days in all) day experimental period, and resulted in a body weight increase of 22.3%, and in the Zomacton 11.28 mg/kg (equivalent to 15 mg/kg SPAmid) group, injections were given once every 5 days, i.e. twice in a 10 days experimental period, and resulted in a body weight increase of 7.5%.

This indicated that Zomacton 11.28 mg/kg (equivalent to 15 mg/kg SPAmid) group showed a body weight increase that was half as good as the increase caused in the equivalent SPAmid treated group (7.5% vs. 14.8). Further, it appears that daily dosage has a stronger effect than giving the GH once in 5 days.

Example 8

Assessing the Endurance of Cytokine Variants in the Blood of Mice

Some cytokines which have therapeutic potential are also sometimes harmful and elicit an adverse immune response when administered to a subject. Due to this risk, cytokines such as IL-2 and others have shown poor clinical results. However, at law dosage some cytokines may provide a therapeutic effect without eliciting an adverse response. Cytokine variants of the present invention which exhibit prolonged endurance in the blood may provide an improved therapeutic effect when administered at low dose.

To assess the pharmacokinetic profile of cytokine chimeras of the present invention, three IL-2 variants were compared to Peprotech recombinant human IL2 (rhIL2 Mw=15.51kDa). The variants were named "S2S" (Mw=26.5 kDa, SEQ ID NO:69), "S2A" (Mw=26 kDa, SEQ ID NO:65) and "A2A" (SEQ ID NO:67). Due to a mass ratio=~0.58—Each molecule of the variants is approximately equivalent to ~1.72 molecules of rhIL2.

Figure 10:
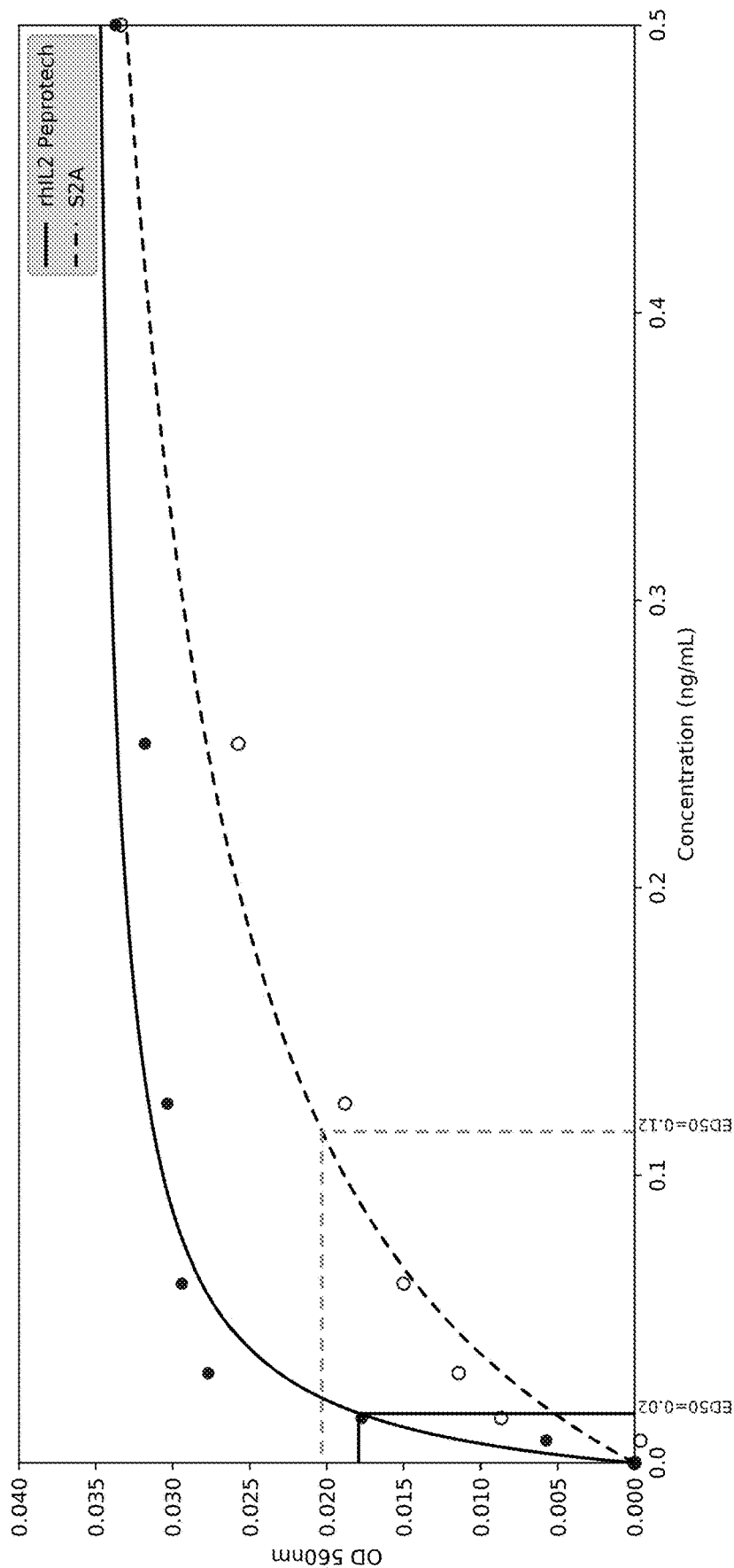
FIG. 10 is a logistic regression curve (Michaelis-Menten model), and ED50 calculation of MTT results assay.

In vitro assay: In order to establish the effect of S2A in culture and to assess the Mass to International Units (IU) ratio, a viability test was performed using MTT on a CTLL-2 derived cell line (CTLD) (FIG. 10A-B). Data was fitted to a curve (Michaelis-Menten model, FIG. 10A), and ED50 was extrapolated (FIG. 10B). ED50 for Pep is 0.017, and ED50 for S2A is 0.115. With a mass ratio of 6.7, the adjusted for mass ratio ED50 is 6.7×0.58=3.9.

Specific Activity is defined as $$SA = \frac{1 \times 10^6}{ED_{50}\left(\frac{ng}{mL}\right)} t$$

therefore:

$$SA_{Pep} = \frac{1 \times 10^6}{0.017\left(\frac{ng}{mL}\right)} = 58,823,529.41 \frac{IU}{mg}$$

which is approximately 5.8 times the proclaimed amount of the manufacturer (ED50=0.66, SA=1×10^7).

$$SA_{S2A} = \frac{1 \times 10^6}{0.115\left(\frac{ng}{mL}\right)} = 8,695,652.17 \frac{IU}{mg}$$

keeping the 6.7 ratio to the Peprotech.

Figure 11:
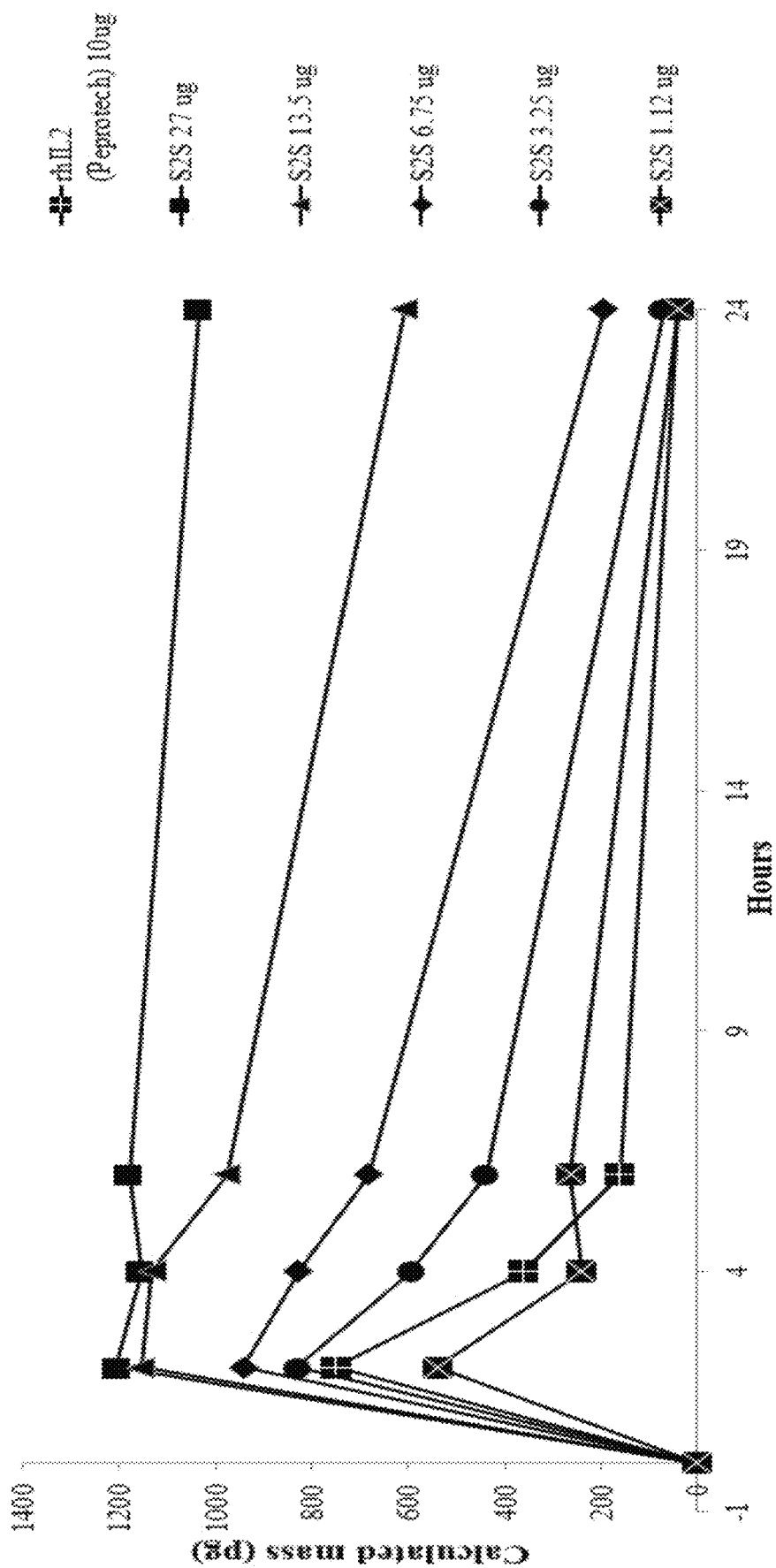
FIG. 11 is a graph illustrating the calculated serum cytokine levels of S2S from injections at different concentrations as compared to rhIL2.

In vivo assay: To assess the endurance of cytokines in the blood, mice were injected (SC) with cytokines in different doses, and blood was taken at set intervals. Serum was separated and cytokine levels were calculated using ELISA. Mass was calculated according to the slope of linear regression of the linear phase of a calibration curve. Curves show S2S has better endurance in blood and/or slower release rate. Even when taking in consideration mass ratio compensation (10 ug dose of rhIL2 is equivalent to 17.24 ug of S2S), levels of S2S are higher and more enduring, suggesting a vast difference in pharmacokinetics and pharmacodynamics (FIG. 11).

Figure 12A:
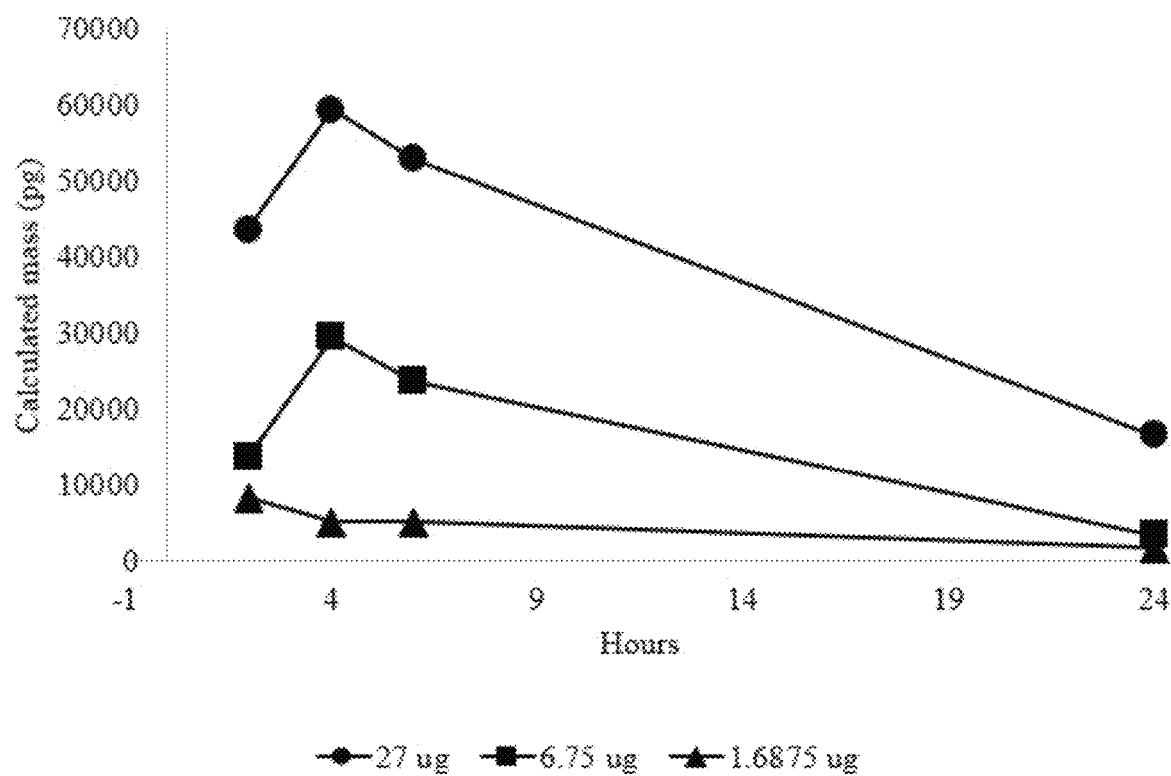
FIGS. 12A-12B are graphs illustrating the calculated serum cytokine levels of S2A (12A) and A2A (12B) from injections at different concentrations.
Figure 12B:
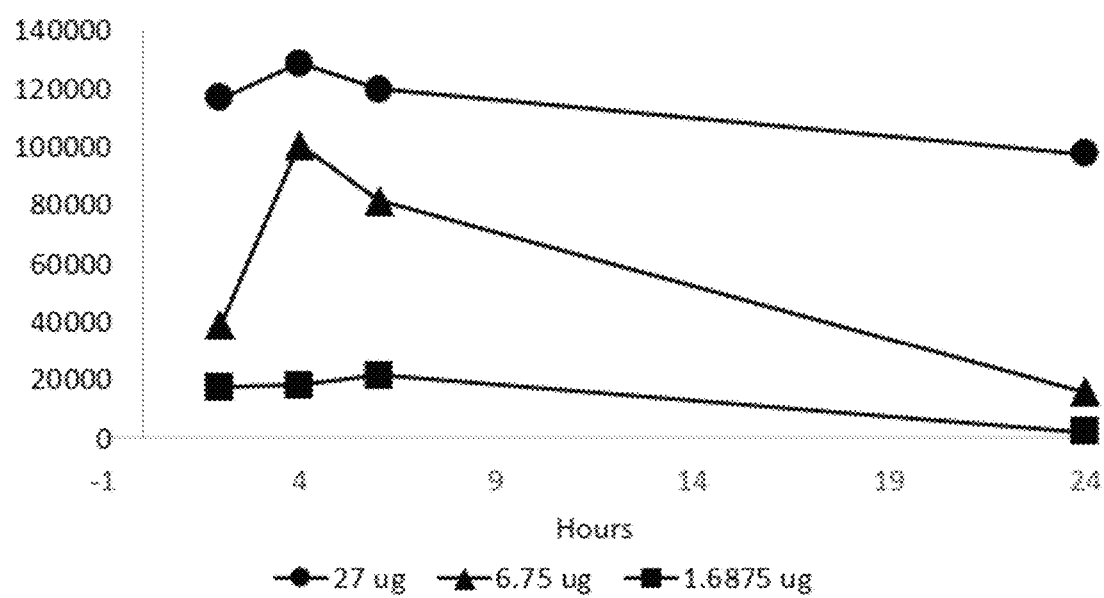

Similar experiments were performed for S2A (FIG. 12A) and A2A (FIG. 12B). Mass was calculated according to the slope of linear regression of the linear phase of a calibration curve. Notably, the S2A and A2A variants exhibited a similar pattern to that of S2S, both in plasma level and endurance.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A chimera consisting of a peptide consisting of 20 to 50 contiguous amino acid residues from amino acids 130 to 199 of SEQ ID NO: 1, fused directly to a protein of interest and wherein a leader peptide is optionally present at the N-terminus of the chimera.

2. The chimera of claim 1, wherein the protein of interest is a cytokine or a hormone.

3. The chimera of claim 1, wherein the peptide is fused to the amino terminus of said protein of interest.

4. A pharmaceutical composition comprising the chimera of claim 1, and a pharmaceutically acceptable carrier.

5. A method of extending the biological half-life of a protein of interest, comprising the step of providing a chimera by fusing a peptide consisting of 20 to 50 contiguous amino acid residues from amino acids 130 to 199 of SEQ ID NO: 1 directly to a protein of interest, thereby extending the biological half-life of a protein of interest.

6. The chimera of claim 1, wherein the peptide is fused to the carboxy terminus of said protein of interest.

7. A chimera consisting of a peptide selected from the group consisting of SEQ ID NOs: 2, 3, 4, and 5 fused directly to a protein of interest, wherein a leader peptide is optionally present at the N-terminus of the chimera.

8. The chimera of claim 7, wherein SEQ ID NO: 2 is fused directly to said protein of interest.

9. The chimera of claim 7, wherein the peptide is fused to the amino terminus of said protein of interest.

10. A pharmaceutical composition comprising the chimera of claim 7, and a pharmaceutically acceptable carrier.

11. The chimera of claim 7, wherein SEQ ID NO: 3 is fused directly to said protein of interest.

12. The chimera of claim 7, wherein SEQ ID NO: 4 is fused directly to said protein of interest.

13. The chimera of claim 7, wherein SEQ ID NO: 5 is fused directly to said protein of interest.

14. The chimera of claim 7, wherein the protein of interest is a cytokine or a hormone.

15. A method of extending the biological half-life of a protein of interest, comprising the step of providing a chimera by fusing a peptide selected from the group consisting of SEQ ID NOs: 2, 3, 4, and 5 directly to a protein of interest, thereby extending the biological half-life of a protein of interest.

16. The chimera of claim 7, wherein the peptide is fused to the carboxy terminus of said protein of interest.

* * * * *

SEQUENCE LISTING

```
<160> NUMBER OF SEQ ID NOS: 71

<210> SEQ ID NO 1
<211> LENGTH: 270
<212> TYPE: PRT
<213> ORGANISM: Homo sapiens
<220> FEATURE:
<221> NAME/KEY: LAcetylated
<222> LOCATION: (269)..(269)

<400> SEQUENCE: 1

Met Ala Trp Arg Ala Leu His Pro Leu Leu Leu Leu Leu Leu Leu Phe
1               5                   10                  15

Pro Gly Ser Gln Ala Gln Ser Lys Ala Gln Val Leu Gln Ser Val Ala
```

```
            20                  25                  30
Gly Gln Thr Leu Thr Val Arg Cys Gln Tyr Pro Pro Thr Gly Ser Leu
        35                  40                  45
Tyr Glu Lys Lys Gly Trp Cys Lys Glu Ala Ser Ala Leu Val Cys Ile
    50                  55                  60
Arg Leu Val Thr Ser Ser Lys Pro Arg Thr Met Ala Trp Thr Ser Arg
65                  70                  75                  80
Phe Thr Ile Trp Asp Asp Pro Asp Ala Gly Phe Phe Thr Val Thr Met
                85                  90                  95
Thr Asp Leu Arg Glu Glu Asp Ser Gly His Tyr Trp Cys Arg Ile Tyr
            100                 105                 110
Arg Pro Ser Asp Asn Ser Val Ser Lys Ser Val Arg Phe Tyr Leu Val
        115                 120                 125
Val Ser Pro Ala Ser Ala Ser Thr Gln Thr Ser Trp Thr Pro Arg Asp
    130                 135                 140
Leu Val Ser Ser Gln Thr Gln Thr Gln Ser Cys Val Pro Pro Thr Ala
145                 150                 155                 160
Gly Ala Arg Gln Ala Pro Glu Ser Pro Ser Thr Ile Pro Val Pro Ser
                165                 170                 175
His Pro Ser Ser Pro Leu Pro Val Pro Leu Pro Ser Arg Pro Gln Asn
            180                 185                 190
Ser Thr Leu Arg Pro Gly Pro Ala Ala Pro Ile Ala Leu Val Pro Val
        195                 200                 205
Phe Cys Gly Leu Leu Val Ala Lys Ser Leu Val Leu Ser Ala Leu Leu
    210                 215                 220
Val Trp Trp Val Leu Arg Asn Arg His Met Gln His Gln Gly Arg Ser
225                 230                 235                 240
Leu Leu His Pro Ala Gln Pro Arg Pro Gln Ala His Arg His Phe Pro
                245                 250                 255
Leu Ser His Arg Ala Pro Gly Gly Thr Tyr Gly Gly Lys Pro
            260                 265                 270

<210> SEQ ID NO 2
<211> LENGTH: 70
<212> TYPE: PRT
<213> ORGANISM: Homo sapiens

<400> SEQUENCE: 2

Ser Pro Ala Ser Ala Ser Thr Gln Thr Ser Trp Thr Pro Arg Asp Leu
1               5                   10                  15
Val Ser Ser Gln Thr Gln Thr Gln Ser Cys Val Pro Pro Thr Ala Gly
            20                  25                  30
Ala Arg Gln Ala Pro Glu Ser Pro Ser Thr Ile Pro Val Pro Ser His
        35                  40                  45
Pro Ser Ser Pro Leu Pro Val Pro Leu Pro Ser Arg Pro Gln Asn Ser
    50                  55                  60
Thr Leu Arg Pro Gly Pro
65                  70

<210> SEQ ID NO 3
<211> LENGTH: 34
<212> TYPE: PRT
<213> ORGANISM: Homo sapiens

<400> SEQUENCE: 3

Ser Pro Ala Ser Ala Ser Thr Gln Thr Ser Trp Thr Pro Arg Asp Leu
```

```
                1               5                  10                 15
Val Ser Ser Gln Thr Gln Thr Gln Ser Cys Val Pro Pro Thr Ala Gly
            20                  25                 30

Ala Arg

<210> SEQ ID NO 4
<211> LENGTH: 36
<212> TYPE: PRT
<213> ORGANISM: Homo sapiens

<400> SEQUENCE: 4

Gln Ala Pro Glu Ser Pro Ser Thr Ile Pro Val Pro Ser His Pro Ser
1               5                  10                 15

Ser Pro Leu Pro Val Pro Leu Pro Ser Arg Pro Gln Asn Ser Thr Leu
            20                  25                 30

Arg Pro Gly Pro
            35

<210> SEQ ID NO 5
<211> LENGTH: 70
<212> TYPE: PRT
<213> ORGANISM: Homo sapiens

<400> SEQUENCE: 5

Ser Pro Ala Ser Ala Ser Thr Gln Thr Ser Trp Thr Pro Arg Asp Leu
1               5                  10                 15

Val Ser Ser Gln Thr Gln Thr Gln Ser Cys Val Pro Pro Thr Ala Gly
            20                  25                 30

Ala Arg Gln Ala Pro Glu Ser Pro Ser Thr Ile Pro Val Pro Ser His
            35                  40                 45

Pro Ser Ser Pro Leu Pro Val Pro Leu Pro Ser Arg Pro Gln Ala Ser
         50                  55                 60

Thr Leu Arg Pro Gly Pro
65                  70

<210> SEQ ID NO 6
<211> LENGTH: 8
<212> TYPE: PRT
<213> ORGANISM: Artificial
<220> FEATURE:
<223> OTHER INFORMATION: Synthetic

<400> SEQUENCE: 6

Trp Ser His Pro Gln Phe Glu Lys
1               5

<210> SEQ ID NO 7
<211> LENGTH: 8
<212> TYPE: PRT
<213> ORGANISM: Artificial
<220> FEATURE:
<223> OTHER INFORMATION: Synthetic

<400> SEQUENCE: 7

His His His His His His His His
1               5

<210> SEQ ID NO 8
<211> LENGTH: 24
<212> TYPE: PRT
<213> ORGANISM: Homo sapiens
```

<400> SEQUENCE: 8

Met Glu Met Phe Gln Gly Leu Leu Leu Leu Leu Leu Ser Met Gly
1               5                   10                  15

Gly Thr Trp Ala Ser Lys Glu Pro
            20

<210> SEQ ID NO 9
<211> LENGTH: 165
<212> TYPE: PRT
<213> ORGANISM: Homo sapiens

<400> SEQUENCE: 9

Met Glu Met Phe Gln Gly Leu Leu Leu Leu Leu Leu Ser Met Gly
1               5                   10                  15

Gly Thr Trp Ala Ser Lys Glu Pro Leu Arg Pro Arg Cys Arg Pro Ile
            20                  25                  30

Asn Ala Thr Leu Ala Val Glu Lys Glu Gly Cys Pro Val Cys Ile Thr
        35                  40                  45

Val Asn Thr Thr Ile Cys Ala Gly Tyr Cys Pro Thr Met Thr Arg Val
    50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
            100                 105                 110

Cys Arg Arg Ser Thr Thr Asp Cys Gly Gly Pro Lys Asp His Pro Leu
        115                 120                 125

Thr Cys Asp Asp Pro Arg Phe Gln Asp Ser Ser Ser Ser Lys Ala Pro
    130                 135                 140

Pro Pro Ser Leu Pro Ser Pro Ser Arg Leu Pro Gly Pro Ser Asp Thr
145                 150                 155                 160

Pro Ile Leu Pro Gln
                165

<210> SEQ ID NO 10
<211> LENGTH: 173
<212> TYPE: PRT
<213> ORGANISM: Artificial
<220> FEATURE:
<223> OTHER INFORMATION: Synthetic

<400> SEQUENCE: 10

Met Glu Met Phe Gln Gly Leu Leu Leu Leu Leu Leu Ser Met Gly
1               5                   10                  15

Gly Thr Trp Ala Ser Lys Glu Pro Trp Ser His Pro Gln Phe Glu Lys
            20                  25                  30

Leu Arg Pro Arg Cys Arg Pro Ile Asn Ala Thr Leu Ala Val Glu Lys
        35                  40                  45

Glu Gly Cys Pro Val Cys Ile Thr Val Asn Thr Thr Ile Cys Ala Gly
    50                  55                  60

Tyr Cys Pro Thr Met Thr Arg Val Leu Gln Gly Val Leu Pro Ala Leu
65                  70                  75                  80

Pro Gln Val Val Cys Asn Tyr Arg Asp Val Arg Phe Glu Ser Ile Arg
                85                  90                  95

Leu Pro Gly Cys Pro Arg Gly Val Asn Pro Val Val Ser Tyr Ala Val
            100                 105                 110

```
Ala Leu Ser Cys Gln Cys Ala Leu Cys Arg Arg Ser Thr Thr Asp Cys
            115                 120                 125

Gly Gly Pro Lys Asp His Pro Leu Thr Cys Asp Asp Pro Arg Phe Gln
        130                 135                 140

Asp Ser Ser Ser Lys Ala Pro Pro Ser Leu Pro Ser Pro Ser
145                 150                 155                 160

Arg Leu Pro Gly Pro Ser Asp Thr Pro Ile Leu Pro Gln
                165                 170

<210> SEQ ID NO 11
<211> LENGTH: 137
<212> TYPE: PRT
<213> ORGANISM: Homo sapiens

<400> SEQUENCE: 11

Met Glu Met Phe Gln Gly Leu Leu Leu Leu Leu Leu Ser Met Gly
1               5                   10                  15

Gly Thr Trp Ala Ser Lys Glu Pro Leu Arg Pro Arg Cys Arg Pro Ile
            20                  25                  30

Asn Ala Thr Leu Ala Val Glu Lys Glu Gly Cys Pro Val Cys Ile Thr
            35                  40                  45

Val Asn Thr Thr Ile Cys Ala Gly Tyr Cys Pro Thr Met Thr Arg Val
        50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
            100                 105                 110

Cys Arg Arg Ser Thr Thr Asp Cys Gly Gly Pro Lys Asp His Pro Leu
        115                 120                 125

Thr Cys Asp Asp Pro Arg Phe Gln Asp
            130                 135

<210> SEQ ID NO 12
<211> LENGTH: 145
<212> TYPE: PRT
<213> ORGANISM: Artificial
<220> FEATURE:
<223> OTHER INFORMATION: Synthetic

<400> SEQUENCE: 12

Met Glu Met Phe Gln Gly Leu Leu Leu Leu Leu Leu Ser Met Gly
1               5                   10                  15

Gly Thr Trp Ala Ser Lys Glu Pro Trp Ser His Pro Gln Phe Glu Lys
            20                  25                  30

Leu Arg Pro Arg Cys Arg Pro Ile Asn Ala Thr Leu Ala Val Glu Lys
        35                  40                  45

Glu Gly Cys Pro Val Cys Ile Thr Val Asn Thr Thr Ile Cys Ala Gly
    50                  55                  60

Tyr Cys Pro Thr Met Thr Arg Val Leu Gln Gly Val Leu Pro Ala Leu
65              70                  75                  80

Pro Gln Val Val Cys Asn Tyr Arg Asp Val Arg Phe Glu Ser Ile Arg
                85                  90                  95

Leu Pro Gly Cys Pro Arg Gly Val Asn Pro Val Val Ser Tyr Ala Val
            100                 105                 110
```

```
Ala Leu Ser Cys Gln Cys Ala Leu Cys Arg Arg Ser Thr Thr Asp Cys
        115                 120                 125

Gly Gly Pro Lys Asp His Pro Leu Thr Cys Asp Asp Pro Arg Phe Gln
    130                 135                 140

Asp
145

<210> SEQ ID NO 13
<211> LENGTH: 215
<212> TYPE: PRT
<213> ORGANISM: Artificial
<220> FEATURE:
<223> OTHER INFORMATION: Synthetic

<400> SEQUENCE: 13

Met Glu Met Phe Gln Gly Leu Leu Leu Leu Leu Leu Ser Met Gly
1               5                   10                  15

Gly Thr Trp Ala Ser Lys Glu Pro Trp Ser His Pro Gln Phe Glu Lys
            20                  25                  30

Leu Arg Pro Arg Cys Arg Pro Ile Asn Ala Thr Leu Ala Val Glu Lys
        35                  40                  45

Glu Gly Cys Pro Val Cys Ile Thr Val Asn Thr Thr Ile Cys Ala Gly
    50                  55                  60

Tyr Cys Pro Thr Met Thr Arg Val Leu Gln Gly Val Leu Pro Ala Leu
65                  70                  75                  80

Pro Gln Val Val Cys Asn Tyr Arg Asp Val Arg Phe Glu Ser Ile Arg
                85                  90                  95

Leu Pro Gly Cys Pro Arg Gly Val Asn Pro Val Val Ser Tyr Ala Val
            100                 105                 110

Ala Leu Ser Cys Gln Cys Ala Leu Cys Arg Arg Ser Thr Thr Asp Cys
        115                 120                 125

Gly Gly Pro Lys Asp His Pro Leu Thr Cys Asp Asp Pro Arg Phe Gln
    130                 135                 140

Asp Ser Pro Ala Ser Ala Ser Thr Gln Thr Ser Trp Thr Pro Arg Asp
145                 150                 155                 160

Leu Val Ser Ser Gln Thr Gln Thr Gln Ser Cys Val Pro Pro Thr Ala
                165                 170                 175

Gly Ala Arg Gln Ala Pro Glu Ser Pro Ser Thr Ile Pro Val Pro Ser
            180                 185                 190

His Pro Ser Ser Pro Leu Pro Val Pro Leu Pro Ser Arg Pro Gln Asn
        195                 200                 205

Ser Thr Leu Arg Pro Gly Pro
    210                 215

<210> SEQ ID NO 14
<211> LENGTH: 183
<212> TYPE: PRT
<213> ORGANISM: Artificial
<220> FEATURE:
<223> OTHER INFORMATION: Synthetic

<400> SEQUENCE: 14

Leu Arg Pro Arg Cys Arg Pro Ile Asn Ala Thr Leu Ala Val Glu Lys
1               5                   10                  15

Glu Gly Cys Pro Val Cys Ile Thr Val Asn Thr Thr Ile Cys Ala Gly
            20                  25                  30

Tyr Cys Pro Thr Met Thr Arg Val Leu Gln Gly Val Leu Pro Ala Leu
        35                  40                  45
```

Pro Gln Val Val Cys Asn Tyr Arg Asp Val Arg Phe Glu Ser Ile Arg
    50                  55                  60

Leu Pro Gly Cys Pro Arg Gly Val Asn Pro Val Ser Tyr Ala Val
65                  70                  75                  80

Ala Leu Ser Cys Gln Cys Ala Leu Cys Arg Arg Ser Thr Thr Asp Cys
                85                  90                  95

Gly Gly Pro Lys Asp His Pro Leu Thr Cys Asp Asp Pro Arg Phe Gln
                100                 105                 110

Asp Ser Pro Ala Ser Ala Ser Thr Gln Thr Ser Trp Thr Pro Arg Asp
                115                 120                 125

Leu Val Ser Ser Gln Thr Gln Thr Gln Ser Cys Val Pro Pro Thr Ala
            130                 135                 140

Gly Ala Arg Gln Ala Pro Glu Ser Pro Ser Thr Ile Pro Val Pro Ser
145                 150                 155                 160

His Pro Ser Ser Pro Leu Pro Val Pro Leu Pro Ser Arg Pro Gln Asn
                165                 170                 175

Ser Thr Leu Arg Pro Gly Pro
            180

<210> SEQ ID NO 15
<211> LENGTH: 217
<212> TYPE: PRT
<213> ORGANISM: Homo sapiens

<400> SEQUENCE: 15

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
                20                  25                  30

Ser Arg Leu Phe Asp Asn Ala Met Leu Arg Ala His Arg Leu His Gln
            35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe
    210                 215

```
<210> SEQ ID NO 16
<211> LENGTH: 191
<212> TYPE: PRT
<213> ORGANISM: Homo sapiens

<400> SEQUENCE: 16

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190

<210> SEQ ID NO 17
<211> LENGTH: 27
<212> TYPE: PRT
<213> ORGANISM: Homo sapiens

<400> SEQUENCE: 17

Met Ala Thr Gly Ser Arg Thr Ser Leu Leu Leu Ala Phe Gly Leu Leu
1               5                   10                  15

Cys Leu Pro Trp Leu Gln Glu Gly Ser Gln Ala
            20                  25

<210> SEQ ID NO 18
<211> LENGTH: 22
<212> TYPE: PRT
<213> ORGANISM: Artificial
<220> FEATURE:
<223> OTHER INFORMATION: Synthetic

<400> SEQUENCE: 18

Asp Tyr Lys Asp His Asp Gly Asp Tyr Lys Asp His Asp Ile Asp Tyr
1               5                   10                  15

Lys Asp Asp Asp Asp Lys
            20

<210> SEQ ID NO 19
<211> LENGTH: 239
<212> TYPE: PRT
<213> ORGANISM: Artificial
<220> FEATURE:
```

<223> OTHER INFORMATION: Synthetic

<400> SEQUENCE: 19

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Asp Tyr Lys Asp His Asp
            20                  25                  30

Gly Asp Tyr Lys Asp His Asp Ile Asp Tyr Lys Asp Asp Asp Asp Lys
        35                  40                  45

Phe Pro Thr Ile Pro Leu Ser Arg Leu Phe Asp Asn Ala Met Leu Arg
    50                  55                  60

Ala His Arg Leu His Gln Leu Ala Phe Asp Thr Tyr Gln Glu Phe Glu
65                  70                  75                  80

Glu Ala Tyr Ile Pro Lys Glu Gln Lys Tyr Ser Phe Leu Gln Asn Pro
                85                  90                  95

Gln Thr Ser Leu Cys Phe Ser Glu Ser Ile Pro Thr Pro Ser Asn Arg
            100                 105                 110

Glu Glu Thr Gln Gln Lys Ser Asn Leu Glu Leu Leu Arg Ile Ser Leu
        115                 120                 125

Leu Leu Ile Gln Ser Trp Leu Glu Pro Val Gln Phe Leu Arg Ser Val
130                 135                 140

Phe Ala Asn Ser Leu Val Tyr Gly Ala Ser Asp Ser Asn Val Tyr Asp
145                 150                 155                 160

Leu Leu Lys Asp Leu Glu Glu Gly Ile Gln Thr Leu Met Gly Arg Leu
                165                 170                 175

Glu Asp Gly Ser Pro Arg Thr Gly Gln Ile Phe Lys Gln Thr Tyr Ser
            180                 185                 190

Lys Phe Asp Thr Asn Ser His Asn Asp Asp Ala Leu Leu Lys Asn Tyr
        195                 200                 205

Gly Leu Leu Tyr Cys Phe Arg Lys Asp Met Asp Lys Val Glu Thr Phe
    210                 215                 220

Leu Arg Ile Val Gln Cys Arg Ser Val Glu Gly Ser Cys Gly Phe
225                 230                 235
```

<210> SEQ ID NO 20
<211> LENGTH: 247
<212> TYPE: PRT
<213> ORGANISM: Artificial
<220> FEATURE:
<223> OTHER INFORMATION: Synthetic

<400> SEQUENCE: 20

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Asp Tyr Lys Asp His Asp
            20                  25                  30

Gly Asp Tyr Lys Asp His Asp Ile Asp Tyr Lys Asp Asp Asp Asp Lys
        35                  40                  45

Phe Pro Thr Ile Pro Leu Ser Arg Leu Phe Asp Asn Ala Met Leu Arg
    50                  55                  60

Ala His Arg Leu His Gln Leu Ala Phe Asp Thr Tyr Gln Glu Phe Glu
65                  70                  75                  80

Glu Ala Tyr Ile Pro Lys Glu Gln Lys Tyr Ser Phe Leu Gln Asn Pro
                85                  90                  95

Gln Thr Ser Leu Cys Phe Ser Glu Ser Ile Pro Thr Pro Ser Asn Arg
            100                 105                 110
```

```
Glu Glu Thr Gln Gln Lys Ser Asn Leu Glu Leu Leu Arg Ile Ser Leu
            115                 120                 125

Leu Leu Ile Gln Ser Trp Leu Glu Pro Val Gln Phe Leu Arg Ser Val
        130                 135                 140

Phe Ala Asn Ser Leu Val Tyr Gly Ala Ser Asp Ser Asn Val Tyr Asp
145                 150                 155                 160

Leu Leu Lys Asp Leu Glu Glu Gly Ile Gln Thr Leu Met Gly Arg Leu
                165                 170                 175

Glu Asp Gly Ser Pro Arg Thr Gly Gln Ile Phe Lys Gln Thr Tyr Ser
            180                 185                 190

Lys Phe Asp Thr Asn Ser His Asn Asp Asp Ala Leu Leu Lys Asn Tyr
        195                 200                 205

Gly Leu Leu Tyr Cys Phe Arg Lys Asp Met Asp Lys Val Glu Thr Phe
210                 215                 220

Leu Arg Ile Val Gln Cys Arg Ser Val Glu Gly Ser Cys Gly Phe His
225                 230                 235                 240

His His His His His His
            245

<210> SEQ ID NO 21
<211> LENGTH: 269
<212> TYPE: PRT
<213> ORGANISM: Artificial
<220> FEATURE:
<223> OTHER INFORMATION: Synthetic

<400> SEQUENCE: 21

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe Ser
            180                 185                 190

Pro Ala Ser Ala Ser Thr Gln Thr Ser Trp Thr Pro Arg Asp Leu Val
        195                 200                 205

Ser Ser Gln Thr Gln Thr Gln Ser Cys Val Pro Pro Thr Ala Gly Ala
    210                 215                 220
```

```
Arg Gln Ala Pro Glu Ser Pro Ser Thr Ile Pro Val Pro Ser His Pro
225                 230                 235                 240

Ser Ser Pro Leu Pro Val Pro Leu Pro Ser Arg Pro Gln Asn Ser Thr
            245                 250                 255

Leu Arg Pro Gly Pro His His His His His His His
            260                 265
```

<210> SEQ ID NO 22
<211> LENGTH: 225
<212> TYPE: PRT
<213> ORGANISM: Artificial
<220> FEATURE:
<223> OTHER INFORMATION: Synthetic

<400> SEQUENCE: 22

```
Ser Pro Ala Ser Ala Ser Thr Gln Thr Ser Trp Thr Pro Arg Asp Leu
1               5                   10                  15

Val Ser Gln Thr Gln Thr Gln Ser Cys Val Pro Pro Thr Ala Gly
            20                  25                  30

Ala Arg Phe Pro Thr Ile Pro Leu Ser Arg Leu Phe Asp Asn Ala Met
            35                  40                  45

Leu Arg Ala His Arg Leu His Gln Leu Ala Phe Asp Thr Tyr Gln Glu
    50                  55                  60

Phe Glu Glu Ala Tyr Ile Pro Lys Glu Gln Lys Tyr Ser Phe Leu Gln
65                  70                  75                  80

Asn Pro Gln Thr Ser Leu Cys Phe Ser Glu Ser Ile Pro Thr Pro Ser
                85                  90                  95

Asn Arg Glu Glu Thr Gln Gln Lys Ser Asn Leu Glu Leu Leu Arg Ile
            100                 105                 110

Ser Leu Leu Leu Ile Gln Ser Trp Leu Glu Pro Val Gln Phe Leu Arg
        115                 120                 125

Ser Val Phe Ala Asn Ser Leu Val Tyr Gly Ala Ser Asp Ser Asn Val
    130                 135                 140

Tyr Asp Leu Leu Lys Asp Leu Glu Glu Gly Ile Gln Thr Leu Met Gly
145                 150                 155                 160

Arg Leu Glu Asp Gly Ser Pro Arg Thr Gly Gln Ile Phe Lys Gln Thr
                165                 170                 175

Tyr Ser Lys Phe Asp Thr Asn Ser His Asn Asp Asp Ala Leu Leu Lys
            180                 185                 190

Asn Tyr Gly Leu Leu Tyr Cys Phe Arg Lys Asp Met Asp Lys Val Glu
        195                 200                 205

Thr Phe Leu Arg Ile Val Gln Cys Arg Ser Val Glu Gly Ser Cys Gly
    210                 215                 220

Phe
225
```

<210> SEQ ID NO 23
<211> LENGTH: 261
<212> TYPE: PRT
<213> ORGANISM: Artificial
<220> FEATURE:
<223> OTHER INFORMATION: Synthetic

<400> SEQUENCE: 23

```
Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
```

-continued

```
                20                  25                  30
Glu Ala Tyr Ile Pro Lys Glu Gln Lys Tyr Ser Phe Leu Gln Asn Pro
             35                  40                  45
Gln Thr Ser Leu Cys Phe Ser Glu Ser Ile Pro Thr Pro Ser Asn Arg
 50                  55                  60
Glu Glu Thr Gln Gln Lys Ser Asn Leu Glu Leu Leu Arg Ile Ser Leu
 65                  70                  75                  80
Leu Leu Ile Gln Ser Trp Leu Glu Pro Val Gln Phe Leu Arg Ser Val
                 85                  90                  95
Phe Ala Asn Ser Leu Val Tyr Gly Ala Ser Asp Ser Asn Val Tyr Asp
            100                 105                 110
Leu Leu Lys Asp Leu Glu Glu Gly Ile Gln Thr Leu Met Gly Arg Leu
        115                 120                 125
Glu Asp Gly Ser Pro Arg Thr Gly Gln Ile Phe Lys Gln Thr Tyr Ser
    130                 135                 140
Lys Phe Asp Thr Asn Ser His Asn Asp Asp Ala Leu Leu Lys Asn Tyr
145                 150                 155                 160
Gly Leu Leu Tyr Cys Phe Arg Lys Asp Met Asp Lys Val Glu Thr Phe
                165                 170                 175
Leu Arg Ile Val Gln Cys Arg Ser Val Glu Gly Ser Cys Gly Phe Ser
            180                 185                 190
Pro Ala Ser Ala Ser Thr Gln Thr Ser Trp Thr Pro Arg Asp Leu Val
        195                 200                 205
Ser Ser Gln Thr Gln Thr Gln Ser Cys Val Pro Pro Thr Ala Gly Ala
    210                 215                 220
Arg Gln Ala Pro Glu Ser Pro Ser Thr Ile Pro Val Pro Ser His Pro
225                 230                 235                 240
Ser Ser Pro Leu Pro Val Pro Leu Pro Ser Arg Pro Gln Asn Ser Thr
                245                 250                 255
Leu Arg Pro Gly Pro
            260

<210> SEQ ID NO 24
<211> LENGTH: 317
<212> TYPE: PRT
<213> ORGANISM: Artificial
<220> FEATURE:
<223> OTHER INFORMATION: Synthetic

<400> SEQUENCE: 24

Met Ala Thr Gly Ser Arg Thr Ser Leu Leu Leu Ala Phe Gly Leu Leu
 1               5                  10                  15
Cys Leu Pro Trp Leu Gln Glu Gly Ser Ala Asp Tyr Lys Asp His Asp
                20                  25                  30
Gly Asp Tyr Lys Asp His Asp Ile Asp Tyr Lys Asp Asp Asp Asp Lys
             35                  40                  45
Phe Pro Thr Ile Pro Leu Ser Arg Leu Phe Asp Asn Ala Met Leu Arg
 50                  55                  60
Ala His Arg Leu His Gln Leu Ala Phe Asp Thr Tyr Gln Glu Phe Glu
 65                  70                  75                  80
Glu Ala Tyr Ile Pro Lys Glu Gln Lys Tyr Ser Phe Leu Gln Asn Pro
                 85                  90                  95
Gln Thr Ser Leu Cys Phe Ser Glu Ser Ile Pro Thr Pro Ser Asn Arg
            100                 105                 110
Glu Glu Thr Gln Gln Lys Ser Asn Leu Glu Leu Leu Arg Ile Ser Leu
```

```
                115                 120                 125
Leu Leu Ile Gln Ser Trp Leu Glu Pro Val Gln Phe Leu Arg Ser Val
    130                 135                 140

Phe Ala Asn Ser Leu Val Tyr Gly Ala Ser Asp Ser Asn Val Tyr Asp
145                 150                 155                 160

Leu Leu Lys Asp Leu Glu Glu Gly Ile Gln Thr Leu Met Gly Arg Leu
                165                 170                 175

Glu Asp Gly Ser Pro Arg Thr Gly Gln Ile Phe Lys Gln Thr Tyr Ser
            180                 185                 190

Lys Phe Asp Thr Asn Ser His Asn Asp Ala Leu Leu Lys Asn Tyr
        195                 200                 205

Gly Leu Leu Tyr Cys Phe Arg Lys Asp Met Asp Lys Val Glu Thr Phe
    210                 215                 220

Leu Arg Ile Val Gln Cys Arg Ser Val Glu Gly Ser Cys Gly Phe Ser
225                 230                 235                 240

Pro Ala Ser Ala Ser Thr Gln Thr Ser Trp Thr Pro Arg Asp Leu Val
                245                 250                 255

Ser Ser Gln Thr Gln Thr Gln Ser Cys Val Pro Pro Thr Ala Gly Ala
            260                 265                 270

Arg Gln Ala Pro Glu Ser Pro Ser Thr Ile Pro Val Pro Ser His Pro
        275                 280                 285

Ser Ser Pro Leu Pro Val Pro Leu Pro Ser Arg Pro Gln Ala Ser Thr
    290                 295                 300

Leu Arg Pro Gly Pro His His His His His His
305                 310                 315

<210> SEQ ID NO 25
<211> LENGTH: 309
<212> TYPE: PRT
<213> ORGANISM: Artificial
<220> FEATURE:
<223> OTHER INFORMATION: Synthetic

<400> SEQUENCE: 25

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Asp Tyr Lys Asp His Asp
                20                  25                  30

Gly Asp Tyr Lys Asp His Asp Ile Asp Tyr Lys Asp Asp Asp Lys
            35                  40                  45

Phe Pro Thr Ile Pro Leu Ser Arg Leu Phe Asp Asn Ala Met Leu Arg
    50                  55                  60

Ala His Arg Leu His Gln Leu Ala Phe Asp Thr Tyr Gln Glu Phe Glu
65                  70                  75                  80

Glu Ala Tyr Ile Pro Lys Glu Gln Lys Tyr Ser Phe Leu Gln Asn Pro
                85                  90                  95

Gln Thr Ser Leu Cys Phe Ser Glu Ser Ile Pro Thr Pro Ser Asn Arg
            100                 105                 110

Glu Glu Thr Gln Gln Lys Ser Asn Leu Glu Leu Leu Arg Ile Ser Leu
        115                 120                 125

Leu Leu Ile Gln Ser Trp Leu Glu Pro Val Gln Phe Leu Arg Ser Val
    130                 135                 140

Phe Ala Asn Ser Leu Val Tyr Gly Ala Ser Asp Ser Asn Val Tyr Asp
145                 150                 155                 160

Leu Leu Lys Asp Leu Glu Glu Gly Ile Gln Thr Leu Met Gly Arg Leu
```

```
                        165                 170                 175
Glu Asp Gly Ser Pro Arg Thr Gly Gln Ile Phe Lys Gln Thr Tyr Ser
                    180                 185                 190

Lys Phe Asp Thr Asn Ser His Asn Asp Asp Ala Leu Leu Lys Asn Tyr
                195                 200                 205

Gly Leu Leu Tyr Cys Phe Arg Lys Asp Met Asp Lys Val Glu Thr Phe
            210                 215                 220

Leu Arg Ile Val Gln Cys Arg Ser Val Glu Gly Ser Cys Gly Phe Ser
225                 230                 235                 240

Pro Ala Ser Ala Ser Thr Gln Thr Ser Trp Thr Pro Arg Asp Leu Val
                245                 250                 255

Ser Ser Gln Thr Gln Thr Gln Ser Cys Val Pro Pro Thr Ala Gly Ala
                260                 265                 270

Arg Gln Ala Pro Glu Ser Pro Ser Thr Ile Pro Val Pro Ser His Pro
            275                 280                 285

Ser Ser Pro Leu Pro Val Pro Leu Pro Ser Arg Pro Gln Ala Ser Thr
            290                 295                 300

Leu Arg Pro Gly Pro
305

<210> SEQ ID NO 26
<211> LENGTH: 261
<212> TYPE: PRT
<213> ORGANISM: Artificial
<220> FEATURE:
<223> OTHER INFORMATION: Synthetic

<400> SEQUENCE: 26

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
                20                  25                  30

Glu Ala Tyr Ile Pro Lys Glu Gln Lys Tyr Ser Phe Leu Gln Asn Pro
            35                  40                  45

Gln Thr Ser Leu Cys Phe Ser Glu Ser Ile Pro Thr Pro Ser Asn Arg
50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe Ser
            180                 185                 190

Pro Ala Ser Ala Ser Thr Gln Thr Ser Trp Thr Pro Arg Asp Leu Val
        195                 200                 205

Ser Ser Gln Thr Gln Thr Gln Ser Cys Val Pro Pro Thr Ala Gly Ala
```

```
             210                 215                 220
Arg Gln Ala Pro Glu Ser Pro Ser Thr Ile Pro Val Pro Ser His Pro
225                 230                 235                 240

Ser Ser Pro Leu Pro Val Pro Leu Pro Ser Arg Pro Gln Ala Ser Thr
                245                 250                 255

Leu Arg Pro Gly Pro
            260

<210> SEQ ID NO 27
<211> LENGTH: 293
<212> TYPE: PRT
<213> ORGANISM: Artificial
<220> FEATURE:
<223> OTHER INFORMATION: Synthetic

<400> SEQUENCE: 27

Met Ala Thr Gly Ser Arg Thr Ser Leu Leu Leu Ala Phe Gly Leu Leu
1               5                  10                  15

Cys Leu Pro Trp Leu Gln Glu Gly Ser Ala Ser Pro Ala Ser Ala Ser
                20                  25                  30

Thr Gln Thr Ser Trp Thr Pro Arg Asp Leu Val Ser Ser Gln Thr Gln
            35                  40                  45

Thr Gln Ser Cys Val Pro Pro Thr Ala Gly Ala Arg Phe Pro Thr Ile
        50                  55                  60

Pro Leu Ser Arg Leu Phe Asp Asn Ala Met Leu Arg Ala His Arg Leu
65                  70                  75                  80

His Gln Leu Ala Phe Asp Thr Tyr Gln Glu Phe Glu Glu Ala Tyr Ile
                85                  90                  95

Pro Lys Glu Gln Lys Tyr Ser Phe Leu Gln Asn Pro Gln Thr Ser Leu
            100                 105                 110

Cys Phe Ser Glu Ser Ile Pro Thr Pro Ser Asn Arg Glu Glu Thr Gln
        115                 120                 125

Gln Lys Ser Asn Leu Glu Leu Leu Arg Ile Ser Leu Leu Leu Ile Gln
    130                 135                 140

Ser Trp Leu Glu Pro Val Gln Phe Leu Arg Ser Val Phe Ala Asn Ser
145                 150                 155                 160

Leu Val Tyr Gly Ala Ser Asp Ser Asn Val Tyr Asp Leu Leu Lys Asp
                165                 170                 175

Leu Glu Glu Gly Ile Gln Thr Leu Met Gly Arg Leu Glu Asp Gly Ser
            180                 185                 190

Pro Arg Thr Gly Gln Ile Phe Lys Gln Thr Tyr Ser Lys Phe Asp Thr
        195                 200                 205

Asn Ser His Asn Asp Asp Ala Leu Leu Lys Asn Tyr Gly Leu Leu Tyr
    210                 215                 220

Cys Phe Arg Lys Asp Met Asp Lys Val Glu Thr Phe Leu Arg Ile Val
225                 230                 235                 240

Gln Cys Arg Ser Val Glu Gly Ser Cys Gly Phe Ser Pro Ala Ser Ala
                245                 250                 255

Ser Thr Gln Thr Ser Trp Thr Pro Arg Asp Leu Val Ser Ser Gln Thr
            260                 265                 270

Gln Thr Gln Ser Cys Val Pro Pro Thr Ala Gly Ala Arg His His His
        275                 280                 285

His His His His His
    290
```

```
<210> SEQ ID NO 28
<211> LENGTH: 285
<212> TYPE: PRT
<213> ORGANISM: Artificial
<220> FEATURE:
<223> OTHER INFORMATION: Synthetic

<400> SEQUENCE: 28

Met Ala Thr Gly Ser Arg Thr Ser Leu Leu Ala Phe Gly Leu Leu
1               5                   10                  15

Cys Leu Pro Trp Leu Gln Glu Gly Ser Ala Ser Pro Ala Ser Ala Ser
            20                  25                  30

Thr Gln Thr Ser Trp Thr Pro Arg Asp Leu Val Ser Ser Gln Thr Gln
        35                  40                      45

Thr Gln Ser Cys Val Pro Pro Thr Ala Gly Ala Arg Phe Pro Thr Ile
    50                  55                      60

Pro Leu Ser Arg Leu Phe Asp Asn Ala Met Leu Arg Ala His Arg Leu
65                  70                  75                  80

His Gln Leu Ala Phe Asp Thr Tyr Gln Glu Phe Glu Glu Ala Tyr Ile
                85                  90                  95

Pro Lys Glu Gln Lys Tyr Ser Phe Leu Gln Asn Pro Gln Thr Ser Leu
            100                 105                 110

Cys Phe Ser Glu Ser Ile Pro Thr Pro Ser Asn Arg Glu Glu Thr Gln
        115                 120                 125

Gln Lys Ser Asn Leu Glu Leu Leu Arg Ile Ser Leu Leu Ile Gln
    130                 135                 140

Ser Trp Leu Glu Pro Val Gln Phe Leu Arg Ser Val Phe Ala Asn Ser
145                 150                 155                 160

Leu Val Tyr Gly Ala Ser Asp Ser Asn Val Tyr Asp Leu Leu Lys Asp
                165                 170                 175

Leu Glu Glu Gly Ile Gln Thr Leu Met Gly Arg Leu Glu Asp Gly Ser
            180                 185                 190

Pro Arg Thr Gly Gln Ile Phe Lys Gln Thr Tyr Ser Lys Phe Asp Thr
        195                 200                 205

Asn Ser His Asn Asp Asp Ala Leu Leu Lys Asn Tyr Gly Leu Leu Tyr
    210                 215                 220

Cys Phe Arg Lys Asp Met Asp Lys Val Glu Thr Phe Leu Arg Ile Val
225                 230                 235                 240

Gln Cys Arg Ser Val Glu Gly Ser Cys Gly Phe Ser Pro Ala Ser Ala
                245                 250                 255

Ser Thr Gln Thr Ser Trp Thr Pro Arg Asp Leu Val Ser Ser Gln Thr
            260                 265                 270

Gln Thr Gln Ser Cys Val Pro Pro Thr Ala Gly Ala Arg
        275                 280                 285

<210> SEQ ID NO 29
<211> LENGTH: 259
<212> TYPE: PRT
<213> ORGANISM: Artificial
<220> FEATURE:
<223> OTHER INFORMATION: Synthetic

<400> SEQUENCE: 29

Ser Pro Ala Ser Ala Ser Thr Gln Thr Ser Trp Thr Pro Arg Asp Leu
1               5                   10                  15

Val Ser Ser Gln Thr Gln Thr Gln Ser Cys Val Pro Pro Thr Ala Gly
            20                  25                  30
```

```
Ala Arg Phe Pro Thr Ile Pro Leu Ser Arg Leu Phe Asp Asn Ala Met
        35                  40                  45

Leu Arg Ala His Arg Leu His Gln Leu Ala Phe Asp Thr Tyr Gln Glu
 50                  55                  60

Phe Glu Glu Ala Tyr Ile Pro Lys Glu Gln Lys Tyr Ser Phe Leu Gln
 65                  70                  75                  80

Asn Pro Gln Thr Ser Leu Cys Phe Ser Glu Ser Ile Pro Thr Pro Ser
                 85                  90                  95

Asn Arg Glu Glu Thr Gln Gln Lys Ser Asn Leu Glu Leu Leu Arg Ile
            100                 105                 110

Ser Leu Leu Leu Ile Gln Ser Trp Leu Glu Pro Val Gln Phe Leu Arg
        115                 120                 125

Ser Val Phe Ala Asn Ser Leu Val Tyr Gly Ala Ser Asp Ser Asn Val
    130                 135                 140

Tyr Asp Leu Leu Lys Asp Leu Glu Glu Gly Ile Gln Thr Leu Met Gly
145                 150                 155                 160

Arg Leu Glu Asp Gly Ser Pro Arg Thr Gly Gln Ile Phe Lys Gln Thr
                165                 170                 175

Tyr Ser Lys Phe Asp Thr Asn Ser His Asn Asp Asp Ala Leu Leu Lys
            180                 185                 190

Asn Tyr Gly Leu Leu Tyr Cys Phe Arg Lys Asp Met Asp Lys Val Glu
        195                 200                 205

Thr Phe Leu Arg Ile Val Gln Cys Arg Ser Val Glu Gly Ser Cys Gly
    210                 215                 220

Phe Ser Pro Ala Ser Ala Ser Thr Gln Thr Ser Trp Thr Pro Arg Asp
225                 230                 235                 240

Leu Val Ser Ser Gln Thr Gln Thr Gln Ser Cys Val Pro Pro Thr Ala
                245                 250                 255

Gly Ala Arg

<210> SEQ ID NO 30
<211> LENGTH: 259
<212> TYPE: PRT
<213> ORGANISM: Artificial
<220> FEATURE:
<223> OTHER INFORMATION: Synthetic

<400> SEQUENCE: 30

Met Ala Thr Gly Ser Arg Thr Ser Leu Leu Leu Ala Phe Gly Leu Leu
 1               5                  10                  15

Cys Leu Pro Trp Leu Gln Glu Gly Ser Ala Phe Pro Thr Ile Pro Leu
                20                  25                  30

Ser Arg Leu Phe Asp Asn Ala Met Leu Arg Ala His Arg Leu His Gln
            35                  40                  45

Leu Ala Phe Asp Thr Tyr Gln Glu Phe Glu Glu Ala Tyr Ile Pro Lys
 50                  55                  60

Glu Gln Lys Tyr Ser Phe Leu Gln Asn Pro Gln Thr Ser Leu Cys Phe
 65                  70                  75                  80

Ser Glu Ser Ile Pro Thr Pro Ser Asn Arg Glu Glu Thr Gln Gln Lys
                 85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
```

```
            130                 135                 140
Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
            195                 200                 205

Arg Ser Val Glu Gly Ser Cys Gly Phe Ser Pro Ala Ser Ala Ser Thr
            210                 215                 220

Gln Thr Ser Trp Thr Pro Arg Asp Leu Val Ser Ser Gln Thr Gln Thr
225                 230                 235                 240

Gln Ser Cys Val Pro Pro Thr Ala Gly Ala Arg His His His His His
                245                 250                 255

His His His

<210> SEQ ID NO 31
<211> LENGTH: 251
<212> TYPE: PRT
<213> ORGANISM: Artificial
<220> FEATURE:
<223> OTHER INFORMATION: Synthetic

<400> SEQUENCE: 31

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
                20                  25                  30

Ser Arg Leu Phe Asp Asn Ala Met Leu Arg Ala His Arg Leu His Gln
            35                  40                  45

Leu Ala Phe Asp Thr Tyr Gln Glu Phe Glu Glu Ala Tyr Ile Pro Lys
        50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
            195                 200                 205

Arg Ser Val Glu Gly Ser Cys Gly Phe Ser Pro Ala Ser Ala Ser Thr
            210                 215                 220

Gln Thr Ser Trp Thr Pro Arg Asp Leu Val Ser Ser Gln Thr Gln Thr
225                 230                 235                 240
```

```
Gln Ser Cys Val Pro Pro Thr Ala Gly Ala Arg
            245                 250
```

<210> SEQ ID NO 32
<211> LENGTH: 225
<212> TYPE: PRT
<213> ORGANISM: Artificial
<220> FEATURE:
<223> OTHER INFORMATION: Synthetic

<400> SEQUENCE: 32

```
Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe Ser
            180                 185                 190

Pro Ala Ser Ala Ser Thr Gln Thr Ser Trp Thr Pro Arg Asp Leu Val
        195                 200                 205

Ser Ser Gln Thr Gln Thr Gln Ser Cys Val Pro Pro Thr Ala Gly Ala
    210                 215                 220

Arg
225
```

<210> SEQ ID NO 33
<211> LENGTH: 261
<212> TYPE: PRT
<213> ORGANISM: Artificial
<220> FEATURE:
<223> OTHER INFORMATION: Synthetic

<400> SEQUENCE: 33

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
```

```
                50                  55                  60
Glu Gln Lys Tyr Ser Phe Leu Gln Asn Pro Gln Thr Ser Leu Cys Phe
 65                  70                  75                  80

Ser Glu Ser Ile Pro Thr Pro Ser Asn Arg Glu Glu Thr Gln Gln Lys
                 85                  90                  95

Ser Asn Leu Glu Leu Leu Arg Ile Ser Leu Leu Ile Gln Ser Trp
                100                 105                 110

Leu Glu Pro Val Gln Phe Leu Arg Ser Val Phe Ala Asn Ser Leu Val
                115                 120                 125

Tyr Gly Ala Ser Asp Ser Asn Val Tyr Asp Leu Leu Lys Asp Leu Glu
                130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
                180                 185                 190

Arg Lys Asp Met Asp Lys Val Glu Thr Phe Leu Arg Ile Val Gln Cys
                195                 200                 205

Arg Ser Val Glu Gly Ser Cys Gly Phe Gln Ala Pro Glu Ser Pro Ser
                210                 215                 220

Thr Ile Pro Val Pro Ser His Pro Ser Ser Pro Leu Pro Val Pro Leu
225                 230                 235                 240

Pro Ser Arg Pro Gln Asn Ser Thr Leu Arg Pro Gly Pro His His His
                245                 250                 255

His His His His His
                260

<210> SEQ ID NO 34
<211> LENGTH: 253
<212> TYPE: PRT
<213> ORGANISM: Artificial
<220> FEATURE:
<223> OTHER INFORMATION: Synthetic

<400> SEQUENCE: 34

Met Ala Thr Gly Ser Arg Thr Ser Leu Leu Leu Ala Phe Gly Leu Leu
 1               5                  10                  15

Cys Leu Pro Trp Leu Gln Glu Gly Ser Ala Phe Pro Thr Ile Pro Leu
                 20                  25                  30

Ser Arg Leu Phe Asp Asn Ala Met Leu Arg Ala His Arg Leu His Gln
                 35                  40                  45

Leu Ala Phe Asp Thr Tyr Gln Glu Phe Glu Glu Ala Tyr Ile Pro Lys
                 50                  55                  60

Glu Gln Lys Tyr Ser Phe Leu Gln Asn Pro Gln Thr Ser Leu Cys Phe
 65                  70                  75                  80

Ser Glu Ser Ile Pro Thr Pro Ser Asn Arg Glu Glu Thr Gln Gln Lys
                 85                  90                  95

Ser Asn Leu Glu Leu Leu Arg Ile Ser Leu Leu Leu Ile Gln Ser Trp
                100                 105                 110

Leu Glu Pro Val Gln Phe Leu Arg Ser Val Phe Ala Asn Ser Leu Val
                115                 120                 125

Tyr Gly Ala Ser Asp Ser Asn Val Tyr Asp Leu Leu Lys Asp Leu Glu
                130                 135                 140

Glu Gly Ile Gln Thr Leu Met Gly Arg Leu Glu Asp Gly Ser Pro Arg
```

```
                145                 150                 155                 160
Thr Gly Gln Ile Phe Lys Gln Thr Tyr Ser Lys Phe Asp Thr Asn Ser
                    165                 170                 175

His Asn Asp Asp Ala Leu Leu Lys Asn Tyr Gly Leu Leu Tyr Cys Phe
                    180                 185                 190

Arg Lys Asp Met Asp Lys Val Glu Thr Phe Leu Arg Ile Val Gln Cys
                    195                 200                 205

Arg Ser Val Glu Gly Ser Cys Gly Phe Gln Ala Pro Glu Ser Pro Ser
210                 215                 220

Thr Ile Pro Val Pro Ser His Pro Ser Ser Pro Leu Pro Val Pro Leu
225                 230                 235                 240

Pro Ser Arg Pro Gln Asn Ser Thr Leu Arg Pro Gly Pro
                    245                 250

<210> SEQ ID NO 35
<211> LENGTH: 227
<212> TYPE: PRT
<213> ORGANISM: Artificial
<220> FEATURE:
<223> OTHER INFORMATION: Synthetic

<400> SEQUENCE: 35

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
                20                  25                  30

Glu Ala Tyr Ile Pro Lys Glu Gln Lys Tyr Ser Phe Leu Gln Asn Pro
            35                  40                  45

Gln Thr Ser Leu Cys Phe Ser Glu Ser Ile Pro Thr Pro Ser Asn Arg
        50                  55                  60

Glu Glu Thr Gln Gln Lys Ser Asn Leu Glu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
                100                 105                 110

Leu Leu Lys Asp Leu Glu Glu Gly Ile Gln Thr Leu Met Gly Arg Leu
                115                 120                 125

Glu Asp Gly Ser Pro Arg Thr Gly Gln Ile Phe Lys Gln Thr Tyr Ser
                130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe Gln
                180                 185                 190

Ala Pro Glu Ser Pro Ser Thr Ile Pro Val Pro Ser His Pro Ser Ser
                195                 200                 205

Pro Leu Pro Val Pro Leu Pro Ser Arg Pro Gln Asn Ser Thr Leu Arg
210                 215                 220

Pro Gly Pro
225

<210> SEQ ID NO 36
<211> LENGTH: 295
<212> TYPE: PRT
```

<213> ORGANISM: Artificial
<220> FEATURE:
<223> OTHER INFORMATION: Synthetic

<400> SEQUENCE: 36

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Pro Ala Ser Ala Ser
            20                  25                  30

Thr Gln Thr Ser Trp Thr Pro Arg Asp Leu Val Ser Ser Gln Thr Gln
        35                  40                  45

Thr Gln Ser Cys Val Pro Pro Thr Ala Gly Ala Arg Phe Pro Thr Ile
    50                  55                  60

Pro Leu Ser Arg Leu Phe Asp Asn Ala Met Leu Arg Ala His Arg Leu
65                  70                  75                  80

His Gln Leu Ala Phe Asp Thr Tyr Gln Glu Phe Glu Glu Ala Tyr Ile
                85                  90                  95

Pro Lys Glu Gln Lys Tyr Ser Phe Leu Gln Asn Pro Gln Thr Ser Leu
            100                 105                 110

Cys Phe Ser Glu Ser Ile Pro Thr Pro Ser Asn Arg Glu Glu Thr Gln
        115                 120                 125

Gln Lys Ser Asn Leu Glu Leu Leu Arg Ile Ser Leu Leu Leu Ile Gln
    130                 135                 140

Ser Trp Leu Glu Pro Val Gln Phe Leu Arg Ser Val Phe Ala Asn Ser
145                 150                 155                 160

Leu Val Tyr Gly Ala Ser Asp Ser Asn Val Tyr Asp Leu Leu Lys Asp
                165                 170                 175

Leu Glu Glu Gly Ile Gln Thr Leu Met Gly Arg Leu Glu Asp Gly Ser
            180                 185                 190

Pro Arg Thr Gly Gln Ile Phe Lys Gln Thr Tyr Ser Lys Phe Asp Thr
        195                 200                 205

Asn Ser His Asn Asp Asp Ala Leu Leu Lys Asn Tyr Gly Leu Leu Tyr
    210                 215                 220

Cys Phe Arg Lys Asp Met Asp Lys Val Glu Thr Phe Leu Arg Ile Val
225                 230                 235                 240

Gln Cys Arg Ser Val Glu Gly Ser Cys Gly Phe Gln Ala Pro Glu Ser
                245                 250                 255

Pro Ser Thr Ile Pro Val Pro Ser His Pro Ser Ser Pro Leu Pro Val
            260                 265                 270

Pro Leu Pro Ser Arg Pro Gln Asn Ser Thr Leu Arg Pro Gly Pro His
        275                 280                 285

His His His His His His
    290                 295

<210> SEQ ID NO 37
<211> LENGTH: 287
<212> TYPE: PRT
<213> ORGANISM: Artificial
<220> FEATURE:
<223> OTHER INFORMATION: Synthetic

<400> SEQUENCE: 37

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Pro Ala Ser Ala Ser
            20                  25                  30

```
Thr Gln Thr Ser Trp Thr Pro Arg Asp Leu Val Ser Gln Thr Gln
         35                  40                  45

Thr Gln Ser Cys Val Pro Pro Thr Ala Gly Ala Arg Phe Pro Thr Ile
 50                  55                  60

Pro Leu Ser Arg Leu Phe Asp Asn Ala Met Leu Arg Ala His Arg Leu
 65                  70                  75                  80

His Gln Leu Ala Phe Asp Thr Tyr Gln Glu Phe Glu Glu Ala Tyr Ile
                 85                  90                  95

Pro Lys Glu Gln Lys Tyr Ser Phe Leu Gln Asn Pro Gln Thr Ser Leu
            100                 105                 110

Cys Phe Ser Glu Ser Ile Pro Thr Pro Ser Asn Arg Glu Glu Thr Gln
        115                 120                 125

Gln Lys Ser Asn Leu Glu Leu Leu Arg Ile Ser Leu Leu Leu Ile Gln
130                 135                 140

Ser Trp Leu Glu Pro Val Gln Phe Leu Arg Ser Val Phe Ala Asn Ser
145                 150                 155                 160

Leu Val Tyr Gly Ala Ser Asp Ser Asn Val Tyr Asp Leu Leu Lys Asp
                165                 170                 175

Leu Glu Glu Gly Ile Gln Thr Leu Met Gly Arg Leu Glu Asp Gly Ser
            180                 185                 190

Pro Arg Thr Gly Gln Ile Phe Lys Gln Thr Tyr Ser Lys Phe Asp Thr
        195                 200                 205

Asn Ser His Asn Asp Asp Ala Leu Leu Lys Asn Tyr Gly Leu Leu Tyr
210                 215                 220

Cys Phe Arg Lys Asp Met Asp Lys Val Glu Thr Phe Leu Arg Ile Val
225                 230                 235                 240

Gln Cys Arg Ser Val Glu Gly Ser Cys Gly Phe Gln Ala Pro Glu Ser
                245                 250                 255

Pro Ser Thr Ile Pro Val Pro Ser His Pro Ser Ser Pro Leu Pro Val
            260                 265                 270

Pro Leu Pro Ser Arg Pro Gln Asn Ser Thr Leu Arg Pro Gly Pro
        275                 280                 285

<210> SEQ ID NO 38
<211> LENGTH: 261
<212> TYPE: PRT
<213> ORGANISM: Artificial
<220> FEATURE:
<223> OTHER INFORMATION: Synthetic

<400> SEQUENCE: 38

Ser Pro Ala Ser Ala Ser Thr Gln Thr Ser Trp Thr Pro Arg Asp Leu
1               5                   10                  15

Val Ser Ser Gln Thr Gln Thr Gln Ser Cys Val Pro Pro Thr Ala Gly
            20                  25                  30

Ala Arg Phe Pro Thr Ile Pro Leu Ser Arg Leu Phe Asp Asn Ala Met
        35                  40                  45

Leu Arg Ala His Arg Leu His Gln Leu Ala Phe Asp Thr Tyr Gln Glu
    50                  55                  60

Phe Glu Glu Ala Tyr Ile Pro Lys Glu Gln Lys Tyr Ser Phe Leu Gln
65                  70                  75                  80

Asn Pro Gln Thr Ser Leu Cys Phe Ser Glu Ser Ile Pro Thr Pro Ser
                85                  90                  95

Asn Arg Glu Glu Thr Gln Gln Lys Ser Asn Leu Glu Leu Leu Arg Ile
            100                 105                 110
```

```
Ser Leu Leu Leu Ile Gln Ser Trp Leu Glu Pro Val Gln Phe Leu Arg
            115                 120                 125

Ser Val Phe Ala Asn Ser Leu Val Tyr Gly Ala Ser Asp Ser Asn Val
        130                 135                 140

Tyr Asp Leu Leu Lys Asp Leu Glu Glu Gly Ile Gln Thr Leu Met Gly
145                 150                 155                 160

Arg Leu Glu Asp Gly Ser Pro Arg Thr Gly Gln Ile Phe Lys Gln Thr
                165                 170                 175

Tyr Ser Lys Phe Asp Thr Asn Ser His Asn Asp Ala Leu Leu Lys
            180                 185                 190

Asn Tyr Gly Leu Leu Tyr Cys Phe Arg Lys Asp Met Asp Lys Val Glu
        195                 200                 205

Thr Phe Leu Arg Ile Val Gln Cys Arg Ser Val Glu Gly Ser Cys Gly
    210                 215                 220

Phe Gln Ala Pro Glu Ser Pro Ser Thr Ile Pro Val Pro Ser His Pro
225                 230                 235                 240

Ser Ser Pro Leu Pro Val Pro Leu Pro Ser Arg Pro Gln Asn Ser Thr
                245                 250                 255

Leu Arg Pro Gly Pro
            260

<210> SEQ ID NO 39
<211> LENGTH: 295
<212> TYPE: PRT
<213> ORGANISM: Artificial
<220> FEATURE:
<223> OTHER INFORMATION: Synthetic

<400> SEQUENCE: 39

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Gln Ala Pro Glu Ser Pro
            20                  25                  30

Ser Thr Ile Pro Val Pro Ser His Pro Ser Ser Pro Leu Pro Val Pro
        35                  40                  45

Leu Pro Ser Arg Pro Gln Asn Ser Thr Leu Arg Pro Gly Pro Phe Pro
    50                  55                  60

Thr Ile Pro Leu Ser Arg Leu Phe Asp Asn Ala Met Leu Arg Ala His
65                  70                  75                  80

Arg Leu His Gln Leu Ala Phe Asp Thr Tyr Gln Glu Phe Glu Glu Ala
                85                  90                  95

Tyr Ile Pro Lys Glu Gln Lys Tyr Ser Phe Leu Gln Asn Pro Gln Thr
            100                 105                 110

Ser Leu Cys Phe Ser Glu Ser Ile Pro Thr Pro Ser Asn Arg Glu Glu
        115                 120                 125

Thr Gln Gln Lys Ser Asn Leu Glu Leu Leu Arg Ile Ser Leu Leu Leu
    130                 135                 140

Ile Gln Ser Trp Leu Glu Pro Val Gln Phe Leu Arg Ser Val Phe Ala
145                 150                 155                 160

Asn Ser Leu Val Tyr Gly Ala Ser Asp Ser Asn Val Tyr Asp Leu Leu
                165                 170                 175

Lys Asp Leu Glu Glu Gly Ile Gln Thr Leu Met Gly Arg Leu Glu Asp
            180                 185                 190

Gly Ser Pro Arg Thr Gly Gln Ile Phe Lys Gln Thr Tyr Ser Lys Phe
        195                 200                 205
```

Asp Thr Asn Ser His Asn Asp Asp Ala Leu Leu Lys Asn Tyr Gly Leu
    210                 215                 220

Leu Tyr Cys Phe Arg Lys Asp Met Asp Lys Val Glu Thr Phe Leu Arg
225                 230                 235                 240

Ile Val Gln Cys Arg Ser Val Glu Gly Ser Cys Gly Phe Ser Pro Ala
                245                 250                 255

Ser Ala Ser Thr Gln Thr Ser Trp Thr Pro Arg Asp Leu Val Ser Ser
                260                 265                 270

Gln Thr Gln Thr Gln Ser Cys Val Pro Pro Thr Ala Gly Ala Arg His
                275                 280                 285

His His His His His His
    290                 295

<210> SEQ ID NO 40
<211> LENGTH: 287
<212> TYPE: PRT
<213> ORGANISM: Artificial
<220> FEATURE:
<223> OTHER INFORMATION: Synthetic

<400> SEQUENCE: 40

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Gln Ala Pro Glu Ser Pro
                20                  25                  30

Ser Thr Ile Pro Val Pro Ser His Pro Ser Ser Pro Leu Pro Val Pro
                35                  40                  45

Leu Pro Ser Arg Pro Gln Asn Ser Thr Leu Arg Pro Gly Pro Phe Pro
    50                  55                  60

Thr Ile Pro Leu Ser Arg Leu Phe Asp Asn Ala Met Leu Arg Ala His
65                  70                  75                  80

Arg Leu His Gln Leu Ala Phe Asp Thr Tyr Gln Glu Phe Glu Glu Ala
                85                  90                  95

Tyr Ile Pro Lys Glu Gln Lys Tyr Ser Phe Leu Gln Asn Pro Gln Thr
                100                 105                 110

Ser Leu Cys Phe Ser Glu Ser Ile Pro Thr Pro Ser Asn Arg Glu Glu
            115                 120                 125

Thr Gln Gln Lys Ser Asn Leu Glu Leu Leu Arg Ile Ser Leu Leu Leu
130                 135                 140

Ile Gln Ser Trp Leu Glu Pro Val Gln Phe Leu Arg Ser Val Phe Ala
145                 150                 155                 160

Asn Ser Leu Val Tyr Gly Ala Ser Asp Ser Asn Val Tyr Asp Leu Leu
                165                 170                 175

Lys Asp Leu Glu Glu Gly Ile Gln Thr Leu Met Gly Arg Leu Glu Asp
                180                 185                 190

Gly Ser Pro Arg Thr Gly Gln Ile Phe Lys Gln Thr Tyr Ser Lys Phe
            195                 200                 205

Asp Thr Asn Ser His Asn Asp Asp Ala Leu Leu Lys Asn Tyr Gly Leu
    210                 215                 220

Leu Tyr Cys Phe Arg Lys Asp Met Asp Lys Val Glu Thr Phe Leu Arg
225                 230                 235                 240

Ile Val Gln Cys Arg Ser Val Glu Gly Ser Cys Gly Phe Ser Pro Ala
                245                 250                 255

Ser Ala Ser Thr Gln Thr Ser Trp Thr Pro Arg Asp Leu Val Ser Ser
                260                 265                 270

```
Gln Thr Gln Thr Gln Ser Cys Val Pro Pro Thr Ala Gly Ala Arg
        275                 280                 285
```

<210> SEQ ID NO 41
<211> LENGTH: 261
<212> TYPE: PRT
<213> ORGANISM: Artificial
<220> FEATURE:
<223> OTHER INFORMATION: Synthetic
<400> SEQUENCE: 41

```
Gln Ala Pro Glu Ser Pro Ser Thr Ile Pro Val Pro Ser His Pro Ser
1               5                   10                  15

Ser Pro Leu Pro Val Pro Leu Pro Ser Arg Pro Gln Asn Ser Thr Leu
            20                  25                  30

Arg Pro Gly Pro Phe Pro Thr Ile Pro Leu Ser Arg Leu Phe Asp Asn
        35                  40                  45

Ala Met Leu Arg Ala His Arg Leu His Gln Leu Ala Phe Asp Thr Tyr
    50                  55                  60

Gln Glu Phe Glu Glu Ala Tyr Ile Pro Lys Glu Gln Lys Tyr Ser Phe
65                  70                  75                  80

Leu Gln Asn Pro Gln Thr Ser Leu Cys Phe Ser Glu Ser Ile Pro Thr
                85                  90                  95

Pro Ser Asn Arg Glu Glu Thr Gln Gln Lys Ser Asn Leu Glu Leu Leu
            100                 105                 110

Arg Ile Ser Leu Leu Leu Ile Gln Ser Trp Leu Glu Pro Val Gln Phe
        115                 120                 125

Leu Arg Ser Val Phe Ala Asn Ser Leu Val Tyr Gly Ala Ser Asp Ser
    130                 135                 140

Asn Val Tyr Asp Leu Leu Lys Asp Leu Glu Glu Gly Ile Gln Thr Leu
145                 150                 155                 160

Met Gly Arg Leu Glu Asp Gly Ser Pro Arg Thr Gly Gln Ile Phe Lys
                165                 170                 175

Gln Thr Tyr Ser Lys Phe Asp Thr Asn Ser His Asn Asp Asp Ala Leu
            180                 185                 190

Leu Lys Asn Tyr Gly Leu Leu Tyr Cys Phe Arg Lys Asp Met Asp Lys
        195                 200                 205

Val Glu Thr Phe Leu Arg Ile Val Gln Cys Arg Ser Val Glu Gly Ser
    210                 215                 220

Cys Gly Phe Ser Pro Ala Ser Ala Ser Thr Gln Thr Ser Trp Thr Pro
225                 230                 235                 240

Arg Asp Leu Val Ser Ser Gln Thr Gln Thr Gln Ser Cys Val Pro Pro
                245                 250                 255

Thr Ala Gly Ala Arg
            260
```

<210> SEQ ID NO 42
<211> LENGTH: 297
<212> TYPE: PRT
<213> ORGANISM: Artificial
<220> FEATURE:
<223> OTHER INFORMATION: Synthetic
<400> SEQUENCE: 42

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Gln Ala Pro Glu Ser Pro
            20                  25                  30
```

```
Ser Thr Ile Pro Val Pro Ser His Pro Ser Ser Pro Leu Pro Val Pro
        35                  40                  45

Leu Pro Ser Arg Pro Gln Asn Ser Thr Leu Arg Pro Gly Pro Phe Pro
 50                      55                  60

Thr Ile Pro Leu Ser Arg Leu Phe Asp Asn Ala Met Leu Arg Ala His
 65                  70                  75                  80

Arg Leu His Gln Leu Ala Phe Asp Thr Tyr Gln Glu Phe Glu Glu Ala
                 85                  90                  95

Tyr Ile Pro Lys Glu Gln Lys Tyr Ser Phe Leu Gln Asn Pro Gln Thr
            100                 105                 110

Ser Leu Cys Phe Ser Glu Ser Ile Pro Thr Pro Ser Asn Arg Glu Glu
            115                 120                 125

Thr Gln Gln Lys Ser Asn Leu Glu Leu Leu Arg Ile Ser Leu Leu Leu
        130                 135                 140

Ile Gln Ser Trp Leu Glu Pro Val Gln Phe Leu Arg Ser Val Phe Ala
145                 150                 155                 160

Asn Ser Leu Val Tyr Gly Ala Ser Asp Ser Asn Val Tyr Asp Leu Leu
                165                 170                 175

Lys Asp Leu Glu Glu Gly Ile Gln Thr Leu Met Gly Arg Leu Glu Asp
            180                 185                 190

Gly Ser Pro Arg Thr Gly Gln Ile Phe Lys Gln Thr Tyr Ser Lys Phe
        195                 200                 205

Asp Thr Asn Ser His Asn Asp Asp Ala Leu Leu Lys Asn Tyr Gly Leu
210                 215                 220

Leu Tyr Cys Phe Arg Lys Asp Met Asp Lys Val Glu Thr Phe Leu Arg
225                 230                 235                 240

Ile Val Gln Cys Arg Ser Val Glu Gly Ser Cys Gly Phe Gln Ala Pro
                245                 250                 255

Glu Ser Pro Ser Thr Ile Pro Val Pro Ser His Pro Ser Ser Pro Leu
            260                 265                 270

Pro Val Pro Leu Pro Ser Arg Pro Gln Asn Ser Thr Leu Arg Pro Gly
        275                 280                 285

Pro His His His His His His His
    290                 295
```

<210> SEQ ID NO 43
<211> LENGTH: 289
<212> TYPE: PRT
<213> ORGANISM: Artificial
<220> FEATURE:
<223> OTHER INFORMATION: Synthetic

<400> SEQUENCE: 43

```
Met Ala Thr Gly Ser Arg Thr Ser Leu Leu Leu Ala Phe Gly Leu Leu
 1               5                  10                  15

Cys Leu Pro Trp Leu Gln Glu Gly Ser Ala Gln Ala Pro Glu Ser Pro
                 20                  25                  30

Ser Thr Ile Pro Val Pro Ser His Pro Ser Ser Pro Leu Pro Val Pro
         35                  40                  45

Leu Pro Ser Arg Pro Gln Asn Ser Thr Leu Arg Pro Gly Pro Phe Pro
 50                      55                  60

Thr Ile Pro Leu Ser Arg Leu Phe Asp Asn Ala Met Leu Arg Ala His
 65                  70                  75                  80

Arg Leu His Gln Leu Ala Phe Asp Thr Tyr Gln Glu Phe Glu Glu Ala
                 85                  90                  95
```

-continued

```
Tyr Ile Pro Lys Glu Gln Lys Tyr Ser Phe Leu Gln Asn Pro Gln Thr
            100                 105                 110

Ser Leu Cys Phe Ser Glu Ser Ile Pro Thr Pro Ser Asn Arg Glu Glu
        115                 120                 125

Thr Gln Gln Lys Ser Asn Leu Glu Leu Leu Arg Ile Ser Leu Leu Leu
    130                 135                 140

Ile Gln Ser Trp Leu Glu Pro Val Gln Phe Leu Arg Ser Val Phe Ala
145                 150                 155                 160

Asn Ser Leu Val Tyr Gly Ala Ser Asp Ser Asn Val Tyr Asp Leu Leu
                165                 170                 175

Lys Asp Leu Glu Glu Gly Ile Gln Thr Leu Met Gly Arg Leu Glu Asp
            180                 185                 190

Gly Ser Pro Arg Thr Gly Gln Ile Phe Lys Gln Thr Tyr Ser Lys Phe
        195                 200                 205

Asp Thr Asn Ser His Asn Asp Asp Ala Leu Leu Lys Asn Tyr Gly Leu
    210                 215                 220

Leu Tyr Cys Phe Arg Lys Asp Met Asp Lys Val Glu Thr Phe Leu Arg
225                 230                 235                 240

Ile Val Gln Cys Arg Ser Val Glu Gly Ser Cys Gly Phe Gln Ala Pro
                245                 250                 255

Glu Ser Pro Ser Thr Ile Pro Val Pro Ser His Pro Ser Ser Pro Leu
            260                 265                 270

Pro Val Pro Leu Pro Ser Arg Pro Gln Asn Ser Thr Leu Arg Pro Gly
        275                 280                 285

Pro

<210> SEQ ID NO 44
<211> LENGTH: 263
<212> TYPE: PRT
<213> ORGANISM: Artificial
<220> FEATURE:
<223> OTHER INFORMATION: Synthetic

<400> SEQUENCE: 44

Gln Ala Pro Glu Ser Pro Ser Thr Ile Pro Val Pro Ser His Pro Ser
1               5                   10                  15

Ser Pro Leu Pro Val Pro Leu Pro Ser Arg Pro Gln Asn Ser Thr Leu
            20                  25                  30

Arg Pro Gly Pro Phe Pro Thr Ile Pro Leu Ser Arg Leu Phe Asp Asn
        35                  40                  45

Ala Met Leu Arg Ala His Arg Leu His Gln Leu Ala Phe Asp Thr Tyr
    50                  55                  60

Gln Glu Phe Glu Glu Ala Tyr Ile Pro Lys Glu Gln Lys Tyr Ser Phe
65                  70                  75                  80

Leu Gln Asn Pro Gln Thr Ser Leu Cys Phe Ser Glu Ser Ile Pro Thr
                85                  90                  95

Pro Ser Asn Arg Glu Glu Thr Gln Gln Lys Ser Asn Leu Glu Leu Leu
            100                 105                 110

Arg Ile Ser Leu Leu Leu Ile Gln Ser Trp Leu Glu Pro Val Gln Phe
        115                 120                 125

Leu Arg Ser Val Phe Ala Asn Ser Leu Val Tyr Gly Ala Ser Asp Ser
    130                 135                 140

Asn Val Tyr Asp Leu Leu Lys Asp Leu Glu Glu Gly Ile Gln Thr Leu
145                 150                 155                 160
```

```
Met Gly Arg Leu Glu Asp Gly Ser Pro Arg Thr Gly Gln Ile Phe Lys
                165                 170                 175

Gln Thr Tyr Ser Lys Phe Asp Thr Asn Ser His Asn Asp Asp Ala Leu
            180                 185                 190

Leu Lys Asn Tyr Gly Leu Leu Tyr Cys Phe Arg Lys Asp Met Asp Lys
            195                 200                 205

Val Glu Thr Phe Leu Arg Ile Val Gln Cys Arg Ser Val Glu Gly Ser
        210                 215                 220

Cys Gly Phe Gln Ala Pro Glu Ser Pro Ser Thr Ile Pro Val Pro Ser
225                 230                 235                 240

His Pro Ser Ser Pro Leu Pro Val Pro Leu Pro Ser Arg Pro Gln Asn
                245                 250                 255

Ser Thr Leu Arg Pro Gly Pro
                260

<210> SEQ ID NO 45
<211> LENGTH: 333
<212> TYPE: PRT
<213> ORGANISM: Artificial
<220> FEATURE:
<223> OTHER INFORMATION: Synthetic

<400> SEQUENCE: 45

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Gln Ala Pro Glu Ser Pro
                20                  25                  30

Ser Thr Ile Pro Val Pro Ser His Pro Ser Ser Pro Leu Pro Val Pro
            35                  40                  45

Leu Pro Ser Arg Pro Gln Asn Ser Thr Leu Arg Pro Gly Pro Phe Pro
        50                  55                  60

Thr Ile Pro Leu Ser Arg Leu Phe Asp Asn Ala Met Leu Arg Ala His
65                  70                  75                  80

Arg Leu His Gln Leu Ala Phe Asp Thr Tyr Gln Glu Phe Glu Glu Ala
                85                  90                  95

Tyr Ile Pro Lys Glu Gln Lys Tyr Ser Phe Leu Gln Asn Pro Gln Thr
                100                 105                 110

Ser Leu Cys Phe Ser Glu Ser Ile Pro Thr Pro Ser Asn Arg Glu Glu
            115                 120                 125

Thr Gln Gln Lys Ser Asn Leu Glu Leu Leu Arg Ile Ser Leu Leu Leu
130                 135                 140

Ile Gln Ser Trp Leu Glu Pro Val Gln Phe Leu Arg Ser Val Phe Ala
145                 150                 155                 160

Asn Ser Leu Val Tyr Gly Ala Ser Asp Ser Asn Val Tyr Asp Leu Leu
                165                 170                 175

Lys Asp Leu Glu Glu Gly Ile Gln Thr Leu Met Gly Arg Leu Glu Asp
            180                 185                 190

Gly Ser Pro Arg Thr Gly Gln Ile Phe Lys Gln Thr Tyr Ser Lys Phe
        195                 200                 205

Asp Thr Asn Ser His Asn Asp Asp Ala Leu Leu Lys Asn Tyr Gly Leu
    210                 215                 220

Leu Tyr Cys Phe Arg Lys Asp Met Asp Lys Val Glu Thr Phe Leu Arg
225                 230                 235                 240

Ile Val Gln Cys Arg Ser Val Glu Gly Ser Cys Gly Phe Gln Ala Pro
                245                 250                 255
```

```
Glu Ser Pro Ser Thr Ile Pro Val Pro Ser His Pro Ser Ser Pro Leu
                260                 265                 270

Pro Val Pro Leu Pro Ser Arg Pro Gln Asn Ser Thr Leu Arg Pro Gly
            275                 280                 285

Pro Gln Ala Pro Glu Ser Pro Ser Thr Ile Pro Val Pro Ser His Pro
        290                 295                 300

Ser Ser Pro Leu Pro Val Pro Leu Pro Ser Arg Pro Gln Asn Ser Thr
305                 310                 315                 320

Leu Arg Pro Gly Pro His His His His His His His
                325                 330

<210> SEQ ID NO 46
<211> LENGTH: 325
<212> TYPE: PRT
<213> ORGANISM: Artificial
<220> FEATURE:
<223> OTHER INFORMATION: Synthetic

<400> SEQUENCE: 46

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Gln Ala Pro Glu Ser Pro
            20                  25                  30

Ser Thr Ile Pro Val Pro Ser His Pro Ser Ser Pro Leu Pro Val Pro
        35                  40                  45

Leu Pro Ser Arg Pro Gln Asn Ser Thr Leu Arg Pro Gly Pro Phe Pro
    50                  55                  60

Thr Ile Pro Leu Ser Arg Leu Phe Asp Asn Ala Met Leu Arg Ala His
65                  70                  75                  80

Arg Leu His Gln Leu Ala Phe Asp Thr Tyr Gln Glu Phe Glu Glu Ala
                85                  90                  95

Tyr Ile Pro Lys Glu Gln Lys Tyr Ser Phe Leu Gln Asn Pro Gln Thr
            100                 105                 110

Ser Leu Cys Phe Ser Glu Ser Ile Pro Thr Pro Ser Asn Arg Glu Glu
        115                 120                 125

Thr Gln Gln Lys Ser Asn Leu Glu Leu Leu Arg Ile Ser Leu Leu Leu
    130                 135                 140

Ile Gln Ser Trp Leu Glu Pro Val Gln Phe Leu Arg Ser Val Phe Ala
145                 150                 155                 160

Asn Ser Leu Val Tyr Gly Ala Ser Asp Ser Asn Val Tyr Asp Leu Leu
                165                 170                 175

Lys Asp Leu Glu Glu Gly Ile Gln Thr Leu Met Gly Arg Leu Glu Asp
            180                 185                 190

Gly Ser Pro Arg Thr Gly Gln Ile Phe Lys Gln Thr Tyr Ser Lys Phe
        195                 200                 205

Asp Thr Asn Ser His Asn Asp Asp Ala Leu Leu Lys Asn Tyr Gly Leu
    210                 215                 220

Leu Tyr Cys Phe Arg Lys Asp Met Asp Lys Val Glu Thr Phe Leu Arg
225                 230                 235                 240

Ile Val Gln Cys Arg Ser Val Glu Gly Ser Cys Gly Phe Gln Ala Pro
                245                 250                 255

Glu Ser Pro Ser Thr Ile Pro Val Pro Ser His Pro Ser Ser Pro Leu
            260                 265                 270

Pro Val Pro Leu Pro Ser Arg Pro Gln Asn Ser Thr Leu Arg Pro Gly
        275                 280                 285
```

```
Pro Gln Ala Pro Glu Ser Pro Ser Thr Ile Pro Val Pro Ser His Pro
    290                 295                 300

Ser Ser Pro Leu Pro Val Pro Leu Pro Ser Arg Pro Gln Asn Ser Thr
305                 310                 315                 320

Leu Arg Pro Gly Pro
                325

<210> SEQ ID NO 47
<211> LENGTH: 299
<212> TYPE: PRT
<213> ORGANISM: Artificial
<220> FEATURE:
<223> OTHER INFORMATION: Synthetic

<400> SEQUENCE: 47

Gln Ala Pro Glu Ser Pro Ser Thr Ile Pro Val Pro Ser His Pro Ser
1               5                   10                  15

Ser Pro Leu Pro Val Pro Leu Pro Ser Arg Pro Gln Asn Ser Thr Leu
            20                  25                  30

Arg Pro Gly Pro Phe Pro Thr Ile Pro Leu Ser Arg Leu Phe Asp Asn
        35                  40                  45

Ala Met Leu Arg Ala His Arg Leu His Gln Leu Ala Phe Asp Thr Tyr
50                  55                  60

Gln Glu Phe Glu Glu Ala Tyr Ile Pro Lys Glu Gln Lys Tyr Ser Phe
65                  70                  75                  80

Leu Gln Asn Pro Gln Thr Ser Leu Cys Phe Ser Glu Ser Ile Pro Thr
                85                  90                  95

Pro Ser Asn Arg Glu Glu Thr Gln Gln Lys Ser Asn Leu Glu Leu Leu
            100                 105                 110

Arg Ile Ser Leu Leu Leu Ile Gln Ser Trp Leu Glu Pro Val Gln Phe
        115                 120                 125

Leu Arg Ser Val Phe Ala Asn Ser Leu Val Tyr Gly Ala Ser Asp Ser
130                 135                 140

Asn Val Tyr Asp Leu Leu Lys Asp Leu Glu Glu Gly Ile Gln Thr Leu
145                 150                 155                 160

Met Gly Arg Leu Glu Asp Gly Ser Pro Arg Thr Gly Gln Ile Phe Lys
                165                 170                 175

Gln Thr Tyr Ser Lys Phe Asp Thr Asn Ser His Asn Asp Asp Ala Leu
            180                 185                 190

Leu Lys Asn Tyr Gly Leu Leu Tyr Cys Phe Arg Lys Asp Met Asp Lys
        195                 200                 205

Val Glu Thr Phe Leu Arg Ile Val Gln Cys Arg Ser Val Glu Gly Ser
210                 215                 220

Cys Gly Phe Gln Ala Pro Glu Ser Pro Ser Thr Ile Pro Val Pro Ser
225                 230                 235                 240

His Pro Ser Ser Pro Leu Pro Val Pro Leu Pro Ser Arg Pro Gln Asn
                245                 250                 255

Ser Thr Leu Arg Pro Gly Pro Gln Ala Pro Glu Ser Pro Ser Thr Ile
            260                 265                 270

Pro Val Pro Ser His Pro Ser Ser Pro Leu Pro Val Pro Leu Pro Ser
        275                 280                 285

Arg Pro Gln Asn Ser Thr Leu Arg Pro Gly Pro
290                 295

<210> SEQ ID NO 48
<211> LENGTH: 331
```

```
<212> TYPE: PRT
<213> ORGANISM: Artificial
<220> FEATURE:
<223> OTHER INFORMATION: Synthetic

<400> SEQUENCE: 48

Met Ala Thr Gly Ser Arg Thr Ser Leu Leu Ala Phe Gly Leu Leu
1               5                   10                  15

Cys Leu Pro Trp Leu Gln Glu Gly Ser Ala Ser Pro Ala Ser Ala Ser
            20                  25                  30

Thr Gln Thr Ser Trp Thr Pro Arg Asp Leu Val Ser Ser Gln Thr Gln
            35                  40                  45

Thr Gln Ser Cys Val Pro Pro Thr Ala Gly Ala Arg Phe Pro Thr Ile
    50                  55                  60

Pro Leu Ser Arg Leu Phe Asp Asn Ala Met Leu Arg Ala His Arg Leu
65                  70                  75                  80

His Gln Leu Ala Phe Asp Thr Tyr Gln Glu Phe Glu Glu Ala Tyr Ile
                85                  90                  95

Pro Lys Glu Gln Lys Tyr Ser Phe Leu Gln Asn Pro Gln Thr Ser Leu
            100                 105                 110

Cys Phe Ser Glu Ser Ile Pro Thr Pro Ser Asn Arg Glu Glu Thr Gln
        115                 120                 125

Gln Lys Ser Asn Leu Glu Leu Leu Arg Ile Ser Leu Leu Leu Ile Gln
130                 135                 140

Ser Trp Leu Glu Pro Val Gln Phe Leu Arg Ser Val Phe Ala Asn Ser
145                 150                 155                 160

Leu Val Tyr Gly Ala Ser Asp Ser Asn Val Tyr Asp Leu Leu Lys Asp
                165                 170                 175

Leu Glu Glu Gly Ile Gln Thr Leu Met Gly Arg Leu Glu Asp Gly Ser
            180                 185                 190

Pro Arg Thr Gly Gln Ile Phe Lys Gln Thr Tyr Ser Lys Phe Asp Thr
        195                 200                 205

Asn Ser His Asn Asp Asp Ala Leu Leu Lys Asn Tyr Gly Leu Leu Tyr
210                 215                 220

Cys Phe Arg Lys Asp Met Asp Lys Val Glu Thr Phe Leu Arg Ile Val
225                 230                 235                 240

Gln Cys Arg Ser Val Glu Gly Ser Cys Gly Phe Gln Ala Pro Glu Ser
                245                 250                 255

Pro Ser Thr Ile Pro Val Pro Ser His Pro Ser Ser Pro Leu Pro Val
            260                 265                 270

Pro Leu Pro Ser Arg Pro Gln Asn Ser Thr Leu Arg Pro Gly Pro Gln
        275                 280                 285

Ala Pro Glu Ser Pro Ser Thr Ile Pro Val Pro Ser His Pro Ser Ser
290                 295                 300

Pro Leu Pro Val Pro Leu Pro Ser Arg Pro Gln Asn Ser Thr Leu Arg
305                 310                 315                 320

Pro Gly Pro His His His His His His His
                325                 330

<210> SEQ ID NO 49
<211> LENGTH: 323
<212> TYPE: PRT
<213> ORGANISM: Artificial
<220> FEATURE:
<223> OTHER INFORMATION: Synthetic

<400> SEQUENCE: 49
```

Met Ala Thr Gly Ser Arg Thr Ser Leu Leu Ala Phe Gly Leu Leu
1               5                   10                  15

Cys Leu Pro Trp Leu Gln Glu Gly Ser Ala Ser Pro Ala Ser Ala Ser
                20                  25                  30

Thr Gln Thr Ser Trp Thr Pro Arg Asp Leu Val Ser Gln Thr Gln
            35                  40                  45

Thr Gln Ser Cys Val Pro Pro Thr Ala Gly Ala Arg Phe Pro Thr Ile
        50                  55                  60

Pro Leu Ser Arg Leu Phe Asp Asn Ala Met Leu Arg Ala His Arg Leu
65                  70                  75                  80

His Gln Leu Ala Phe Asp Thr Tyr Gln Glu Phe Glu Glu Ala Tyr Ile
                85                  90                  95

Pro Lys Glu Gln Lys Tyr Ser Phe Leu Gln Asn Pro Gln Thr Ser Leu
                100                 105                 110

Cys Phe Ser Glu Ser Ile Pro Thr Pro Ser Asn Arg Glu Glu Thr Gln
            115                 120                 125

Gln Lys Ser Asn Leu Glu Leu Leu Arg Ile Ser Leu Leu Leu Ile Gln
        130                 135                 140

Ser Trp Leu Glu Pro Val Gln Phe Leu Arg Ser Val Phe Ala Asn Ser
145                 150                 155                 160

Leu Val Tyr Gly Ala Ser Asp Ser Asn Val Tyr Asp Leu Leu Lys Asp
                165                 170                 175

Leu Glu Glu Gly Ile Gln Thr Leu Met Gly Arg Leu Glu Asp Gly Ser
                180                 185                 190

Pro Arg Thr Gly Gln Ile Phe Lys Gln Thr Tyr Ser Lys Phe Asp Thr
            195                 200                 205

Asn Ser His Asn Asp Asp Ala Leu Leu Lys Asn Tyr Gly Leu Leu Tyr
        210                 215                 220

Cys Phe Arg Lys Asp Met Asp Lys Val Glu Thr Phe Leu Arg Ile Val
225                 230                 235                 240

Gln Cys Arg Ser Val Glu Gly Ser Cys Gly Phe Gln Ala Pro Glu Ser
                245                 250                 255

Pro Ser Thr Ile Pro Val Pro Ser His Pro Ser Ser Pro Leu Pro Val
                260                 265                 270

Pro Leu Pro Ser Arg Pro Gln Asn Ser Thr Leu Arg Pro Gly Pro Gln
            275                 280                 285

Ala Pro Glu Ser Pro Ser Thr Ile Pro Val Pro Ser His Pro Ser Ser
        290                 295                 300

Pro Leu Pro Val Pro Leu Pro Ser Arg Pro Gln Asn Ser Thr Leu Arg
305                 310                 315                 320

Pro Gly Pro

<210> SEQ ID NO 50
<211> LENGTH: 297
<212> TYPE: PRT
<213> ORGANISM: Artificial
<220> FEATURE:
<223> OTHER INFORMATION: Synthetic

<400> SEQUENCE: 50

Ser Pro Ala Ser Ala Ser Thr Gln Thr Ser Trp Thr Pro Arg Asp Leu
1               5                   10                  15

Val Ser Ser Gln Thr Gln Thr Gln Ser Cys Val Pro Thr Ala Gly
                20                  25                  30

```
Ala Arg Phe Pro Thr Ile Pro Leu Ser Arg Leu Phe Asp Asn Ala Met
         35                  40                  45

Leu Arg Ala His Arg Leu His Gln Leu Ala Phe Asp Thr Tyr Gln Glu
 50                  55                  60

Phe Glu Glu Ala Tyr Ile Pro Lys Glu Gln Lys Tyr Ser Phe Leu Gln
65                  70                  75                  80

Asn Pro Gln Thr Ser Leu Cys Phe Ser Glu Ser Ile Pro Thr Pro Ser
                 85                  90                  95

Asn Arg Glu Glu Thr Gln Gln Lys Ser Asn Leu Glu Leu Leu Arg Ile
            100                 105                 110

Ser Leu Leu Leu Ile Gln Ser Trp Leu Glu Pro Val Gln Phe Leu Arg
        115                 120                 125

Ser Val Phe Ala Asn Ser Leu Val Tyr Gly Ala Ser Asp Ser Asn Val
    130                 135                 140

Tyr Asp Leu Leu Lys Asp Leu Glu Glu Gly Ile Gln Thr Leu Met Gly
145                 150                 155                 160

Arg Leu Glu Asp Gly Ser Pro Arg Thr Gly Gln Ile Phe Lys Gln Thr
                165                 170                 175

Tyr Ser Lys Phe Asp Thr Asn Ser His Asn Asp Asp Ala Leu Leu Lys
            180                 185                 190

Asn Tyr Gly Leu Leu Tyr Cys Phe Arg Lys Asp Met Asp Lys Val Glu
        195                 200                 205

Thr Phe Leu Arg Ile Val Gln Cys Arg Ser Val Glu Gly Ser Cys Gly
    210                 215                 220

Phe Gln Ala Pro Glu Ser Pro Ser Thr Ile Pro Val Pro Ser His Pro
225                 230                 235                 240

Ser Ser Pro Leu Pro Val Pro Leu Pro Ser Arg Pro Gln Asn Ser Thr
                245                 250                 255

Leu Arg Pro Gly Pro Gln Ala Pro Glu Ser Pro Ser Thr Ile Pro Val
            260                 265                 270

Pro Ser His Pro Ser Ser Pro Leu Pro Val Pro Leu Pro Ser Arg Pro
        275                 280                 285

Gln Asn Ser Thr Leu Arg Pro Gly Pro
    290                 295

<210> SEQ ID NO 51
<211> LENGTH: 327
<212> TYPE: PRT
<213> ORGANISM: Artificial
<220> FEATURE:
<223> OTHER INFORMATION: Synthetic

<400> SEQUENCE: 51

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Pro Ala Ser Ala Ser
                20                  25                  30

Thr Gln Thr Ser Trp Thr Pro Arg Asp Leu Val Ser Ser Gln Thr Gln
            35                  40                  45

Thr Gln Ser Cys Val Pro Pro Thr Ala Gly Ala Arg Phe Pro Thr Ile
    50                  55                  60

Pro Leu Ser Arg Leu Phe Asp Asn Ala Met Leu Arg Ala His Arg Leu
65                  70                  75                  80

His Gln Leu Ala Phe Asp Thr Tyr Gln Glu Phe Glu Glu Ala Tyr Ile
                85                  90                  95
```

```
Pro Lys Glu Gln Lys Tyr Ser Phe Leu Gln Asn Pro Gln Thr Ser Leu
            100                 105                 110

Cys Phe Ser Glu Ser Ile Pro Thr Pro Ser Asn Arg Glu Glu Thr Gln
        115                 120                 125

Gln Lys Ser Asn Leu Glu Leu Leu Arg Ile Ser Leu Leu Leu Ile Gln
    130                 135                 140

Ser Trp Leu Glu Pro Val Gln Phe Leu Arg Ser Val Phe Ala Asn Ser
145                 150                 155                 160

Leu Val Tyr Gly Ala Ser Asp Ser Asn Val Tyr Asp Leu Leu Lys Asp
                165                 170                 175

Leu Glu Glu Gly Ile Gln Thr Leu Met Gly Arg Leu Glu Asp Gly Ser
            180                 185                 190

Pro Arg Thr Gly Gln Ile Phe Lys Gln Thr Tyr Ser Lys Phe Asp Thr
        195                 200                 205

Asn Ser His Asn Asp Asp Ala Leu Leu Lys Asn Tyr Gly Leu Leu Tyr
    210                 215                 220

Cys Phe Arg Lys Asp Met Asp Lys Val Glu Thr Phe Leu Arg Ile Val
225                 230                 235                 240

Gln Cys Arg Ser Val Glu Gly Ser Cys Gly Phe Ser Pro Ala Ser Ala
                245                 250                 255

Ser Thr Gln Thr Ser Trp Thr Pro Arg Asp Leu Val Ser Ser Gln Thr
            260                 265                 270

Gln Thr Gln Ser Cys Val Pro Pro Thr Ala Gly Ala Arg Ser Pro Ala
        275                 280                 285

Ser Ala Ser Thr Gln Thr Ser Trp Thr Pro Arg Asp Leu Val Ser Ser
    290                 295                 300

Gln Thr Gln Thr Gln Ser Cys Val Pro Pro Thr Ala Gly Ala Arg His
305                 310                 315                 320

His His His His His His
            325

<210> SEQ ID NO 52
<211> LENGTH: 293
<212> TYPE: PRT
<213> ORGANISM: Artificial
<220> FEATURE:
<223> OTHER INFORMATION: Synthetic

<400> SEQUENCE: 52

Ser Pro Ala Ser Ala Ser Thr Gln Thr Ser Trp Thr Pro Arg Asp Leu
1               5                   10                  15

Val Ser Ser Gln Thr Gln Thr Gln Ser Cys Val Pro Pro Thr Ala Gly
                20                  25                  30

Ala Arg Phe Pro Thr Ile Pro Leu Ser Arg Leu Phe Asp Asn Ala Met
            35                  40                  45

Leu Arg Ala His Arg Leu His Gln Leu Ala Phe Asp Thr Tyr Gln Glu
    50                  55                  60

Phe Glu Glu Ala Tyr Ile Pro Lys Glu Gln Lys Tyr Ser Phe Leu Gln
65                  70                  75                  80

Asn Pro Gln Thr Ser Leu Cys Phe Ser Glu Ser Ile Pro Thr Pro Ser
                85                  90                  95

Asn Arg Glu Glu Thr Gln Gln Lys Ser Asn Leu Glu Leu Leu Arg Ile
            100                 105                 110

Ser Leu Leu Leu Ile Gln Ser Trp Leu Glu Pro Val Gln Phe Leu Arg
        115                 120                 125
```

Ser Val Phe Ala Asn Ser Leu Val Tyr Gly Ala Ser Asp Ser Asn Val
130                 135                 140

Tyr Asp Leu Leu Lys Asp Leu Glu Glu Gly Ile Gln Thr Leu Met Gly
145                 150                 155                 160

Arg Leu Glu Asp Gly Ser Pro Arg Thr Gly Gln Ile Phe Lys Gln Thr
                165                 170                 175

Tyr Ser Lys Phe Asp Thr Asn Ser His Asn Asp Asp Ala Leu Leu Lys
                180                 185                 190

Asn Tyr Gly Leu Leu Tyr Cys Phe Arg Lys Asp Met Asp Lys Val Glu
            195                 200                 205

Thr Phe Leu Arg Ile Val Gln Cys Arg Ser Val Glu Gly Ser Cys Gly
210                 215                 220

Phe Ser Pro Ala Ser Ala Ser Thr Gln Thr Ser Trp Thr Pro Arg Asp
225                 230                 235                 240

Leu Val Ser Ser Gln Thr Gln Thr Gln Ser Cys Val Pro Pro Thr Ala
                245                 250                 255

Gly Ala Arg Ser Pro Ala Ser Ala Ser Thr Gln Thr Ser Trp Thr Pro
                260                 265                 270

Arg Asp Leu Val Ser Ser Gln Thr Gln Thr Gln Ser Cys Val Pro Pro
                275                 280                 285

Thr Ala Gly Ala Arg
                290

<210> SEQ ID NO 53
<211> LENGTH: 327
<212> TYPE: PRT
<213> ORGANISM: Artificial
<220> FEATURE:
<223> OTHER INFORMATION: Synthetic

<400> SEQUENCE: 53

Ser Pro Ala Ser Ala Ser Thr Gln Thr Ser Trp Thr Pro Arg Asp Leu
1               5                   10                  15

Val Ser Ser Gln Thr Gln Thr Gln Ser Cys Val Pro Pro Thr Ala Gly
                20                  25                  30

Ala Arg Ser Pro Ala Ser Ala Ser Thr Gln Thr Ser Trp Thr Pro Arg
            35                  40                  45

Asp Leu Val Ser Ser Gln Thr Gln Thr Gln Ser Cys Val Pro Pro Thr
    50                  55                  60

Ala Gly Ala Arg Phe Pro Thr Ile Pro Leu Ser Arg Leu Phe Asp Asn
65                  70                  75                  80

Ala Met Leu Arg Ala His Arg Leu His Gln Leu Ala Phe Asp Thr Tyr
                85                  90                  95

Gln Glu Phe Glu Glu Ala Tyr Ile Pro Lys Glu Gln Lys Tyr Ser Phe
            100                 105                 110

Leu Gln Asn Pro Gln Thr Ser Leu Cys Phe Ser Glu Ser Ile Pro Thr
        115                 120                 125

Pro Ser Asn Arg Glu Glu Thr Gln Gln Lys Ser Asn Leu Glu Leu Leu
    130                 135                 140

Arg Ile Ser Leu Leu Leu Ile Gln Ser Trp Leu Glu Pro Val Gln Phe
145                 150                 155                 160

Leu Arg Ser Val Phe Ala Asn Ser Leu Val Tyr Gly Ala Ser Asp Ser
                165                 170                 175

Asn Val Tyr Asp Leu Leu Lys Asp Leu Glu Glu Gly Ile Gln Thr Leu
            180                 185                 190

```
Met Gly Arg Leu Glu Asp Gly Ser Pro Arg Thr Gly Gln Ile Phe Lys
            195                 200                 205

Gln Thr Tyr Ser Lys Phe Asp Thr Asn Ser His Asn Asp Asp Ala Leu
    210                 215                 220

Leu Lys Asn Tyr Gly Leu Leu Tyr Cys Phe Arg Lys Asp Met Asp Lys
225                 230                 235                 240

Val Glu Thr Phe Leu Arg Ile Val Gln Cys Arg Ser Val Glu Gly Ser
                245                 250                 255

Cys Gly Phe Ser Pro Ala Ser Ala Ser Thr Gln Thr Ser Trp Thr Pro
            260                 265                 270

Arg Asp Leu Val Ser Ser Gln Thr Gln Thr Gln Ser Cys Val Pro Pro
        275                 280                 285

Thr Ala Gly Ala Arg Ser Pro Ala Ser Ala Ser Thr Gln Thr Ser Trp
    290                 295                 300

Thr Pro Arg Asp Leu Val Ser Ser Gln Thr Gln Thr Gln Ser Cys Val
305                 310                 315                 320

Pro Pro Thr Ala Gly Ala Arg
                325

<210> SEQ ID NO 54
<211> LENGTH: 329
<212> TYPE: PRT
<213> ORGANISM: Artificial
<220> FEATURE:
<223> OTHER INFORMATION: Synthetic

<400> SEQUENCE: 54

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Gln Ala Pro Glu Ser Pro
            20                  25                  30

Ser Thr Ile Pro Val Pro Ser His Pro Ser Ser Pro Leu Pro Val Pro
        35                  40                  45

Leu Pro Ser Arg Pro Gln Asn Ser Thr Leu Arg Pro Gly Pro Phe Pro
    50                  55                  60

Thr Ile Pro Leu Ser Arg Leu Phe Asp Asn Ala Met Leu Arg Ala His
65                  70                  75                  80

Arg Leu His Gln Leu Ala Phe Asp Thr Tyr Gln Glu Phe Glu Glu Ala
                85                  90                  95

Tyr Ile Pro Lys Glu Gln Lys Tyr Ser Phe Leu Gln Asn Pro Gln Thr
            100                 105                 110

Ser Leu Cys Phe Ser Glu Ser Ile Pro Thr Pro Ser Asn Arg Glu Glu
        115                 120                 125

Thr Gln Gln Lys Ser Asn Leu Glu Leu Leu Arg Ile Ser Leu Leu Leu
    130                 135                 140

Ile Gln Ser Trp Leu Glu Pro Val Gln Phe Leu Arg Ser Val Phe Ala
145                 150                 155                 160

Asn Ser Leu Val Tyr Gly Ala Ser Asp Ser Asn Val Tyr Asp Leu Leu
                165                 170                 175

Lys Asp Leu Glu Glu Gly Ile Gln Thr Leu Met Gly Arg Leu Glu Asp
            180                 185                 190

Gly Ser Pro Arg Thr Gly Gln Ile Phe Lys Gln Thr Tyr Ser Lys Phe
        195                 200                 205

Asp Thr Asn Ser His Asn Asp Asp Ala Leu Leu Lys Asn Tyr Gly Leu
    210                 215                 220
```

```
Leu Tyr Cys Phe Arg Lys Asp Met Asp Lys Val Glu Thr Phe Leu Arg
225                 230                 235                 240

Ile Val Gln Cys Arg Ser Val Glu Gly Ser Cys Gly Phe Ser Pro Ala
            245                 250                 255

Ser Ala Ser Thr Gln Thr Ser Trp Thr Pro Arg Asp Leu Val Ser Ser
            260                 265                 270

Gln Thr Gln Thr Gln Ser Cys Val Pro Pro Thr Ala Gly Ala Arg Ser
            275                 280                 285

Pro Ala Ser Ala Ser Thr Gln Thr Ser Trp Thr Pro Arg Asp Leu Val
            290                 295                 300

Ser Ser Gln Thr Gln Thr Gln Ser Cys Val Pro Pro Thr Ala Gly Ala
305                 310                 315                 320

Arg His His His His His His His
                325

<210> SEQ ID NO 55
<211> LENGTH: 321
<212> TYPE: PRT
<213> ORGANISM: Artificial
<220> FEATURE:
<223> OTHER INFORMATION: Synthetic

<400> SEQUENCE: 55

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Gln Ala Pro Glu Ser Pro
            20                  25                  30

Ser Thr Ile Pro Val Pro Ser His Pro Ser Ser Pro Leu Pro Val Pro
            35                  40                  45

Leu Pro Ser Arg Pro Gln Asn Ser Thr Leu Arg Pro Gly Pro Phe Pro
50                  55                  60

Thr Ile Pro Leu Ser Arg Leu Phe Asp Asn Ala Met Leu Arg Ala His
65                  70                  75                  80

Arg Leu His Gln Leu Ala Phe Asp Thr Tyr Gln Glu Phe Glu Glu Ala
                85                  90                  95

Tyr Ile Pro Lys Glu Gln Lys Tyr Ser Phe Leu Gln Asn Pro Gln Thr
            100                 105                 110

Ser Leu Cys Phe Ser Glu Ser Ile Pro Thr Pro Ser Asn Arg Glu Glu
            115                 120                 125

Thr Gln Gln Lys Ser Asn Leu Glu Leu Leu Arg Ile Ser Leu Leu Leu
130                 135                 140

Ile Gln Ser Trp Leu Glu Pro Val Gln Phe Leu Arg Ser Val Phe Ala
145                 150                 155                 160

Asn Ser Leu Val Tyr Gly Ala Ser Asp Ser Asn Val Tyr Asp Leu Leu
                165                 170                 175

Lys Asp Leu Glu Glu Gly Ile Gln Thr Leu Met Gly Arg Leu Glu Asp
            180                 185                 190

Gly Ser Pro Arg Thr Gly Gln Ile Phe Lys Gln Thr Tyr Ser Lys Phe
            195                 200                 205

Asp Thr Asn Ser His Asn Asp Asp Ala Leu Leu Lys Asn Tyr Gly Leu
210                 215                 220

Leu Tyr Cys Phe Arg Lys Asp Met Asp Lys Val Glu Thr Phe Leu Arg
225                 230                 235                 240

Ile Val Gln Cys Arg Ser Val Glu Gly Ser Cys Gly Phe Ser Pro Ala
                245                 250                 255
```

-continued

```
Ser Ala Ser Thr Gln Thr Ser Trp Thr Pro Arg Asp Leu Val Ser Ser
            260                 265                 270

Gln Thr Gln Thr Gln Ser Cys Val Pro Pro Thr Ala Gly Ala Arg Ser
        275                 280                 285

Pro Ala Ser Ala Ser Thr Gln Thr Ser Trp Thr Pro Arg Asp Leu Val
    290                 295                 300

Ser Ser Gln Thr Gln Thr Gln Ser Cys Val Pro Pro Thr Ala Gly Ala
305                 310                 315                 320

Arg

<210> SEQ ID NO 56
<211> LENGTH: 295
<212> TYPE: PRT
<213> ORGANISM: Artificial
<220> FEATURE:
<223> OTHER INFORMATION: Synthetic

<400> SEQUENCE: 56

Gln Ala Pro Glu Ser Pro Ser Thr Ile Pro Val Pro Ser His Pro Ser
1               5                   10                  15

Ser Pro Leu Pro Val Pro Leu Pro Ser Arg Pro Gln Asn Ser Thr Leu
            20                  25                  30

Arg Pro Gly Pro Phe Pro Thr Ile Pro Leu Ser Arg Leu Phe Asp Asn
        35                  40                  45

Ala Met Leu Arg Ala His Arg Leu His Gln Leu Ala Phe Asp Thr Tyr
    50                  55                  60

Gln Glu Phe Glu Glu Ala Tyr Ile Pro Lys Glu Gln Lys Tyr Ser Phe
65                  70                  75                  80

Leu Gln Asn Pro Gln Thr Ser Leu Cys Phe Ser Glu Ser Ile Pro Thr
                85                  90                  95

Pro Ser Asn Arg Glu Glu Thr Gln Gln Lys Ser Asn Leu Glu Leu Leu
            100                 105                 110

Arg Ile Ser Leu Leu Leu Ile Gln Ser Trp Leu Glu Pro Val Gln Phe
        115                 120                 125

Leu Arg Ser Val Phe Ala Asn Ser Leu Val Tyr Gly Ala Ser Asp Ser
    130                 135                 140

Asn Val Tyr Asp Leu Leu Lys Asp Leu Glu Glu Gly Ile Gln Thr Leu
145                 150                 155                 160

Met Gly Arg Leu Glu Asp Gly Ser Pro Arg Thr Gly Gln Ile Phe Lys
                165                 170                 175

Gln Thr Tyr Ser Lys Phe Asp Thr Asn Ser His Asn Asp Asp Ala Leu
            180                 185                 190

Leu Lys Asn Tyr Gly Leu Leu Tyr Cys Phe Arg Lys Asp Met Asp Lys
        195                 200                 205

Val Glu Thr Phe Leu Arg Ile Val Gln Cys Arg Ser Val Glu Gly Ser
    210                 215                 220

Cys Gly Phe Ser Pro Ala Ser Ala Ser Thr Gln Thr Ser Trp Thr Pro
225                 230                 235                 240

Arg Asp Leu Val Ser Ser Gln Thr Gln Thr Gln Ser Cys Val Pro Pro
                245                 250                 255

Thr Ala Gly Ala Arg Ser Pro Ala Ser Ala Ser Thr Gln Thr Ser Trp
            260                 265                 270

Thr Pro Arg Asp Leu Val Ser Ser Gln Thr Gln Thr Gln Ser Cys Val
        275                 280                 285

Pro Pro Thr Ala Gly Ala Arg
```

<210> SEQ ID NO 57
<211> LENGTH: 259
<212> TYPE: PRT
<213> ORGANISM: Artificial
<220> FEATURE:
<223> OTHER INFORMATION: Synthetic

<400> SEQUENCE: 57

```
Met Ala Thr Gly Ser Arg Thr Ser Leu Leu Ala Phe Gly Leu Leu
1               5                   10                  15

Cys Leu Pro Trp Leu Gln Glu Gly Ser Ala Phe Pro Thr Ile Pro Leu
                20                  25                  30

Ser Arg Leu Phe Asp Asn Ala Met Leu Arg Ala His Arg Leu His Gln
            35                  40                  45

Leu Ala Phe Asp Thr Tyr Gln Glu Phe Glu Glu Ala Tyr Ile Pro Lys
        50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

Pro Ala Ser Ala Ser Thr Gln Thr Ser Trp Thr Pro Arg Asp Leu Val
            180                 185                 190

Ser Ser Gln Thr Gln Thr Gln Ser Cys Val Pro Pro Thr Ala Gly Ala
        195                 200                 205

Arg Ser His Asn Asp Asp Ala Leu Leu Lys Asn Tyr Gly Leu Leu Tyr
    210                 215                 220

Cys Phe Arg Lys Asp Met Asp Lys Val Glu Thr Phe Leu Arg Ile Val
225                 230                 235                 240

Gln Cys Arg Ser Val Glu Gly Ser Cys Gly Phe His His His His
                245                 250                 255

His His His
```

<210> SEQ ID NO 58
<211> LENGTH: 251
<212> TYPE: PRT
<213> ORGANISM: Artificial
<220> FEATURE:
<223> OTHER INFORMATION: Synthetic

<400> SEQUENCE: 58

```
Met Ala Thr Gly Ser Arg Thr Ser Leu Leu Ala Phe Gly Leu Leu
1               5                   10                  15

Cys Leu Pro Trp Leu Gln Glu Gly Ser Ala Phe Pro Thr Ile Pro Leu
                20                  25                  30

Ser Arg Leu Phe Asp Asn Ala Met Leu Arg Ala His Arg Leu His Gln
```

```
                35                  40                  45
Leu Ala Phe Asp Thr Tyr Gln Glu Phe Glu Glu Ala Tyr Ile Pro Lys
 50                  55                  60

Glu Gln Lys Tyr Ser Phe Leu Gln Asn Pro Gln Thr Ser Leu Cys Phe
 65                  70                  75                  80

Ser Glu Ser Ile Pro Thr Pro Ser Asn Arg Glu Thr Gln Gln Lys
                 85                  90                  95

Ser Asn Leu Glu Leu Leu Arg Ile Ser Leu Leu Ile Gln Ser Trp
             100                 105                 110

Leu Glu Pro Val Gln Phe Leu Arg Ser Val Phe Ala Asn Ser Leu Val
             115                 120                 125

Tyr Gly Ala Ser Asp Ser Asn Val Tyr Asp Leu Leu Lys Asp Leu Glu
 130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

Pro Ala Ser Ala Ser Thr Gln Thr Ser Trp Thr Pro Arg Asp Leu Val
            180                 185                 190

Ser Ser Gln Thr Gln Thr Gln Ser Cys Val Pro Pro Thr Ala Gly Ala
            195                 200                 205

Arg Ser His Asn Asp Asp Ala Leu Leu Lys Asn Tyr Gly Leu Leu Tyr
210                 215                 220

Cys Phe Arg Lys Asp Met Asp Lys Val Glu Thr Phe Leu Arg Ile Val
225                 230                 235                 240

Gln Cys Arg Ser Val Glu Gly Ser Cys Gly Phe
                245                 250

<210> SEQ ID NO 59
<211> LENGTH: 261
<212> TYPE: PRT
<213> ORGANISM: Artificial
<220> FEATURE:
<223> OTHER INFORMATION: Synthetic

<400> SEQUENCE: 59

Met Ala Thr Gly Ser Arg Thr Ser Leu Leu Leu Ala Phe Gly Leu Leu
 1               5                  10                  15

Cys Leu Pro Trp Leu Gln Glu Gly Ser Ala Phe Pro Thr Ile Pro Leu
                20                  25                  30

Ser Arg Leu Phe Asp Asn Ala Met Leu Arg Ala His Arg Leu His Gln
             35                  40                  45

Leu Ala Phe Asp Thr Tyr Gln Glu Phe Glu Glu Ala Tyr Ile Pro Lys
 50                  55                  60

Glu Gln Lys Tyr Ser Phe Leu Gln Asn Pro Gln Thr Ser Leu Cys Phe
 65                  70                  75                  80

Ser Glu Ser Ile Pro Thr Pro Ser Asn Arg Glu Thr Gln Gln Lys
                 85                  90                  95

Ser Asn Leu Glu Leu Leu Arg Ile Ser Leu Leu Ile Gln Ser Trp
             100                 105                 110

Leu Glu Pro Val Gln Phe Leu Arg Ser Val Phe Ala Asn Ser Leu Val
             115                 120                 125

Tyr Gly Ala Ser Asp Ser Asn Val Tyr Asp Leu Leu Lys Asp Leu Glu
 130                 135                 140

Glu Gly Ile Gln Thr Leu Met Gly Arg Leu Glu Asp Gly Ser Pro Arg
```

```
                145                 150                 155                 160
        Thr Gly Gln Ile Phe Lys Gln Thr Tyr Ser Lys Phe Asp Thr Asn Gln
                        165                 170                 175

Ala Pro Glu Ser Pro Ser Thr Ile Pro Val Pro Ser His Pro Ser Ser
                        180                 185                 190

Pro Leu Pro Val Pro Leu Pro Ser Arg Pro Gln Asn Ser Thr Leu Arg
                        195                 200                 205

Pro Gly Pro Ser His Asn Asp Asp Ala Leu Leu Lys Asn Tyr Gly Leu
                        210                 215                 220

Leu Tyr Cys Phe Arg Lys Asp Met Asp Lys Val Glu Thr Phe Leu Arg
        225                 230                 235                 240

Ile Val Gln Cys Arg Ser Val Glu Gly Ser Cys Gly Phe His His His
                            245                 250                 255

His His His His His
                        260

<210> SEQ ID NO 60
<211> LENGTH: 253
<212> TYPE: PRT
<213> ORGANISM: Artificial
<220> FEATURE:
<223> OTHER INFORMATION: Synthetic

<400> SEQUENCE: 60

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
                20                  25                  30

Ser Arg Leu Phe Asp Asn Ala Met Leu Arg Ala His Arg Leu His Gln
                35                  40                  45

Leu Ala Phe Asp Thr Tyr Gln Glu Phe Glu Glu Ala Tyr Ile Pro Lys
        50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
                100                 105                 110

Leu Glu Pro Val Gln Phe Leu Arg Ser Val Phe Ala Asn Ser Leu Val
                115                 120                 125

Tyr Gly Ala Ser Asp Ser Asn Val Tyr Asp Leu Leu Lys Asp Leu Glu
        130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Gln
                        165                 170                 175

Ala Pro Glu Ser Pro Ser Thr Ile Pro Val Pro Ser His Pro Ser Ser
                        180                 185                 190

Pro Leu Pro Val Pro Leu Pro Ser Arg Pro Gln Asn Ser Thr Leu Arg
                        195                 200                 205

Pro Gly Pro Ser His Asn Asp Asp Ala Leu Leu Lys Asn Tyr Gly Leu
                        210                 215                 220

Leu Tyr Cys Phe Arg Lys Asp Met Asp Lys Val Glu Thr Phe Leu Arg
225                 230                 235                 240

Ile Val Gln Cys Arg Ser Val Glu Gly Ser Cys Gly Phe
```

<210> SEQ ID NO 61
<211> LENGTH: 227
<212> TYPE: PRT
<213> ORGANISM: Artificial
<220> FEATURE:
<223> OTHER INFORMATION: Synthetic

<400> SEQUENCE: 61

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Gln Ala Pro Glu Ser Pro Ser Thr Ile Pro Val
145                 150                 155                 160

Pro Ser His Pro Ser Pro Leu Pro Val Pro Leu Pro Ser Arg Pro
                165                 170                 175

Gln Asn Ser Thr Leu Arg Pro Gly Pro Ser His Asn Asp Asp Ala Leu
            180                 185                 190

Leu Lys Asn Tyr Gly Leu Leu Tyr Cys Phe Arg Lys Asp Met Asp Lys
        195                 200                 205

Val Glu Thr Phe Leu Arg Ile Val Gln Cys Arg Ser Val Glu Gly Ser
    210                 215                 220

Cys Gly Phe
225

<210> SEQ ID NO 62
<211> LENGTH: 227
<212> TYPE: PRT
<213> ORGANISM: Artificial
<220> FEATURE:
<223> OTHER INFORMATION: Synthetic

<400> SEQUENCE: 62

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Gln Ala Pro
    50                  55                  60

-continued

```
Glu Ser Pro Ser Thr Ile Pro Val Pro Ser His Pro Ser Ser Pro Leu
 65                  70                  75                  80

Pro Val Pro Leu Pro Ser Arg Pro Gln Asn Ser Thr Leu Arg Pro Gly
                 85                  90                  95

Pro Ser Asn Arg Glu Glu Thr Gln Gln Lys Ser Asn Leu Glu Leu Leu
            100                 105                 110

Arg Ile Ser Leu Leu Leu Ile Gln Ser Trp Leu Glu Pro Val Gln Phe
        115                 120                 125

Leu Arg Ser Val Phe Ala Asn Ser Leu Val Tyr Gly Ala Ser Asp Ser
130                 135                 140

Asn Val Tyr Asp Leu Leu Lys Asp Leu Glu Glu Gly Ile Gln Thr Leu
145                 150                 155                 160

Met Gly Arg Leu Glu Asp Gly Ser Pro Arg Thr Gly Gln Ile Phe Lys
                165                 170                 175

Gln Thr Tyr Ser Lys Phe Asp Thr Asn Ser His Asn Asp Asp Ala Leu
            180                 185                 190

Leu Lys Asn Tyr Gly Leu Leu Tyr Cys Phe Arg Lys Asp Met Asp Lys
        195                 200                 205

Val Glu Thr Phe Leu Arg Ile Val Gln Cys Arg Ser Val Glu Gly Ser
210                 215                 220

Cys Gly Phe
225

<210> SEQ ID NO 63
<211> LENGTH: 259
<212> TYPE: PRT
<213> ORGANISM: Artificial
<220> FEATURE:
<223> OTHER INFORMATION: Synthetic

<400> SEQUENCE: 63

Met Ala Thr Gly Ser Arg Thr Ser Leu Leu Leu Ala Phe Gly Leu Leu
  1               5                  10                  15

Cys Leu Pro Trp Leu Gln Glu Gly Ser Ala Phe Pro Thr Ile Pro Leu
                 20                  25                  30

Ser Arg Leu Phe Asp Asn Ala Met Leu Arg Ala His Arg Leu His Gln
             35                  40                  45

Leu Ala Phe Asp Thr Tyr Gln Glu Phe Glu Glu Ala Tyr Ile Pro Lys
 50                  55                  60

Glu Gln Lys Tyr Ser Phe Leu Gln Asn Pro Gln Thr Ser Leu Cys Phe
 65                  70                  75                  80

Ser Glu Ser Ile Pro Thr Pro Ser Pro Ala Ser Ala Ser Thr Gln Thr
                 85                  90                  95

Ser Trp Thr Pro Arg Asp Leu Val Ser Ser Gln Thr Gln Thr Gln Ser
            100                 105                 110

Cys Val Pro Pro Thr Ala Gly Ala Arg Ser Asn Arg Glu Glu Thr Gln
        115                 120                 125

Gln Lys Ser Asn Leu Glu Leu Leu Arg Ile Ser Leu Leu Leu Ile Gln
130                 135                 140

Ser Trp Leu Glu Pro Val Gln Phe Leu Arg Ser Val Phe Ala Asn Ser
145                 150                 155                 160

Leu Val Tyr Gly Ala Ser Asp Ser Asn Val Tyr Asp Leu Leu Lys Asp
                165                 170                 175

Leu Glu Glu Gly Ile Gln Thr Leu Met Gly Arg Leu Glu Asp Gly Ser
            180                 185                 190
```

Pro Arg Thr Gly Gln Ile Phe Lys Gln Thr Tyr Ser Lys Phe Asp Thr
                195                 200                 205

Asn Ser His Asn Asp Asp Ala Leu Leu Lys Asn Tyr Gly Leu Leu Tyr
            210                 215                 220

Cys Phe Arg Lys Asp Met Asp Lys Val Glu Thr Phe Leu Arg Ile Val
225                 230                 235                 240

Gln Cys Arg Ser Val Glu Gly Ser Cys Gly Phe His His His His His
                245                 250                 255

His His His

<210> SEQ ID NO 64
<211> LENGTH: 225
<212> TYPE: PRT
<213> ORGANISM: Artificial
<220> FEATURE:
<223> OTHER INFORMATION: Synthetic

<400> SEQUENCE: 64

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
                20                  25                  30

Glu Ala Tyr Ile Pro Lys Glu Gln Lys Tyr Ser Phe Leu Gln Asn Pro
            35                  40                  45

Gln Thr Ser Leu Cys Phe Ser Glu Ser Ile Pro Thr Pro Ser Pro Ala
        50                  55                  60

Ser Ala Ser Thr Gln Thr Ser Trp Thr Pro Arg Asp Leu Val Ser Ser
65                  70                  75                  80

Gln Thr Gln Thr Gln Ser Cys Val Pro Pro Thr Ala Gly Ala Arg Ser
                85                  90                  95

Asn Arg Glu Glu Thr Gln Gln Lys Ser Asn Leu Glu Leu Leu Arg Ile
            100                 105                 110

Ser Leu Leu Leu Ile Gln Ser Trp Leu Glu Pro Val Gln Phe Leu Arg
        115                 120                 125

Ser Val Phe Ala Asn Ser Leu Val Tyr Gly Ala Ser Asp Ser Asn Val
130                 135                 140

Tyr Asp Leu Leu Lys Asp Leu Glu Glu Gly Ile Gln Thr Leu Met Gly
145                 150                 155                 160

Arg Leu Glu Asp Gly Ser Pro Arg Thr Gly Gln Ile Phe Lys Gln Thr
                165                 170                 175

Tyr Ser Lys Phe Asp Thr Asn Ser His Asn Asp Asp Ala Leu Leu Lys
            180                 185                 190

Asn Tyr Gly Leu Leu Tyr Cys Phe Arg Lys Asp Met Asp Lys Val Glu
        195                 200                 205

Thr Phe Leu Arg Ile Val Gln Cys Arg Ser Val Glu Gly Ser Cys Gly
    210                 215                 220

Phe
225

<210> SEQ ID NO 65
<211> LENGTH: 240
<212> TYPE: PRT
<213> ORGANISM: Artificial
<220> FEATURE:
<223> OTHER INFORMATION: Synthetic

<400> SEQUENCE: 65

Met Tyr Arg Met Leu Leu Ser Cys Ile Ala Leu Ser Leu Ala Leu Val
1               5                   10                  15

Thr Asn Gly Ser Ala Ser Pro Ala Ser Ala Ser Thr Gln Thr Ser Trp
            20                  25                  30

Thr Pro Arg Asp Leu Val Ser Ser Gln Thr Gln Thr Gln Ser Cys Val
            35                  40                  45

Pro Pro Thr Ala Gly Ala Arg Ala Pro Thr Ser Ser Ser Thr Lys Lys
50                  55                  60

Thr Gln Leu Gln Leu Glu His Leu Leu Leu Asp Leu Gln Met Ile Leu
65                  70                  75                  80

Asn Gly Ile Asn Asn Tyr Lys Asn Pro Lys Leu Thr Arg Met Leu Thr
                85                  90                  95

Phe Lys Phe Tyr Met Pro Lys Lys Ala Thr Glu Leu Lys His Leu Gln
                100                 105                 110

Cys Leu Glu Glu Glu Leu Lys Pro Leu Glu Glu Val Leu Asn Leu Ala
            115                 120                 125

Gln Ser Lys Asn Phe His Leu Arg Pro Arg Asp Leu Ile Ser Asn Ile
        130                 135                 140

Asn Val Ile Val Leu Glu Leu Lys Gly Ser Glu Thr Thr Phe Met Cys
145                 150                 155                 160

Glu Tyr Ala Asp Glu Thr Ala Thr Ile Val Glu Phe Leu Asn Arg Trp
                165                 170                 175

Ile Thr Phe Cys Gln Ser Ile Ile Ser Thr Leu Thr Gln Ala Pro Glu
                180                 185                 190

Ser Pro Ser Thr Ile Pro Val Pro Ser His Pro Ser Ser Pro Leu Pro
            195                 200                 205

Val Pro Leu Pro Ser Arg Pro Gln Asn Ser Thr Leu Arg Pro Gly Pro
210                 215                 220

Leu Glu Val Leu Phe Gln Gly Pro His His His His His His
225                 230                 235                 240

<210> SEQ ID NO 66
<211> LENGTH: 203
<212> TYPE: PRT
<213> ORGANISM: Artificial
<220> FEATURE:
<223> OTHER INFORMATION: Synthetic

<400> SEQUENCE: 66

Ser Pro Ala Ser Ala Ser Thr Gln Thr Ser Trp Thr Pro Arg Asp Leu
1               5                   10                  15

Val Ser Ser Gln Thr Gln Thr Gln Ser Cys Val Pro Pro Thr Ala Gly
            20                  25                  30

Ala Arg Ala Pro Thr Ser Ser Ser Thr Lys Lys Thr Gln Leu Gln Leu
        35                  40                  45

Glu His Leu Leu Leu Asp Leu Gln Met Ile Leu Asn Gly Ile Asn Asn
50                  55                  60

Tyr Lys Asn Pro Lys Leu Thr Arg Met Leu Thr Phe Lys Phe Tyr Met
65                  70                  75                  80

Pro Lys Lys Ala Thr Glu Leu Lys His Leu Gln Cys Leu Glu Glu Glu
                85                  90                  95

Leu Lys Pro Leu Glu Glu Val Leu Asn Leu Ala Gln Ser Lys Asn Phe
            100                 105                 110

His Leu Arg Pro Arg Asp Leu Ile Ser Asn Ile Asn Val Ile Val Leu
        115                 120                 125

-continued

```
Glu Leu Lys Gly Ser Glu Thr Thr Phe Met Cys Glu Tyr Ala Asp Glu
130                 135                 140

Thr Ala Thr Ile Val Glu Phe Leu Asn Arg Trp Ile Thr Phe Cys Gln
145                 150                 155                 160

Ser Ile Ile Ser Thr Leu Thr Gln Ala Pro Glu Ser Pro Ser Thr Ile
                165                 170                 175

Pro Val Pro Ser His Pro Ser Ser Pro Leu Pro Val Pro Leu Pro Ser
            180                 185                 190

Arg Pro Gln Asn Ser Thr Leu Arg Pro Gly Pro
        195                 200
```

<210> SEQ ID NO 67
<211> LENGTH: 242
<212> TYPE: PRT
<213> ORGANISM: Artificial
<220> FEATURE:
<223> OTHER INFORMATION: Synthetic

<400> SEQUENCE: 67

```
Met Tyr Arg Met Leu Leu Ser Cys Ile Ala Leu Ser Leu Ala Leu Val
1               5                   10                  15

Thr Asn Gly Ser Ala Gln Ala Pro Glu Ser Pro Ser Thr Ile Pro Val
            20                  25                  30

Pro Ser His Pro Ser Ser Pro Leu Pro Val Pro Leu Pro Ser Arg Pro
        35                  40                  45

Gln Asn Ser Thr Leu Arg Pro Gly Pro Ala Pro Thr Ser Ser Ser Thr
    50                  55                  60

Lys Lys Thr Gln Leu Gln Leu Glu His Leu Leu Leu Asp Leu Gln Met
65                  70                  75                  80

Ile Leu Asn Gly Ile Asn Asn Tyr Lys Asn Pro Lys Leu Thr Arg Met
                85                  90                  95

Leu Thr Phe Lys Phe Tyr Met Pro Lys Lys Ala Thr Glu Leu Lys His
            100                 105                 110

Leu Gln Cys Leu Glu Glu Glu Leu Lys Pro Leu Glu Glu Val Leu Asn
        115                 120                 125

Leu Ala Gln Ser Lys Asn Phe His Leu Arg Pro Arg Asp Leu Ile Ser
    130                 135                 140

Asn Ile Asn Val Ile Val Leu Glu Leu Lys Gly Ser Glu Thr Thr Phe
145                 150                 155                 160

Met Cys Glu Tyr Ala Asp Glu Thr Ala Thr Ile Val Glu Phe Leu Asn
                165                 170                 175

Arg Trp Ile Thr Phe Cys Gln Ser Ile Ile Ser Thr Leu Thr Gln Ala
            180                 185                 190

Pro Glu Ser Pro Ser Thr Ile Pro Val Pro Ser His Pro Ser Ser Pro
        195                 200                 205

Leu Pro Val Pro Leu Pro Ser Arg Pro Gln Asn Ser Thr Leu Arg Pro
    210                 215                 220

Gly Pro Leu Glu Val Leu Phe Gln Gly Pro His His His His His His
225                 230                 235                 240

His His
```

<210> SEQ ID NO 68
<211> LENGTH: 205
<212> TYPE: PRT
<213> ORGANISM: Artificial
<220> FEATURE:
<223> OTHER INFORMATION: Synthetic

<400> SEQUENCE: 68

```
Gln Ala Pro Glu Ser Pro Ser Thr Ile Pro Val Pro Ser His Pro Ser
1               5                   10                  15

Ser Pro Leu Pro Val Pro Leu Pro Ser Arg Pro Gln Asn Ser Thr Leu
            20                  25                  30

Arg Pro Gly Pro Ala Pro Thr Ser Ser Ser Thr Lys Lys Thr Gln Leu
        35                  40                  45

Gln Leu Glu His Leu Leu Leu Asp Leu Gln Met Ile Leu Asn Gly Ile
    50                  55                  60

Asn Asn Tyr Lys Asn Pro Lys Leu Thr Arg Met Leu Thr Phe Lys Phe
65                  70                  75                  80

Tyr Met Pro Lys Lys Ala Thr Glu Leu Lys His Leu Gln Cys Leu Glu
                85                  90                  95

Glu Glu Leu Lys Pro Leu Glu Glu Val Leu Asn Leu Ala Gln Ser Lys
            100                 105                 110

Asn Phe His Leu Arg Pro Arg Asp Leu Ile Ser Asn Ile Asn Val Ile
        115                 120                 125

Val Leu Glu Leu Lys Gly Ser Glu Thr Thr Phe Met Cys Glu Tyr Ala
130                 135                 140

Asp Glu Thr Ala Thr Ile Val Glu Phe Leu Asn Arg Trp Ile Thr Phe
145                 150                 155                 160

Cys Gln Ser Ile Ile Ser Thr Leu Thr Gln Ala Pro Glu Ser Pro Ser
                165                 170                 175

Thr Ile Pro Val Pro Ser His Pro Ser Ser Pro Leu Pro Val Pro Leu
            180                 185                 190

Pro Ser Arg Pro Gln Asn Ser Thr Leu Arg Pro Gly Pro
        195                 200                 205
```

<210> SEQ ID NO 69
<211> LENGTH: 238
<212> TYPE: PRT
<213> ORGANISM: Artificial
<220> FEATURE:
<223> OTHER INFORMATION: Synthetic

<400> SEQUENCE: 69

```
Met Tyr Arg Met Leu Leu Ser Cys Ile Ala Leu Ser Leu Ala Leu Val
1               5                   10                  15

Thr Asn Gly Ser Ala Ser Pro Ala Ser Ala Ser Thr Gln Thr Ser Trp
            20                  25                  30

Thr Pro Arg Asp Leu Val Ser Ser Gln Thr Gln Thr Gln Ser Cys Val
        35                  40                  45

Pro Pro Thr Ala Gly Ala Arg Ala Pro Thr Ser Ser Ser Thr Lys Lys
    50                  55                  60

Thr Gln Leu Gln Leu Glu His Leu Leu Leu Asp Leu Gln Met Ile Leu
65                  70                  75                  80

Asn Gly Ile Asn Asn Tyr Lys Asn Pro Lys Leu Thr Arg Met Leu Thr
                85                  90                  95

Phe Lys Phe Tyr Met Pro Lys Lys Ala Thr Glu Leu Lys His Leu Gln
            100                 105                 110

Cys Leu Glu Glu Glu Leu Lys Pro Leu Glu Glu Val Leu Asn Leu Ala
        115                 120                 125

Gln Ser Lys Asn Phe His Leu Arg Pro Arg Asp Leu Ile Ser Asn Ile
    130                 135                 140
```

```
Asn Val Ile Val Leu Glu Leu Lys Gly Ser Glu Thr Thr Phe Met Cys
145                 150                 155                 160

Glu Tyr Ala Asp Glu Thr Ala Thr Ile Val Glu Phe Leu Asn Arg Trp
                165                 170                 175

Ile Thr Phe Cys Gln Ser Ile Ile Ser Thr Leu Thr Ser Pro Ala Ser
                180                 185                 190

Ala Ser Thr Gln Thr Ser Trp Thr Pro Arg Asp Leu Val Ser Ser Gln
            195                 200                 205

Thr Gln Thr Gln Ser Cys Val Pro Pro Thr Ala Gly Ala Arg Leu Glu
        210                 215                 220

Val Leu Phe Gln Gly Pro His His His His His His His
225                 230                 235
```

<210> SEQ ID NO 70
<211> LENGTH: 201
<212> TYPE: PRT
<213> ORGANISM: Artificial
<220> FEATURE:
<223> OTHER INFORMATION: Synthetic

<400> SEQUENCE: 70

```
Ser Pro Ala Ser Ala Ser Thr Gln Thr Ser Trp Thr Pro Arg Asp Leu
1               5                   10                  15

Val Ser Ser Gln Thr Gln Thr Gln Ser Cys Val Pro Pro Thr Ala Gly
                20                  25                  30

Ala Arg Ala Pro Thr Ser Ser Ser Thr Lys Lys Thr Gln Leu Gln Leu
            35                  40                  45

Glu His Leu Leu Leu Asp Leu Gln Met Ile Leu Asn Gly Ile Asn Asn
        50                  55                  60

Tyr Lys Asn Pro Lys Leu Thr Arg Met Leu Thr Phe Lys Phe Tyr Met
65                  70                  75                  80

Pro Lys Lys Ala Thr Glu Leu Lys His Leu Gln Cys Leu Glu Glu Glu
                85                  90                  95

Leu Lys Pro Leu Glu Glu Val Leu Asn Leu Ala Gln Ser Lys Asn Phe
                100                 105                 110

His Leu Arg Pro Arg Asp Leu Ile Ser Asn Ile Asn Val Ile Val Leu
            115                 120                 125

Glu Leu Lys Gly Ser Glu Thr Thr Phe Met Cys Glu Tyr Ala Asp Glu
130                 135                 140

Thr Ala Thr Ile Val Glu Phe Leu Asn Arg Trp Ile Thr Phe Cys Gln
145                 150                 155                 160

Ser Ile Ile Ser Thr Leu Thr Ser Pro Ala Ser Ala Ser Thr Gln Thr
                165                 170                 175

Ser Trp Thr Pro Arg Asp Leu Val Ser Ser Gln Thr Gln Thr Gln Ser
            180                 185                 190

Cys Val Pro Pro Thr Ala Gly Ala Arg
        195                 200
```

<210> SEQ ID NO 71
<211> LENGTH: 293
<212> TYPE: PRT
<213> ORGANISM: Artificial
<220> FEATURE:
<223> OTHER INFORMATION: Synthetic

<400> SEQUENCE: 71

```
Ser Pro Ala Ser Ala Ser Thr Gln Thr Ser Trp Thr Pro Arg Asp Leu
1               5                   10                  15
```

-continued

```
Val Ser Ser Gln Thr Gln Thr Gln Ser Cys Val Pro Pro Thr Ala Gly
            20              25              30

Ala Arg Ser Pro Ala Ser Ala Ser Thr Gln Thr Ser Trp Thr Pro Arg
        35              40              45

Asp Leu Val Ser Ser Gln Thr Gln Thr Gln Ser Cys Val Pro Pro Thr
    50              55              60

Ala Gly Ala Arg Phe Pro Thr Ile Pro Leu Ser Arg Leu Phe Asp Asn
65              70              75              80

Ala Met Leu Arg Ala His Arg Leu His Gln Leu Ala Phe Asp Thr Tyr
                85              90              95

Gln Glu Phe Glu Glu Ala Tyr Ile Pro Lys Glu Gln Lys Tyr Ser Phe
            100             105             110

Leu Gln Asn Pro Gln Thr Ser Leu Cys Phe Ser Glu Ser Ile Pro Thr
            115             120             125

Pro Ser Asn Arg Glu Glu Thr Gln Gln Lys Ser Asn Leu Glu Leu Leu
130             135             140

Arg Ile Ser Leu Leu Leu Ile Gln Ser Trp Leu Glu Pro Val Gln Phe
145             150             155             160

Leu Arg Ser Val Phe Ala Asn Ser Leu Val Tyr Gly Ala Ser Asp Ser
                165             170             175

Asn Val Tyr Asp Leu Leu Lys Asp Leu Glu Glu Gly Ile Gln Thr Leu
            180             185             190

Met Gly Arg Leu Glu Asp Gly Ser Pro Arg Thr Gly Gln Ile Phe Lys
        195             200             205

Gln Thr Tyr Ser Lys Phe Asp Thr Asn Ser His Asn Asp Asp Ala Leu
    210             215             220

Leu Lys Asn Tyr Gly Leu Leu Tyr Cys Phe Arg Lys Asp Met Asp Lys
225             230             235             240

Val Glu Thr Phe Leu Arg Ile Val Gln Cys Arg Ser Val Glu Gly Ser
            245             250             255

Cys Gly Phe Ser Pro Ala Ser Ala Ser Thr Gln Thr Ser Trp Thr Pro
            260             265             270

Arg Asp Leu Val Ser Ser Gln Thr Gln Thr Gln Ser Cys Val Pro Pro
        275             280             285

Thr Ala Gly Ala Arg
        290
```